US 11,419,691 B2

(12) United States Patent
Kim et al.

(10) Patent No.: US 11,419,691 B2
(45) Date of Patent: Aug. 23, 2022

(54) SURGICAL APPARATUS

(71) Applicants: THE BOARD OF REGENTS OF THE UNIVERSITY OF TEXAS SYSTEM, Austin, TX (US); COLUBRISMX, INC., Houston, TX (US)

(72) Inventors: Daniel H. Kim, Houston, TX (US); Dong Suk Shin, Houston, TX (US); Taeho Jang, Houston, TX (US); Yongman Park, Houston, TX (US); Jeihan Lee, Houston, TX (US); Hongmin Kim, Houston, TX (US); Kihoon Nam, Houston, TX (US); Seokyung Han, Houston, TX (US)

(73) Assignees: THE BOARD OF REGENTS OF THE UNIVERSITY OF TEXAS SYSTEM, Austin, TX (US); COLUBRISMX, INC., Houston, TX (US)

( * ) Notice: Subject to any disclaimer, the term of this patent is extended or adjusted under 35 U.S.C. 154(b) by 16 days.

(21) Appl. No.: 16/495,028

(22) PCT Filed: Jun. 28, 2018

(86) PCT No.: PCT/US2018/039943
§ 371 (c)(1),
(2) Date: Sep. 17, 2019

(87) PCT Pub. No.: WO2019/006087
PCT Pub. Date: Jan. 3, 2019

(65) Prior Publication Data
US 2020/0107898 A1    Apr. 9, 2020

Related U.S. Application Data

(60) Provisional application No. 62/526,881, filed on Jun. 29, 2017.

(51) Int. Cl.
*A61B 34/00* (2016.01)
*A61B 34/30* (2016.01)
(Continued)

(52) U.S. Cl.
CPC ............ *A61B 34/71* (2016.02); *A61B 17/295* (2013.01); *A61B 17/320016* (2013.01);
(Continued)

(58) Field of Classification Search
CPC ......... A61B 34/71; A61B 34/30; A61B 34/74; A61B 17/295; A61B 17/320016;
(Continued)

(56) References Cited

U.S. PATENT DOCUMENTS

| 5,788,628 A * | 8/1998 | Matsuno ............ A61B 1/00091 600/121 |
| 2001/0025133 A1 * | 9/2001 | Staud ...................... A61L 2/186 600/121 |

(Continued)

FOREIGN PATENT DOCUMENTS

| CN | 106361433 A | 2/2017 |
| EP | 1906858 A1 | 4/2008 |

(Continued)

OTHER PUBLICATIONS

Australian Search Report for Application No. 2018290914 dated Feb. 18, 2020.
(Continued)

*Primary Examiner* — Kathleen S Holwerda
*Assistant Examiner* — Uyen N Vo
(74) *Attorney, Agent, or Firm* — Patterson + Sheridan, LLP

(57) ABSTRACT

The disclosure provides a surgical apparatus comprising: a steerable member that is bendable and comprises a plurality of bending segments with channels therein; and a plurality
(Continued)

of bending actuation wires that are arranged to pass through the steerable member and cause the steerable member to bend, the steerable member comprising at least one outwardly opening lumen through which the bending actuation wires pass.

11 Claims, 53 Drawing Sheets

(51) Int. Cl.
    *A61B 17/295*     (2006.01)
    *A61B 17/32*     (2006.01)
    *A61B 17/00*     (2006.01)
    *A61B 17/29*     (2006.01)

(52) U.S. Cl.
    CPC .............. *A61B 34/30* (2016.02); *A61B 34/74* (2016.02); *A61B 2017/00309* (2013.01); *A61B 2017/00314* (2013.01); *A61B 2017/00327* (2013.01); *A61B 2017/2906* (2013.01); *A61B 2034/301* (2016.02)

(58) Field of Classification Search
    CPC .... A61B 2034/301; A61B 2017/00309; A61B 2017/00314; A61B 2017/00327; A61B 2017/2906; A61B 1/018; A61B 1/0051; A61B 1/0016; A61B 2017/00876; A61B 17/29; A61B 2017/00017; A61B 2017/00477; A61B 34/37; A61B 2034/303; A61B 2034/306; A61B 2017/2908; A61B 2017/00318; A61B 2017/00296; A61B 2017/00265; A61B 1/008; A61B 1/0057; A61B 90/10; A61B 2090/101

See application file for complete search history.

(56) References Cited

U.S. PATENT DOCUMENTS

| | | |
|---|---|---|
| 2004/0138529 A1 | 7/2004 | Wiltshire et al. |
| 2004/0193146 A1* | 9/2004 | Lee ..................... A61B 17/062 606/1 |
| 2006/0264705 A1 | 11/2006 | Adams et al. |
| 2007/0239186 A1 | 10/2007 | Weitzner et al. |
| 2008/0243064 A1* | 10/2008 | Stabler .................. A61B 34/30 604/95.01 |
| 2008/0249362 A1* | 10/2008 | Jiang .................. A61B 1/00135 600/121 |
| 2008/0287963 A1 | 11/2008 | Rogers et al. |
| 2010/0331856 A1 | 12/2010 | Carlson et al. |
| 2011/0071543 A1* | 3/2011 | Prisco .................... A61B 90/92 600/118 |
| 2011/0301416 A1* | 12/2011 | Dejima .............. A61B 17/0487 600/114 |
| 2012/0071895 A1* | 3/2012 | Stabler .................... A61B 6/12 606/130 |
| 2015/0230697 A1 | 8/2015 | Phee et al. |

FOREIGN PATENT DOCUMENTS

| | | |
|---|---|---|
| EP | 2996613 A1 | 3/2016 |
| WO | 2009094670 A1 | 7/2009 |
| WO | 2010002544 A1 | 1/2010 |
| WO | 2010050771 A2 | 5/2010 |
| WO | 2012015816 A1 | 2/2012 |
| WO | 2016148642 A1 | 9/2016 |

OTHER PUBLICATIONS

Canadian Patent Application No. 3,048,492, Office Action dated Sep. 9, 2020, 3 pages.
PCT International Search Report and Written Opinion for Application No. PCT/US2018/039943, dated Jan. 15, 2019.
European Patent Application No. 18825116.9, Communication re Extended Search Report, dated Jul. 6, 2020 9 pages.
Australian Search Report for Application No. 2018290914 dated Jun. 25, 2020, 3 pages.
European Patent Application No. 20204919.3, Extended European Search Report dated Mar. 9, 2021, 8 pages.
Korean Patent Application No. 10-2019-7019373, Office Action dated Mar. 22, 2021 with English Translation, 8 pages.

* cited by examiner

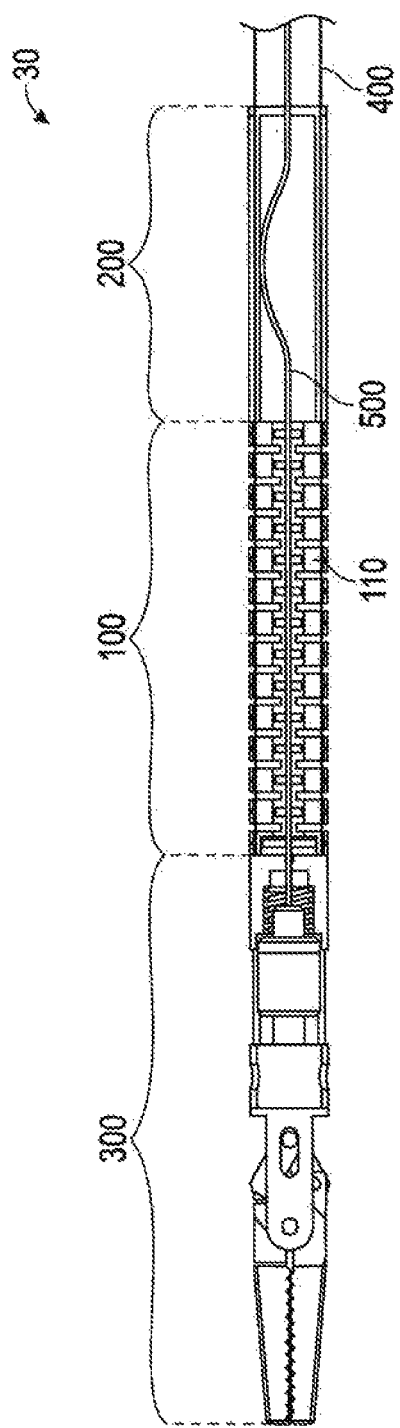

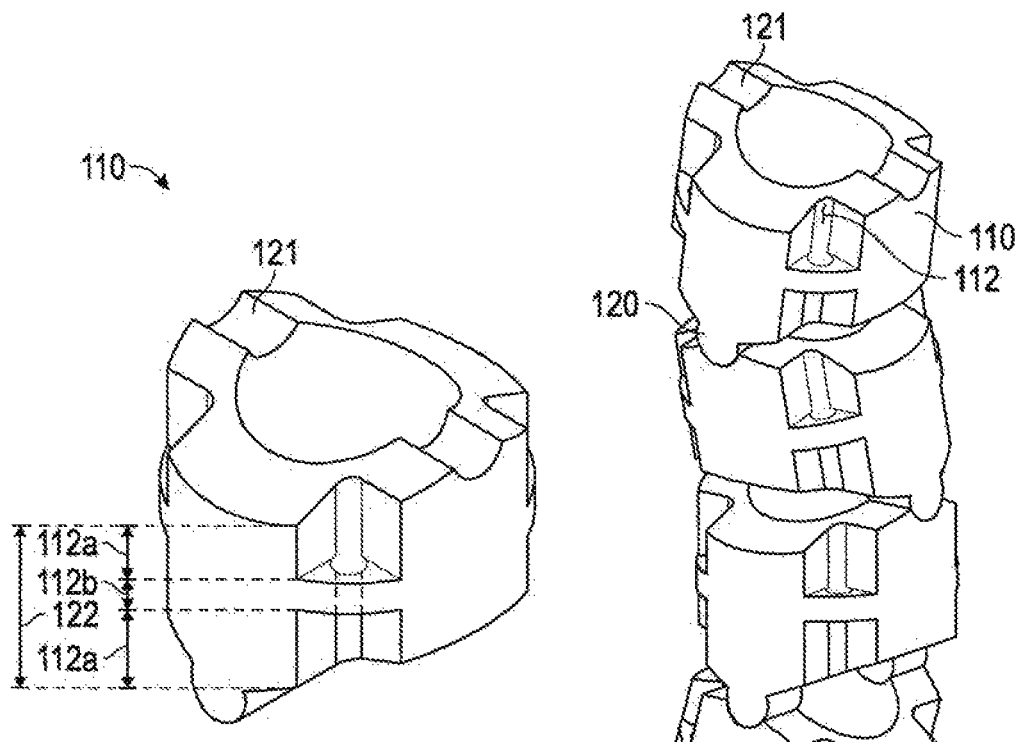
FIG. 8A
FIG. 8B
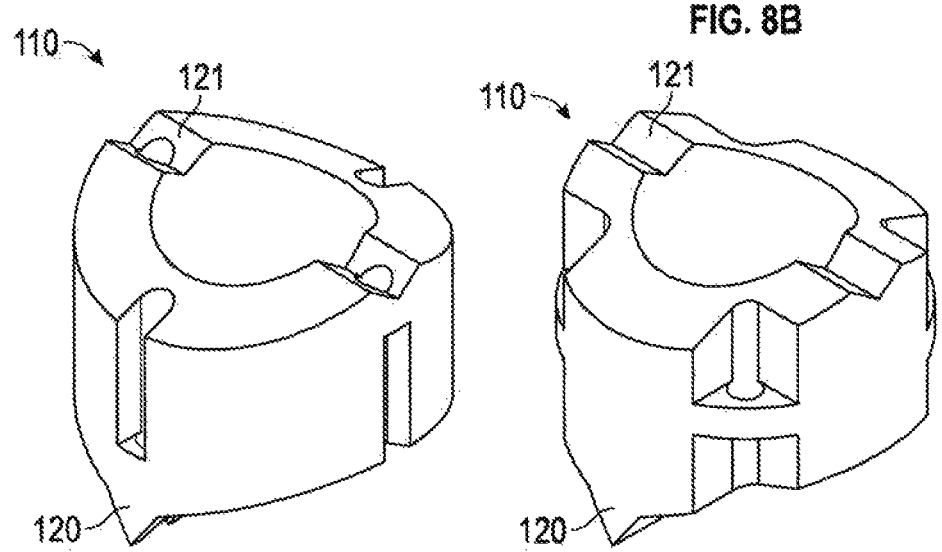
FIG. 9A
FIG. 9B

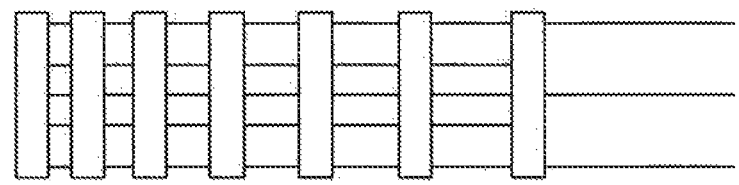
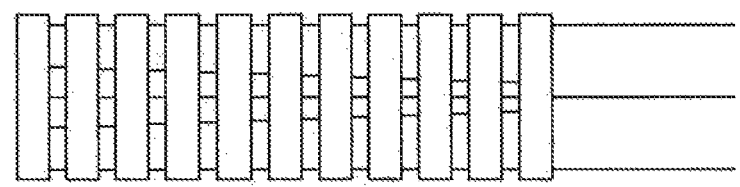
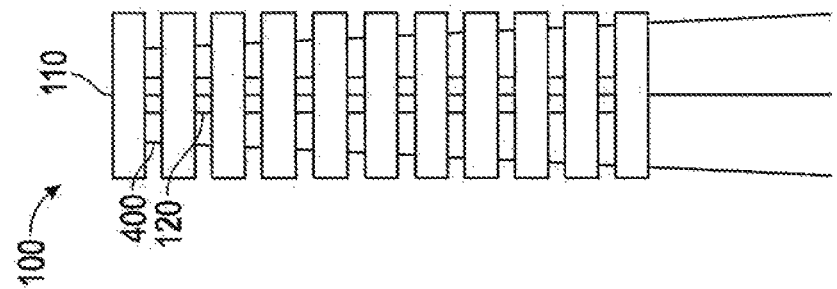
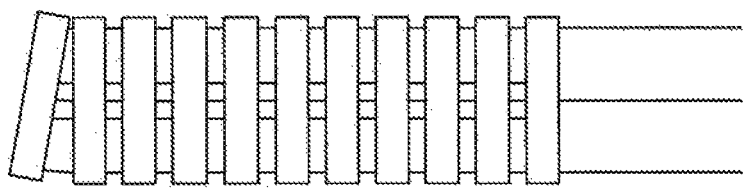
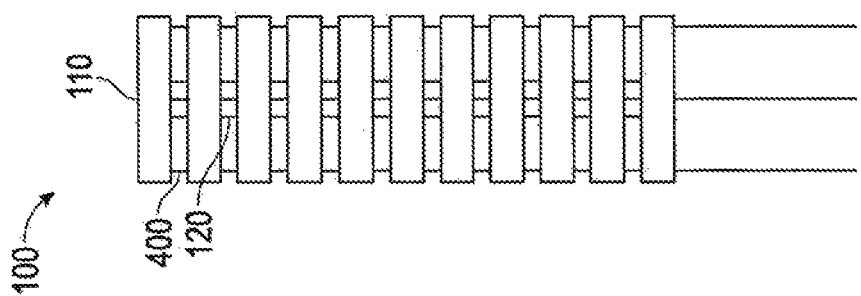

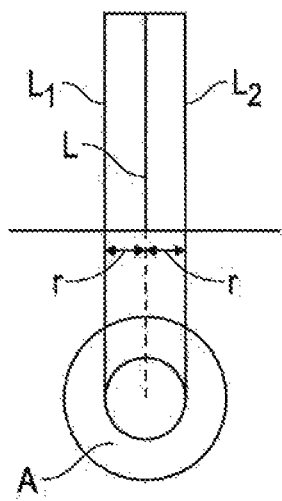 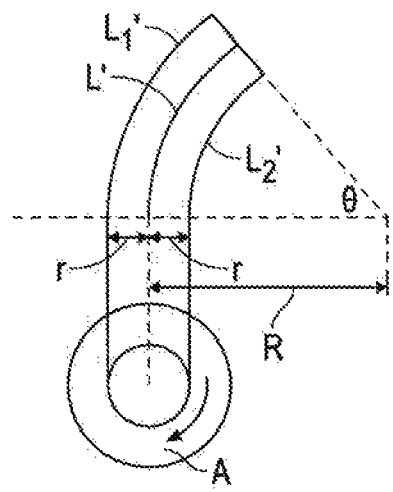
FIG. 33A  FIG. 33B
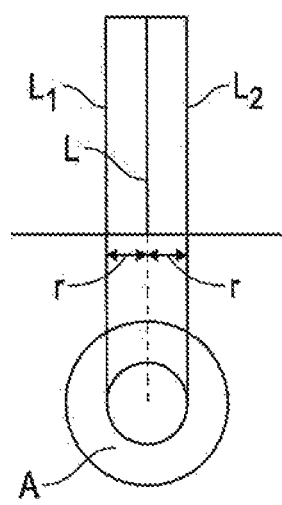 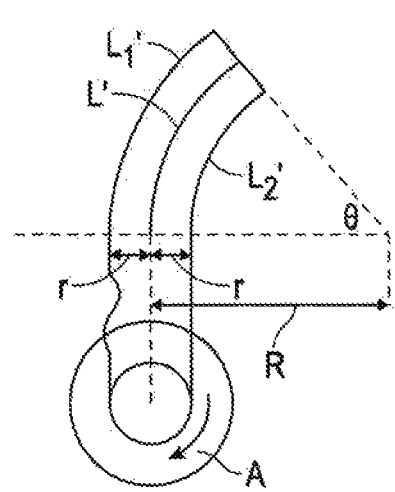
FIG. 34A  FIG. 34B

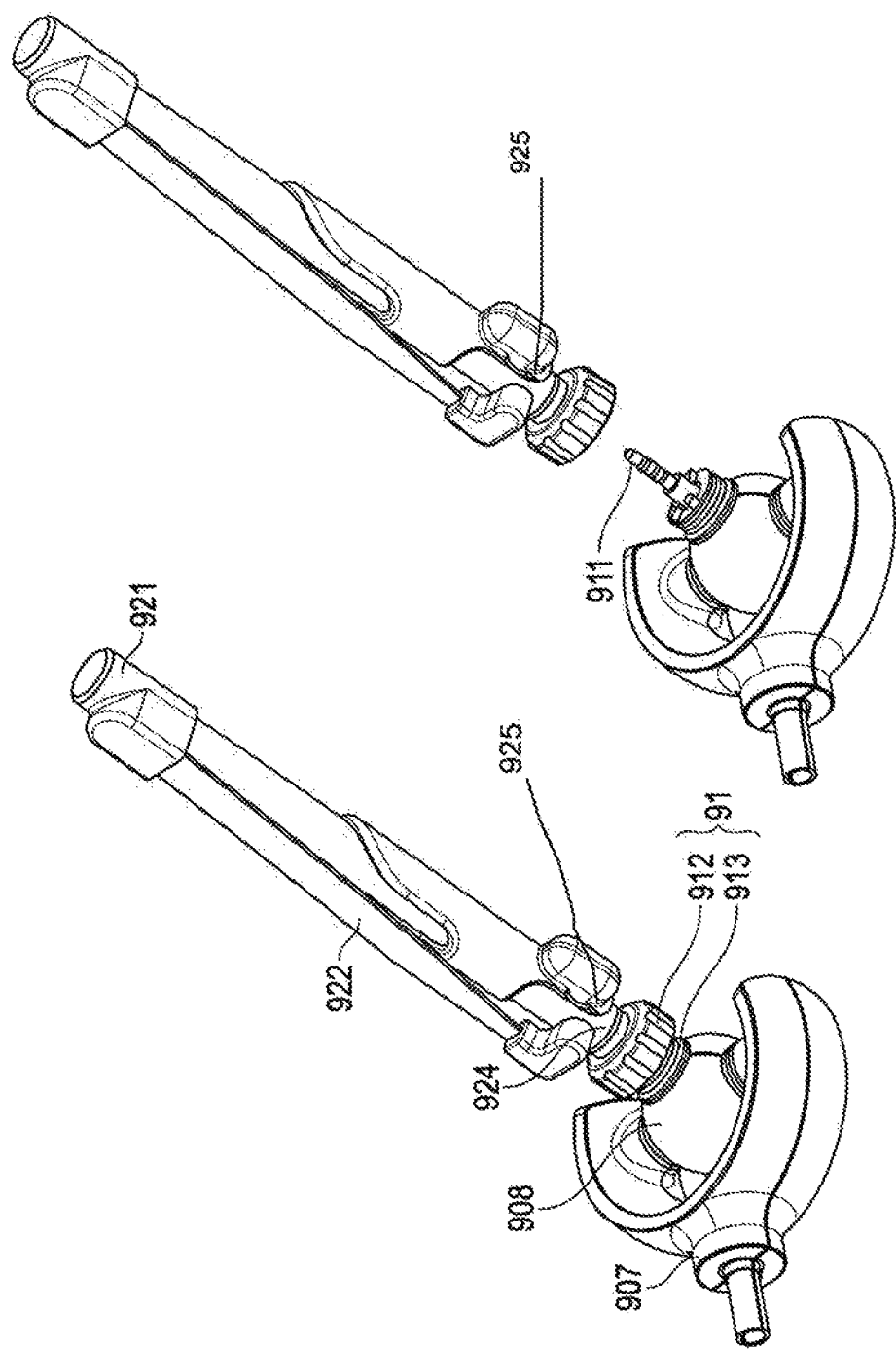

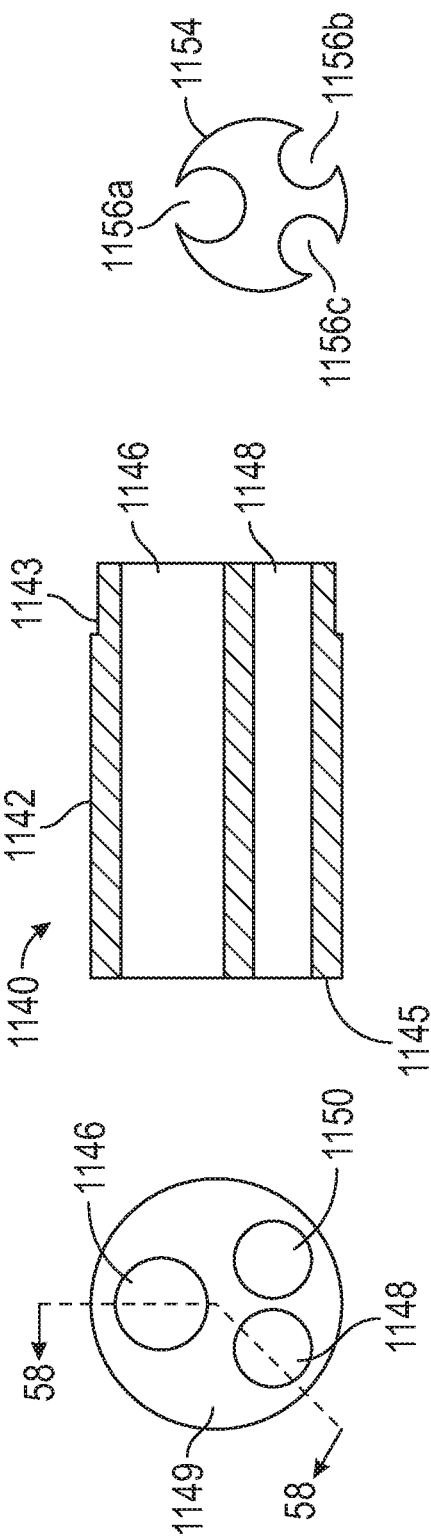

SURGICAL APPARATUS

CROSS-REFERENCE TO RELATED APPLICATION

This application for Patent is a national stage application under 35 U.S.C. 371 of PCT/US2018/039943, filed Jun. 28, 2018, which claims benefit of U.S. Provisional Application Ser. No. 62/526,881, filed Jun. 29, 2017, entitled "SURGICAL APPARATUS," which are both incorporated herein by reference in their entireties.

TECHNICAL FIELD

The present invention relates to a surgical apparatus, and more particularly, to a surgical apparatus which is capable of performing a bending operation by including a bendable element at the distal end thereof.

BACKGROUND OF THE RELATED ART

Surgical apparatuses used in surgery have different structures depending on the location of a surgical site and how the surgical site will be treated. In recent years, various types of surgical equipment using a robot are being developed to perform surgery on areas where surgical sites are difficult to access by existing surgical apparatuses or to perform a minimally invasive surgery. These surgical apparatuses are configured to move in various directions in the human body by including a bendable element, which are disclosed in many documents including U.S. Pat. No. 6,858,005.

Surgical apparatuses bendable at the distal end thereof bend by the movement of wires inside them. However, these surgical apparatuses are hard to finely manipulate, revealing some problems like creating backlash when they are bent with the wires or restricting the movement of other wires when bent or bending. Also, these surgical apparatuses have many components embedded in them which are connected to one another in a complicated way, so it is difficult to miniaturize them.

SUMMARY OF THE DISCLOSURE

Provided herein is an endoscopic device, including a first tubular element, a second tubular element and a third tubular element, wherein each of the second and third tubular elements include, at a distal end thereof, an end effector, and a mechanical carriage, from which at least the second and third tubular members extend, which is configured to, under the control of an operator, move the distal ends of the second and third tubular members linearly and orbitally around a central axis. Additionally, each of the end effectors at the distal ends of the second and third tubular members is connected to a robotic controller moveably mounted within the mechanical carriage, configured to independently move the distal ends of the second and third tubular members linearly and rotationally with respect to a longitudinal axis thereof.

In one aspect, the first, second and third tubular elements are coupled to one another by coupling members arranged at a plurality of locations along the length thereof, wherein the coupling member restrains movement of the tubular members with respect to the orbital axis, but permit at least the second and third tubular members to move linearly with respect to the first tubular member. In a further aspect, the first, second and third members, and the coupling members, are surrounded in an enclosed sheath, such as a biocompatible tube.

In another aspect, the end effectors include a conformable extension including a set of linkages extending from the distal end of at least one of the second or third tubular members on one end thereof, and include a tool element at the opposite end thereof, wherein each linkage includes a central axis therethrough, and the axis of the linkages may be collinear wherein the linkages together configure the conformable extension as a generally straight element extending from the distal end of the second or third tubular member to the tool element, or the axis of at least one pair of adjacent linkages are at an angle to one another, such that the conformable extension is bent. Additionally, by rotation of the tubular member to which it is connected, the conformable extension is rotated about an internal axis thereof. The robotic controller is coupled, to the conformable extension to enable the bending and rotational movements of the second and third tubular members, and the mechanical carriage moves the robotic controllers, and thus the second and third tubular members attached thereto, linearly under the control of an operator. The end effectors may include forceps, cutting blades, combined forceps and cutting blades, and other elements, by which an operator such as a surgeon my remove, by cutting away a portion of a body lumen, and then suture closed the resulting wound.

BRIEF DESCRIPTION OF THE DRAWINGS

Hereinafter, a surgical apparatus according to exemplary embodiments of the present invention will be described concretely with reference to the drawings. A description of the positional relationship between the components will now be made basically with reference to the drawings. In the drawings, structures of the embodiments may be simplified or exaggerated for clarity. Accordingly, the present invention is not limited to these exemplary embodiments, but instead various kinds of devices may be added, changed, or omitted.

The exemplary embodiments will be described with respect to a surgical apparatus that has a plurality of passages inside an insertion part, with various kinds of surgical instruments located in each passage. However, it is to be noted that the present invention is not limited to this exemplary embodiment and is applicable to a variety of surgical apparatuses, including catheters, endoscopes, and surgical robots, that are bendable at the distal end.

FIG. 2 is a cross-sectional view of one of the surgical instruments of FIG. 1;

FIGS. 7A, 7B, 8A, 8B, 9A and 9B are views illustrating a structure of bending segments with 2 degrees of directional freedom;

FIGS. 20A and 20B are views illustrating bending of the steerable member;

FIG. 21A-21C are cross-sectional views illustrating bending of a steerable member according to a modified embodiment;

FIG. 33 is a view schematically illustrating the length of a bending actuation wire before and after bending in an ideal continuous flexible arm, wherein FIG. 33A shows the length of the bending actuation wire before bending and FIG. 33B shows the length of the bending actuation wire after bending.

FIG. 34 which is a view schematically illustrating the length of a bending actuation wire before and after bending in the actual condition, wherein FIG. 34A shows the length of the bending actuation wire before bending and FIG. 34B shows the length of the bending actuation wire after bending.

FIG. 37 illustrates pivotal motion of one of the exemplary tension-regulating member of FIG. 36, wherein

FIG. 38 is a view schematically illustrating a slack in a wire being improved according to the exemplary tension-regulating member structure in FIG. 36, wherein

FIG. 48 is a perspective view illustrating three types of the interchangeable grips according to an exemplary embodiment of the present invention wherein FIG. 48B is a tweezers-type one.

FIG. 57 is a plan view of a distal coupler of the surgical device hereof;

FIG. 58 is a sectional view of the distal coupler of FIG. 57 at 58-58;

FIG. 59 is a plan view of an intermediate coupler of the surgical device hereof;

DETAILED DESCRIPTION

Figure 1:
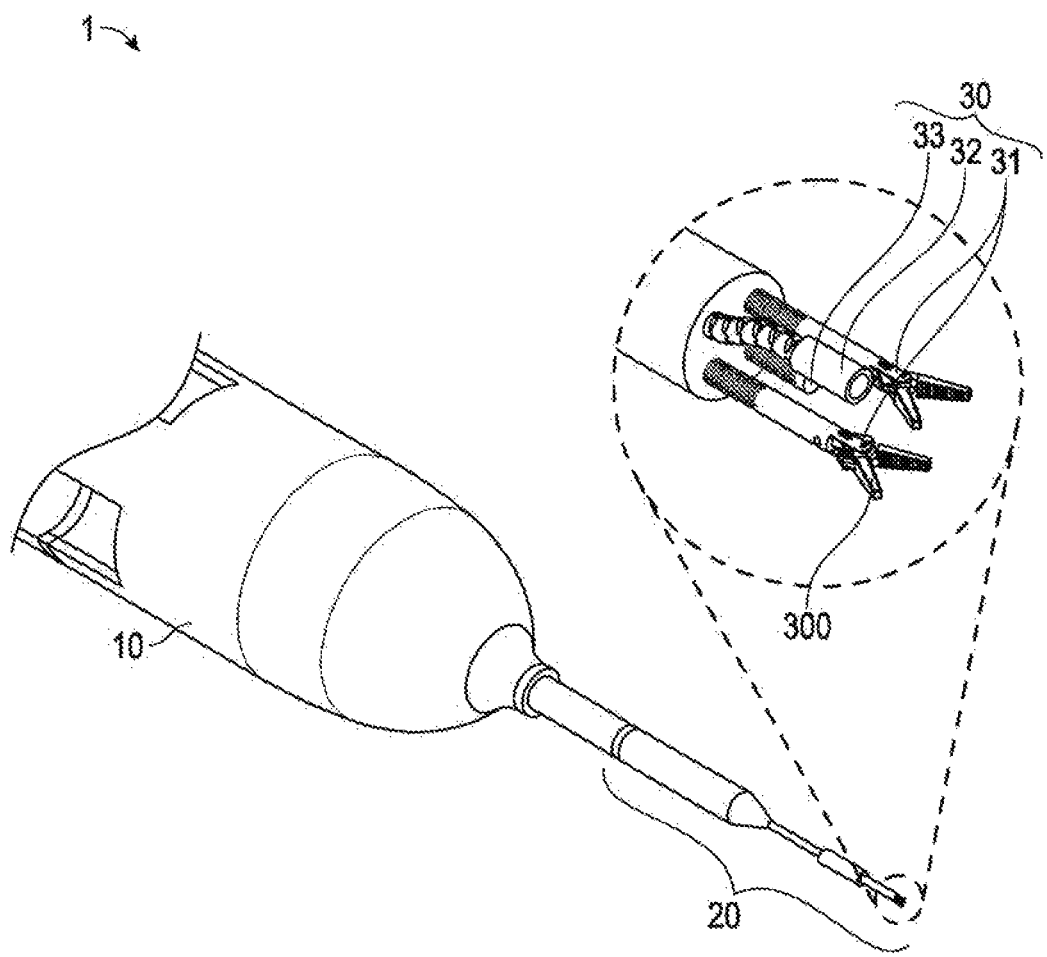
FIG. 1 is a view illustrating a surgical apparatus according to an exemplary embodiment of the present invention.

The invention and the various features and advantageous details thereof are explained more fully with reference to the non-limiting embodiments that are illustrated in the accompanying drawings and detailed in the following description.

Descriptions of well-known materials, manufacturing techniques, parts, and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

Hereinafter, a surgical apparatus according to an exemplary embodiment of the present invention will be described concretely with reference to the drawings. A description of the positional relationship between the components will now be made basically with reference to the drawings. In the drawings, structures in the embodiment may be simplified or exaggerated for clarity. Accordingly, the present invention is not limited to this exemplary embodiment, but instead various kinds of devices may be added, changed, or omitted.

As used herein, the terms subject of patient refers to the recipient of a medical intervention with the device. In certain aspects the patient is a human patient. In other aspects, the patient is a companion, sporting, domestic or livestock animal.

This exemplary embodiment will be described with respect to a surgical apparatus that has a plurality of passages extending inside an insertion part, with various kinds of surgical instruments located in each passage. However, it is to be noted that the present invention is not limited to this exemplary embodiment and is applicable to a variety of surgical apparatuses, including catheters, endoscopes, and surgical robots, that are bendable at the distal end.

FIG. 1 is a view illustrating a surgical apparatus according to an exemplary embodiment of the present invention. As illustrated in FIG. 1, a surgical apparatus 1 comprises an insertion part 20 provided at the distal end of the surgical apparatus and a manipulating part 10 located at the proximal end of the insertion part 20.

The insertion part 20 forms the portion of the surgical instrument 10 that is inserted into a surgical site during surgery. The insertion part 20 consists of a flexible, biocompatible, surrounding sheath 202 terminating in a distal coupler 1140 (see, e.g. FIG. 56), in which at least one surgical instrument 30 for use in a surgical operation is selectively located within, or extended therefrom. The surgical instrument 30 is selectively located within a hollow passage defined by the outer wall of the surrounding sheath 202. When the surgical instrument 30 is extended from the surrounding sheath 202 and distal coupler 1140, it extends outwardly of the distal coupler 1140 at the distal end 16 of the insertion part 20, and in this position is useful to perform surgery or capture images of the body lumen within which it is located. The insertion part length is shortened for ease of illustration in FIG. 1, and in an actual device may be on the order of over one meter in length.

In the embodiment of FIG. 1, the sheath 202 of the insertion part 20 of the surgical apparatus of FIG. 1 includes three surgical instruments 30 extending therethrough, and as shown in FIG. 1, extending outwardly of a coupler at the end of the sheath 202. In FIG. 1, two of the four surgical instruments include forceps 31 as the end effectors 300 thereof at the distal ends thereof. Such surgical instruments may be used by an operator, such as a surgeon or doctor, to perform various surgical operations by manipulating the forceps. Additionally, other various types of surgical elements including blades, suturing units, needles, etc. can be deployed as end effectors o the surgical instruments 300. In the embodiment, the third surgical instrument is an imaging unit 32. The imaging unit 32 includes a charge coupled device to capture images of a body lumen surface, and an illumination device such as an LED to illuminate the body lumen surface to enable the charge coupled device to capture the image of the body lumen. Alternatively, a fourth surgical instrument, such as a lumen unit 33 with a working channel in it through which various instruments can be inserted, may be extended through the sheath 202 and terminate at the coupler.

The surgical instruments 30 extending from the distal end 16 of the insertion part 20, are configured such that a pliable portion thereof can be bent or otherwise manipulated in space to direct the end of the pliable portion to face in a specific orientation with respect to the inner wall of the body lumen in which it is deployed. The bending of a portion of the surgical instruments 30 allows a surgical operation to be performed in different directions or orientations or the taking of images from different directions or orientations than the direction and orientation of the distal end 16 of the insertion part 20. Herein, the manipulation of the surgical instruments 30 to change the orientation thereof with respect to the distal end 16 of the insertion part 20 is provided by a plurality of wires extending therealong, which will be further described in detail below.

The manipulating part 10 is provided at the proximal end of the insertion part 20, and is configured to manipulate the insertion part 20 and/or the surgical instruments 30. The distal end of the manipulating part 10 is connected to the proximal end of the insertion part 20, and may be detachably connected thereto in this exemplary embodiment. At least one driving part is provided in the manipulating part 10. The driving part 40 is mechanically connected to the insertion part 20 and/or various types of wire members of the surgical instruments 30, and the driving part 40 enables various motions of the insertion part 20 and/or surgical instruments 30, including a bending movement of a portion of the surgical instruments 30. The structure and operation of the driving part will be detailed later herein.

Hereinafter, a detailed configuration of the above-described surgical apparatus will be explained in more detail with reference to the drawings.

FIG. 2 is a cross-sectional view of one of the surgical instrument of FIG. 1. As illustrated in FIG. 2, the surgical instrument 30 comprises a steerable member 100 at the distal end that is bendable at one or more locations across its length, and is likewise rotatable about the central longitudinal axis 18 of the tubular flexible member 200. The steerable member 100 has a plurality of bending segments 110 with hollow channels (not shown in this Fig.) that are serially in contact with one another. A tubular flexible member 200 comprising a flexible material extends from the driving part 40 (see, e.g. FIG. 54) and terminates at a connection with the proximal end of the steerable member 100. Each tubular flexible member 200 is configured as a hollow tube whereby a plurality of wire members extending between a connection to the distal end of the surgical instrument 30 to the driving part 40, and a further plurality steering wires extending from the driving part 40 to the steerable member 100 and back to the driving part 40 extend. In FIG. 2 an end effector 300 is provided at the distal end of the steerable member 100, and the end effector 300 is selectively actuated by an end effector actuation wire 500 as will be detailed later herein.

Each bending segment 110 of the steerable member 100 is connected to adjacent bending segments 110 in a way that allows angular motion therebetween under the control of bending actuation wires 400. The bending actuation wires 400 are located in such a way as to pass through the steerable member 100 and the tubular flexible member 200, and the distal ends of the bending actuation wires 400 are connected to the steerable member 100, and their proximal ends extend through individual conduits extending through the length of the flexible member where they are connected to the driving portion 40. Each bending segment 110 comprises a plurality of lumens 112 that are formed lengthwise, whereby the bending actuation wires 400 are located within, and may extend through, the lumens 112 (FIG. 5A). Accordingly, when the bending actuation wires 400 are moved by the manipulating part 10, the plurality of bending segments 110 move hingedly, thus causing the steerable member 100 to bend.

FIG. 3 is a view schematically illustrating slack formed in a wire due to bending of the steerable member by movement of the wire(s) 400. Let each of the bending segments 110 have a length of L and a width of 2r. Adjacent bending segments 110 are hinged at the middle on their facing sides (which is at a distance of r from the outer perimeter). Let the bending actuation wires 400 be located on the two opposed sides of the width of each bending segment and pass over the sides of each bending segment (which is at a distance of L from each hinged portion).

Figure 3B:
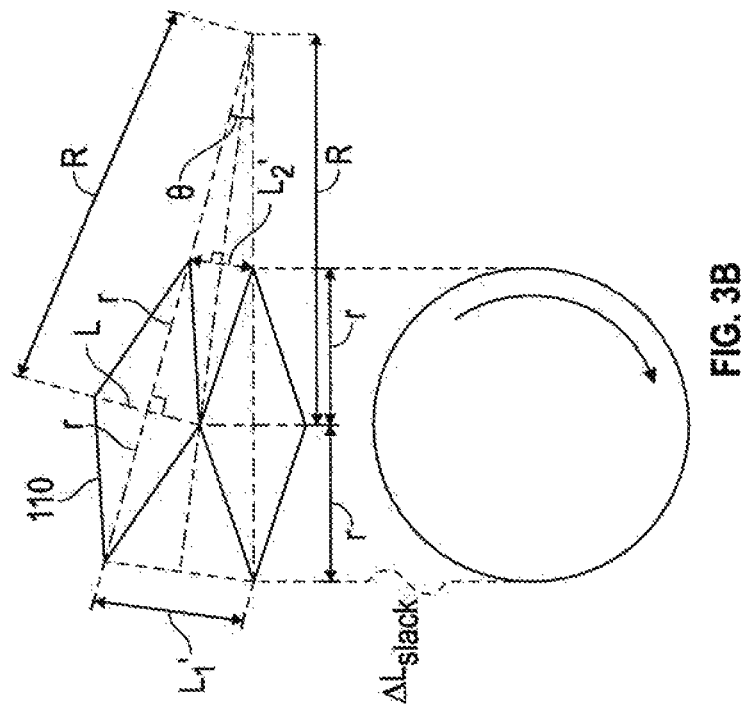
FIGS. 3A, 3B and 4 are views schematically illustrating a slack in a wire due to bending of a steerable member.
Figure 3A:
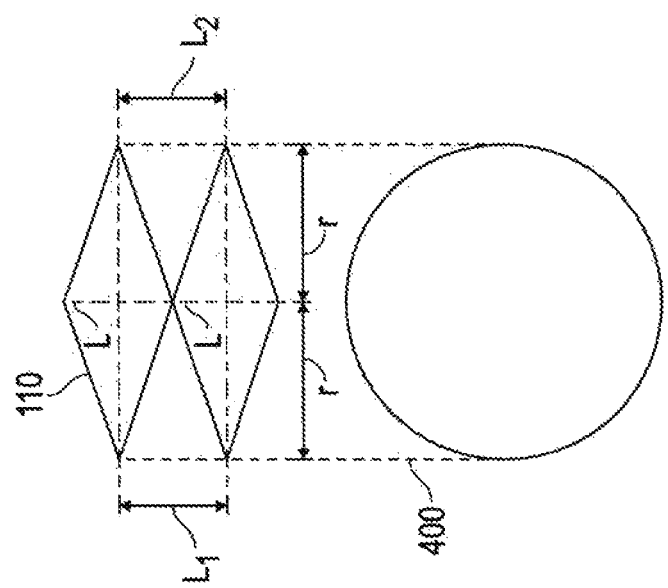

FIG. 3A illustrates two segments of the steerable member before relative bending movement therebetween, and FIG. 3B illustrates the two segments of the steerable member when bent to a radius of curvature R. The wire 400 is connected to the most distal segment of the steerable member on a first side thereof, passes therefrom through the tubular flexible member 200 to the drive unit where it is wrapped around a pulley, and thence the remaining length of the wire extends back through the tubular flexible member 200 and connects to the opposite side of the most distal segment of the tubular flexible member 200. In FIG. 3B, the angle of bend between two bending segments 110 is denoted by θ. The following equation compares the sum of the lengths of the two wire portions between the two bending segments before bending and the sum of the lengths of the two wire portions after bending. If the lengths of the two wire portions before bending are denoted by L1 and L2, respectively, and the lengths of the two wire portions after bending are denoted by L1' and L2', respectively, the difference ΔL between the two lengths is as follows:

$$L_1 = L_2 = L = 2R\tan\left(\frac{\theta}{2}\right)$$

$$L'_1 + L'_2 = 2(R+r)\sin\left(\frac{\theta}{2}\right) + 2(R-r)\sin\left(\frac{\theta}{2}\right) = 4R\sin\left(\frac{\theta}{2}\right)$$

$$\Delta L = L_1 + L_2 - L'_1 - L'_2 = 4R\left(\tan\left(\frac{\theta}{2}\right) - \sin\left(\frac{\theta}{2}\right)\right)$$

As seen from the equations above, the sum of the lengths of the two wire portions between the two bending segments after bending is smaller than that before bending. Accordingly, when the wires on both sides are manipulated in conjunction with each other, a slack of ΔL is produced between each bending segment. This is because, when bending occurs, the amount of change ($L_1'-L_1$) in the length of the wire on the other side of the center of curvature is smaller than the amount of change ($L_2-L_2'$) in the length of the wire near the center of curvature. Accordingly, backlash is created due to bending, thus making fine adjustment difficult.

Figure 4:
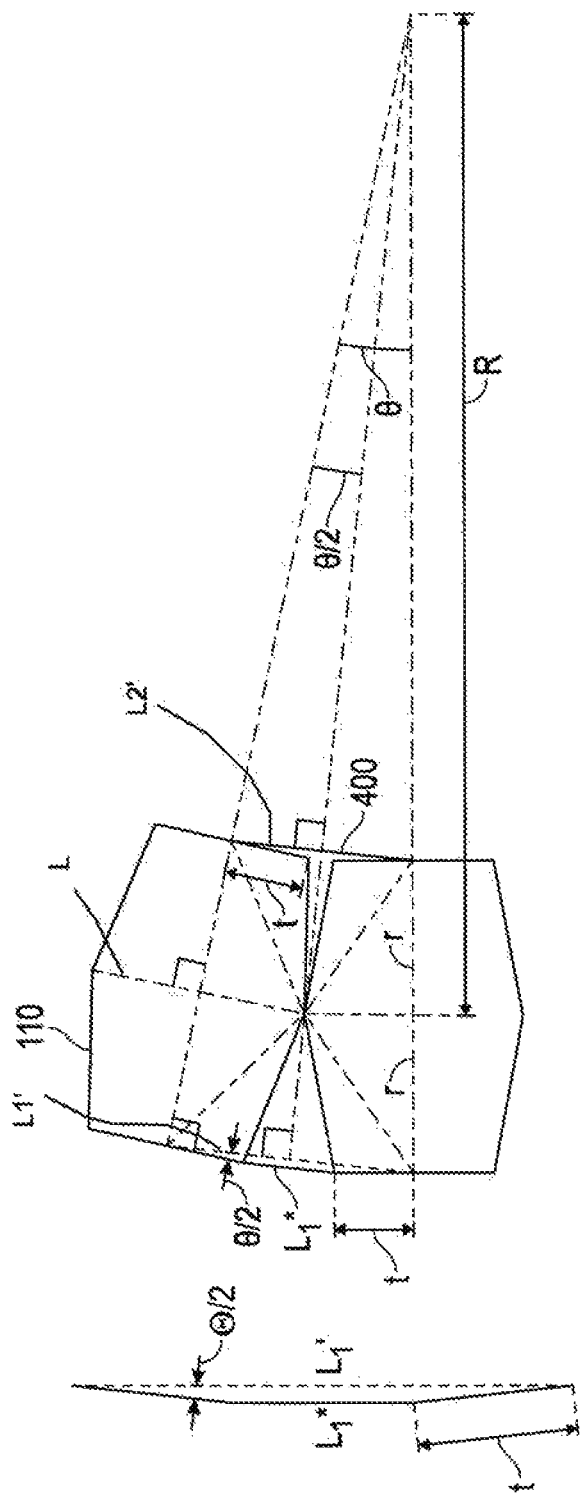

In contrast, in this exemplary embodiment, the bending segments may be configured in various shapes to minimize the slack caused by bending. FIG. 4 is a view schematically illustrating a slack in a wire according to an improved bending segment structure. As illustrated in FIG. 4, the improved bending segments 110 are configured in such a way that part of the lumens 112 where the bending actuation wires are located is open (see FIG. 5). Herein, t denotes the length of an open lumen portion. While the wire near the center of curvature has the shorter path due to the open lumen portion, the wire on the other side of the center of curvature has a path to which an extra length is added at the corresponding open lumen portion. In this case, the path $L_2^*$ of the wire near the center of curvature is equal in length to the previous path ($L_2'$ of FIG. 3), and the path $L1^*$ of the wire on the other side of the center of curvature is longer than the previous path ($L_1'$ of FIG. 3). This increase in path length is because a sidewall of the open lumen portion (near the center of the bending segments) on the other side of the center of curvature forms a stumbling portion 114 and the bending actuation wire 400 passing through the path stumbles against the stumbling portion 114 (see FIG. 5). Accordingly, when bending occurs using the improved bending segments, ΔL is as follows:

$$L_1 = L_2 = L = 2R\tan\left(\frac{\theta}{2}\right)$$

$$L_1^* = L'_1 - 2t\cos\left(\frac{\theta}{2}\right) + 2t = L'_1 + 2t\left(1 - \cos\left(\frac{\theta}{2}\right)\right)$$

$$L_1^* + L'_2 = 2(R+r)\sin\left(\frac{\theta}{2}\right) + 2(R-r)\sin\left(\frac{\theta}{2}\right) + 2t\left(1 - \cos\left(\frac{\theta}{2}\right)\right) =$$

$$4R\sin\left(\frac{\theta}{2}\right) + 2t\left(1 - \cos\left(\frac{\theta}{2}\right)\right)$$

$$\Delta L = L_1 + L_2 - L_1^* - L'_2 = 4R\left(\tan\left(\frac{\theta}{2}\right) - \sin\left(\frac{\theta}{2}\right)\right) - 2t\left(1 - \cos\left(\frac{\theta}{2}\right)\right)$$

As stated above, with the improved bending segments 110 configured to reduce the length ΔL of the slack, the movement of the surgical apparatus 1 can be finely controlled. Generally, the length t of the open lumen portions may be 10% or more of the length L of the bending segments. Although the amount of reduction in the length ΔL of the slack differs depending on the dimension, angle of bend, etc. of the bending segments, the length ΔL of the slack may be reduced by approximately 30% or more.

The improved bending segments may be designed in various ways. Hereinafter, various exemplary embodiments of the bending segments will be described in detail with reference to FIGS. 5 to 11.

FIG. 5 is a view illustrating a structure of bending segments with 1 degree of freedom. The bending segments 110 shown in FIG. 5 have a body with hollow channels 111 formed within them. One pair of connecting parts 120 is provided on one end of the length of the body and other one pair of connecting parts 120 is provided on the opposite end. Each pair of connecting parts 120 is located facing each other on two opposite sides of the width of the body, with a hollow channel 111 midway between them.

Each bending segment 110 is hinged to adjacent bending segments, and in this embodiment they are interconnected by the connecting parts thereof coupled to adjacent bending segment(s). In FIG. 5, the connecting parts 120 are connected by pinning them together. However, the connecting parts 120 need not be physically constrained with respect to each other such as by hinge shafts, and can move with respect to each other about a hinge axis. As the hinge shafts of the connecting parts 120 all have the same orientation, i.e., they are parallel to one another, the steerable member of FIG. 5 has 1 degree of freedom at which it bends to the left or right (as shown in the drawing). To enable locating and orienting the distal end of the steerable member 100 to face portions of the body lumen over 360 degrees therearound, the tubular flexible member 200 is rotatable about its longitudinal axis 18 by the driving part 40, which, when the steerable member 100 is facing the side wall of the lumen, allows an operator to circumferentially move the direction which the distal end of the steerable member is facing around the inner wall of the body lumen.

Each bending segment 110 includes a pair of lumens 112 in which the bending actuation wires are located. The pair of lumens 112 are formed through openings extending through the wall surface of a hollow body generally parallel to the center of a cross-section of the bending segment 110, and they are arranged symmetrically about the center of a cross-section of the bending segment 110, and thus spaced a predetermined distance from each other.

Figure 5B:
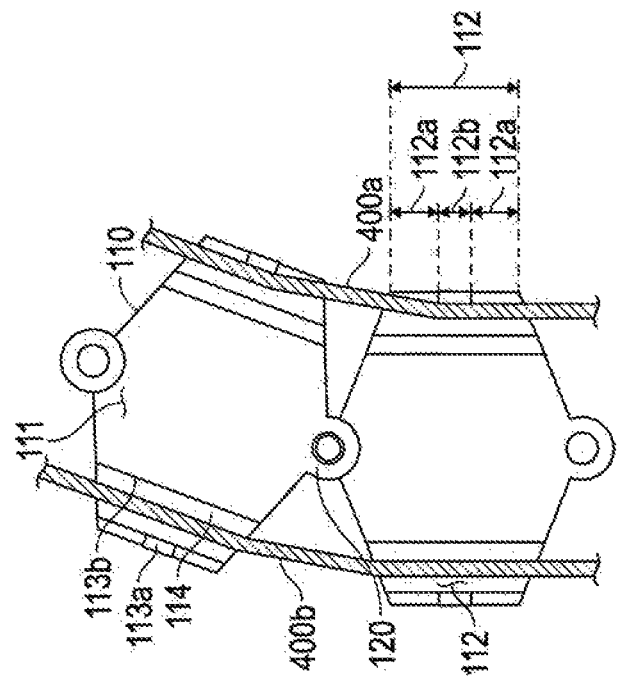
FIGS. 5A, 5B, 6A and 6B are views illustrating a structure of bending segments with 1 degree of directional freedom.
Figure 5A:
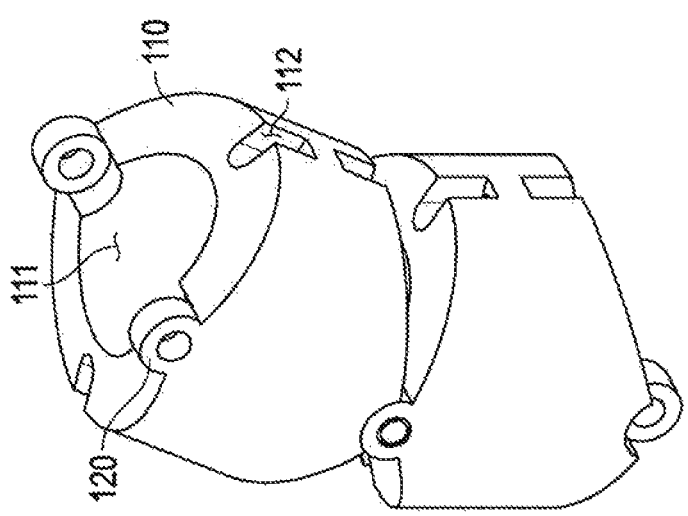

As shown in FIGS. 5A and 5B, the lumens of the bending segments 110 are partially open. Specifically, each lumen comprises a closed lumen portion 112b opening at either end thereof into an open lumen portion 112a. In the closed lumen portion 112b, the lumen walls are enclosed by wall surfaces as shown in FIG. 5B, so that the bending actuation wire is constrained within the closed lumen portion 112b due to this enclosed structure. In contrast, in the open lumen portion 112a, at least part of the wall thereof has an open structure. Accordingly, the bending actuation wire located in the open lumen portion 112a can movable outwardly of the lumen at this open portion.

In this exemplary embodiment, the open lumen portions 112a have a structure in which the portion of the wall 113a on the outer side of the bending segment (which is on the opposite side of the center of a cross-section of the bending segment) is open. Accordingly, when relative arcuate movement of the bending segments occurs, the wire 400a near the center of curvature of the resulting bent steerable member moves toward an outer portion (outward direction) of the open lumen portion, which enables the bending segments to be connected on a shorter length, as compared with a bending segment wherein the lumen is closed over the length or height of the bending segment. In the lumen 112 on the opposite side of the bending segment 110, the wire 400b is pulled against the portion of the wall 113b of the open lumen portion closest to the center of the cross-section of the bending segment, which forms a stumbling portion 114 against which a wire stumbles, i.e., friction between the wire 400b and the and wall 113b of the open lumen causes the wire 400b to at least momentarily bind against the wall 113b. Accordingly, when bending occurs, the wire 400b on the other side of the center of curvature has a greater contact area with the inner wall of the lumen 112, thereby reducing the length of the slack.

In FIGS. 5A and 5B, each lumen 112 of the bending segments 110 is shown configured in such a way that a closed lumen portion 112b is formed at the middle of the lumen length and an open lumen portion 112a is located on either side of the closed lumen portion 112b. This is merely an example, and one side of the lumen 112 along the length may form an open lumen portion and the other side may form a closed lumen portion. Alternatively, the open lumen portions of a pair of adjacent bending segments may be arranged symmetrically with respect to the hinge shafts. In this way, the lumens where the bending actuation wires are located may be variously altered in such a way that a wall surface (inner wall surface) 113b near the center of a cross-section of the bending segments is longer than a wall surface (outer wall surface) 113a on the other side of the center of the cross-section thereof.

Although FIGS. 5A and 5B illustrate the open lumen portion 112a as longer than the closed lumen portion 112b, the present invention is not limited thereto and may have various configurations depending on the structure of the bending segments and the maximum angle of the arcuate movement between adjacent bending segments. It should be noted that the length of the open lumen portion occupying 20% or more of the entire lumen length may be advantageous to reducing the length of the slack.

Figure 6B:
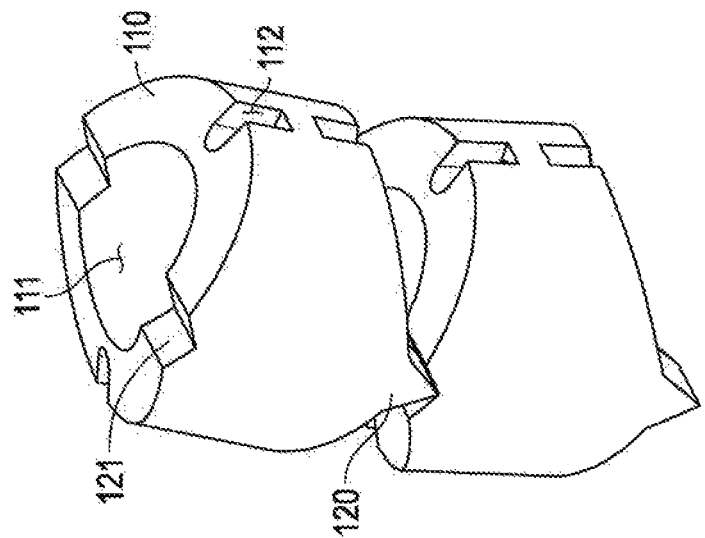
Figure 6A:
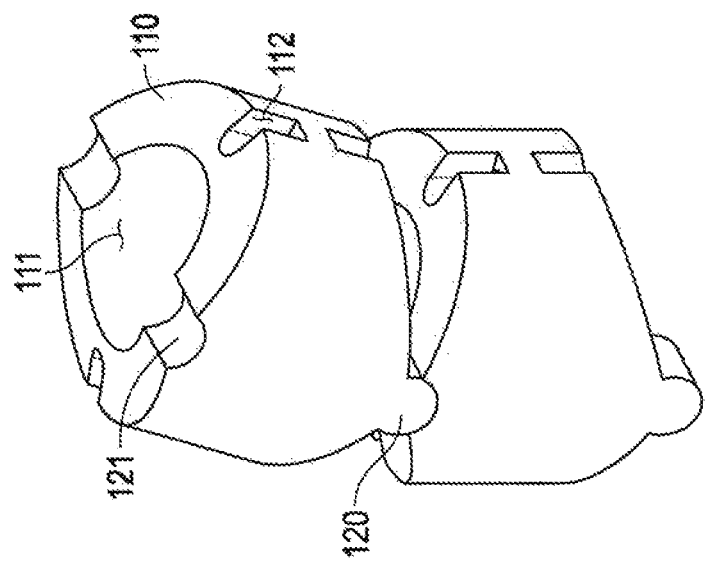

The connecting parts of the bending segments can be formed in various ways, other than pinning the connecting parts together as shown in FIG. 5. FIG. 6 illustrates an example of a different type of connection between adjacent bending segments.

The bending segments of FIG. 6 each include a pair of connecting parts 120 on one end thereof and a pair of recess parts 121 on the opposed end thereof. The connecting parts 120 of a bending segment 110 are accommodated in the recess parts 121 of an adjacent bending segment to form a free hinge connection. The connection is a free hinge connection, because the segments are not pinned or otherwise physically constrained to prevent movement thereof away from each other. The connecting parts 120 of A of FIG. 6 each consist of a protrusion with a convex round surface, and the recess parts 121 each have a matching concave rounded recess which accommodates a corresponding protrusion.

Accordingly, each connecting part 120 can slide along the surface of a corresponding recess part 121, such that the centerlines of adjacent bending segments are moveable angularly with respect to each other. The connecting parts 120 of FIG. 6B each consist of a v-shaped protrusion terminating in a linear edge, and the recess parts 121 each have a v-shaped notch-like groove, but the angle between the opposed flanks of the v shaped protrusion is less than that between the flanks of the v-shaped notch, and hence when the linear edge of the v-shaped protrusion is seated on the base of the v-shaped notch, there is clearance or free space on either side of the protrusion, and the protrusion, and thus the centerlines of adjacent bending segments are moveable angularly with respect to each other.

FIG. 7 is a view illustrating a structure of bending segments with 2 degrees of freedom. The bending segments of FIG. 7 each are connected to adjacent bending segments in a way that allows relative angular movement therebetween, and each is configured in such a way that a one of a first axis or a hinge shaft h1 connected to a bending segment on one end of the bending and a hinge shaft h2 connected to a bending segment on the other end of the bending segment have different orientations, specifically, approximately ninety degrees offset form each other. Accordingly, the bending segments 100 of FIG. 7 constitute a steerable member that is movable at 2 or more degrees of freedom, unlike those described with respect to FIGS. 5 and 6.

Specifically, each bending segment 110 of FIG. 7 includes a pair of connecting parts 120 on one end of the bending segment 110 and a pair of recess parts 121 on the opposite end of the bending segment 110. Each pair of connecting parts 120 faces a pair of recesses 120. As is the case in FIGS.

5A and 5B, the connecting parts 120 each bending segment 110 consist of a convex protrusion with a round surface, and the recesses are as convex recesses of a matching rounded contour to accommodate the convex protrusion of an adjacent bending segment 110.

Figures 7A, 7B:
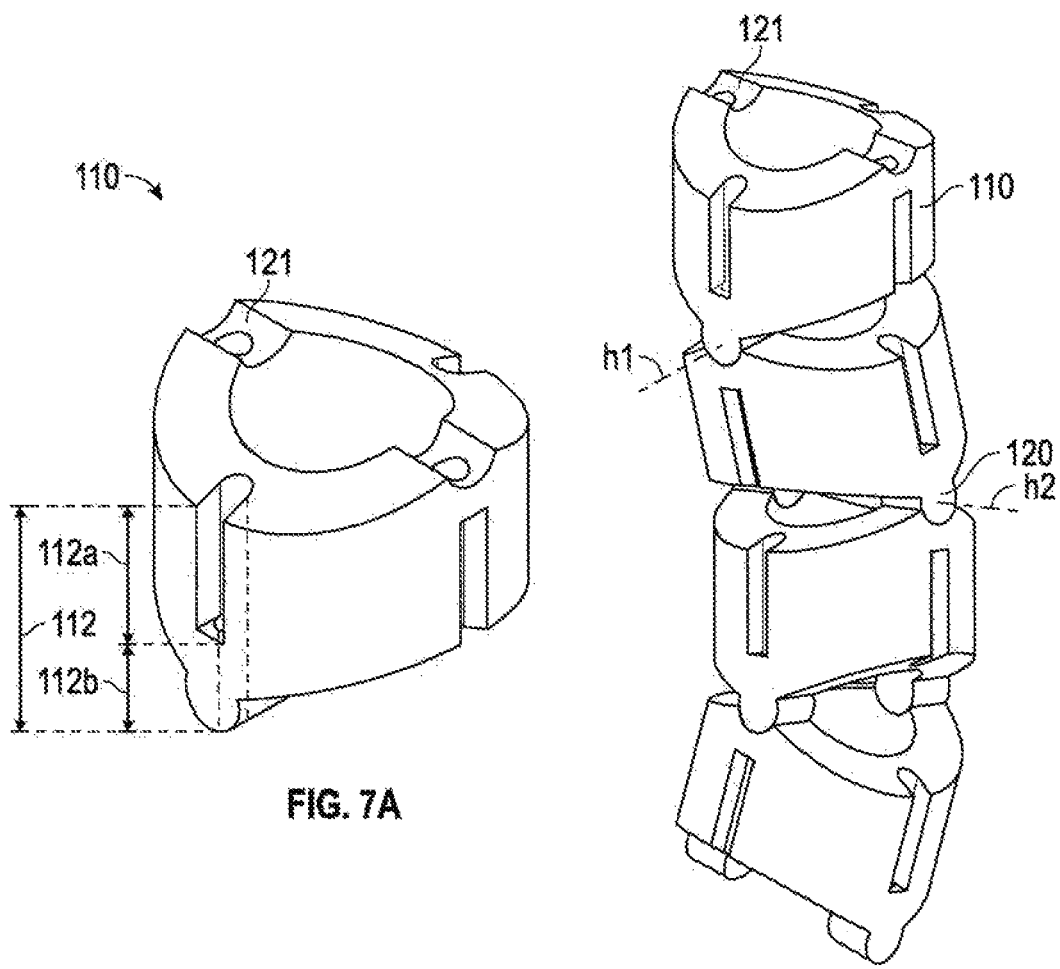

As illustrated in FIG. 7B, in each bending segment 110, an axis that extends through the center of the rounded portion of the pair of connecting parts 120 and an axis that extends through the center of the rounded surface of the recesses 121 are orthogonal to each other. That is, the pair of connecting parts and the pair of recesses are positioned at different locations with respect to a cross-section of the bending segment 110 (more specifically, axes extending through the centers of the pair of connecting parts and the pair of recesses cross at 90 degrees).

Hence, the bending segment 110 moves hingedly with respect to an adjacent segment on one side on one of a first axis or a hinge shaft h1 and with respect to an adjacent segment on the opposite end of the bending segment 110 on a second axis h2. That is, the connecting parts of the bending segments are configured in such a way that the orientations of the axes of the first hinge shaft and the second hinge shaft are arranged in an alternating fashion orthogonal to one another. Accordingly, the bending segments 110 of FIG. 7 move in one degree of freedom with respect to each adjacent bending segment 110, but the orientation of the steerable member 100 formed of the plurality of bending segments 110 is configurable in two degrees of freedom.

In this embodiment of the steerable member 100, each bending segment 110 comprises four lumens 112 that are formed along the length, between the opposed ends thereof. As illustrated in FIGS. 7A and 7B, each lumen 112 extends inwardly of the outer wall of the bending segment to form a connecting part 120 and a recess part 121. One of each of the four lumens 112 is aligned with the locations where the connecting parts and the recesses are formed, spaced at 90-degree intervals around the body.

A bending actuation wire 400 is located in each of the four lumens 112, respectively. Among these actuation wires 400, one pair of wires induces bending of one shaft of the steerable member 100, and the other pair of wires induces bending of the other shaft.

Each lumen is partially open, as is with the aforementioned example. As illustrated in FIG. 7A, a portion of each lumen 112 extending inwardly of, and generally parallel to, an outer wall of a bending segment 110 includes a closed lumen portion 112b extending through a projecting part 120 and an open lumen portion 112a extending therefrom to the opposite end of the bending segment 110 where a connecting part 120 or recess 121 is not present, and at a lumen offset ninety degrees therefrom, a closed lumen portion 112b extending through a recess 121 and an open lumen portion 112a extending therefrom to the opposite end of the connecting portion 110 where a connecting part 120 or recess 121 is not present.

Although FIG. 7 illustrates that the lumen 112 extends through a connecting part 120 or recess 121, the lumens 112 may be offset from the connecting parts 120 and recesses 121. In the embodiment, the connecting parts 120 and recesses 121 are spaced at 90-degree intervals around the lateral side of the body (e.g., along the circumference) of each bending segment 110. Each lumen 112 is thus located between two adjacent connecting parts 120 and two adjacent recesses 121, preferably at a location 45 degrees from the connecting part 120 and the recess 121.

In this case, as illustrated in FIG. 8, each lumen 112 may be configured in such a way that a closed lumen portion 112b is formed at the middle of the length of the lumen extending between opposed ends of the bending segment and an open lumen portion 112a is formed on either side of the closed lumen portion 112b.

FIGS. 7 and 8 have been explained with respect to a connecting part 120 consisting of a protrusion with a round surface and a recess 121 accommodating the connecting part 120. However, this is merely an example, and as shown in B of FIG. 6, the connecting part may consist of a protrusion with a linear edge and the recess may be a v-shaped notch-like groove (see FIGS. 9A and 9B). Otherwise, as shown in FIG. 5, two connecting parts may be pinned together in a way that allows a hinge like movement, rather than each comprising a connecting part and a recess.

The exemplary embodiments shown in FIGS. 7 to 9 provide a connecting structure to allow relative arcuate positioning of adjacent bending segments, in which a pair of connecting parts is provided on one bending segment and a pair of recesses are provided on another bending segment. Alternatively, one connecting part and one recess may be located on one end of one bending segment spaced apart by the hollow portion of the bending segment extending between them, and the connecting part and recess of an adjacent bending segment are located reversed to those of the first bending segment, to provide the connection between the adjacent bending segments 110.

Figure 10:
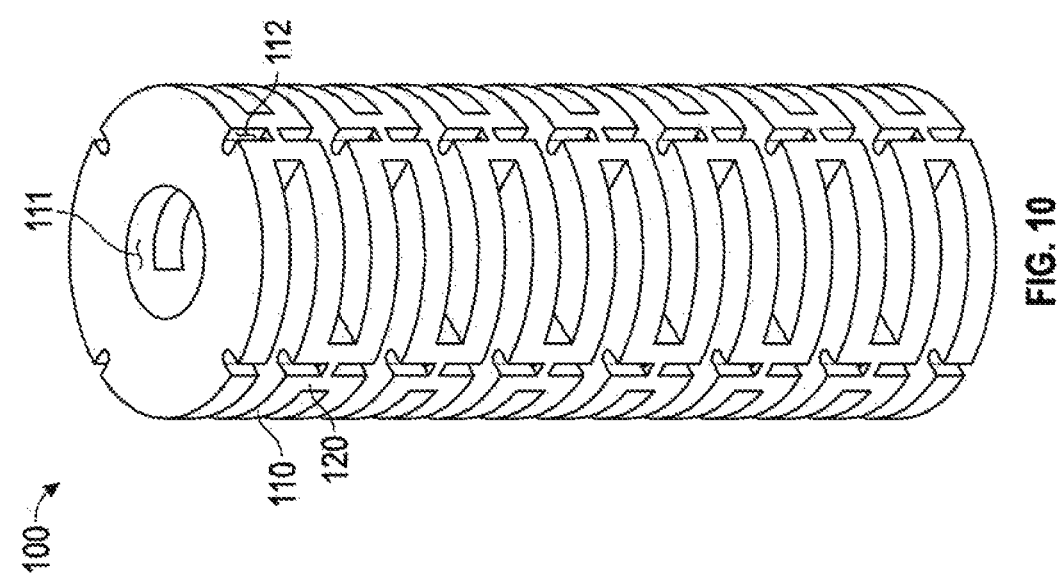

FIG. 10 illustrates an alternative construct of a steerable member, employing a continuous flexible hinge structure. As illustrated in FIG. 10, the bending segments 110 are in the shape of a disc-like plate, and connected by flexible connecting parts 120 situated between the bending segments 110. While the steerable member of FIGS. 5 to 9 can be bent using the mechanical hinge structure of the connecting parts, the steerable member of FIG. 10 can be bent using the elasticity of the connecting parts.

More specifically, the steerable member of FIG. 10 consists of a plurality of bending segments 110 formed integrally with one another and a plurality of connecting parts 120. For example, it may be manufactured by a molding method using a flexible plastic resin. As illustrated in FIG. 10, each bending segment 110 and each connecting part 120 have a hollow channel 111 extending therein from end to end. The connecting parts 120 are provided between each bending segment 110, and have a wall structure that extends in an outer radial direction from two opposite sides of the hollow channel. A connecting part 120 (wall structure) is arranged in a direction perpendicular to the direction in which an adjacent connecting part is arranged. Accordingly, the steerable member of FIG. 10 is bendable with 2 degrees of freedom.

Four lumens 112 along which bending actuation wires 400 are located are arranged at 90-degree intervals. Each lumen 112 is formed at a point where it penetrates the outer edge of a connecting part 120. In this instance, as in the foregoing exemplary embodiment, each lumen 112 is a partially open lumen portion 112. As illustrated in FIG. 12, the closed lumen portion 112b of each lumen is formed at a point where it penetrates the connecting part and the open lumen portion 112a thereof is formed on either side of the closed lumen portion 112b where the bending segment is penetrated. Accordingly, the steerable member 100 of this exemplary embodiment may be bent through the connecting parts 120 as the bending actuation wires 400 move.

Figure 11:
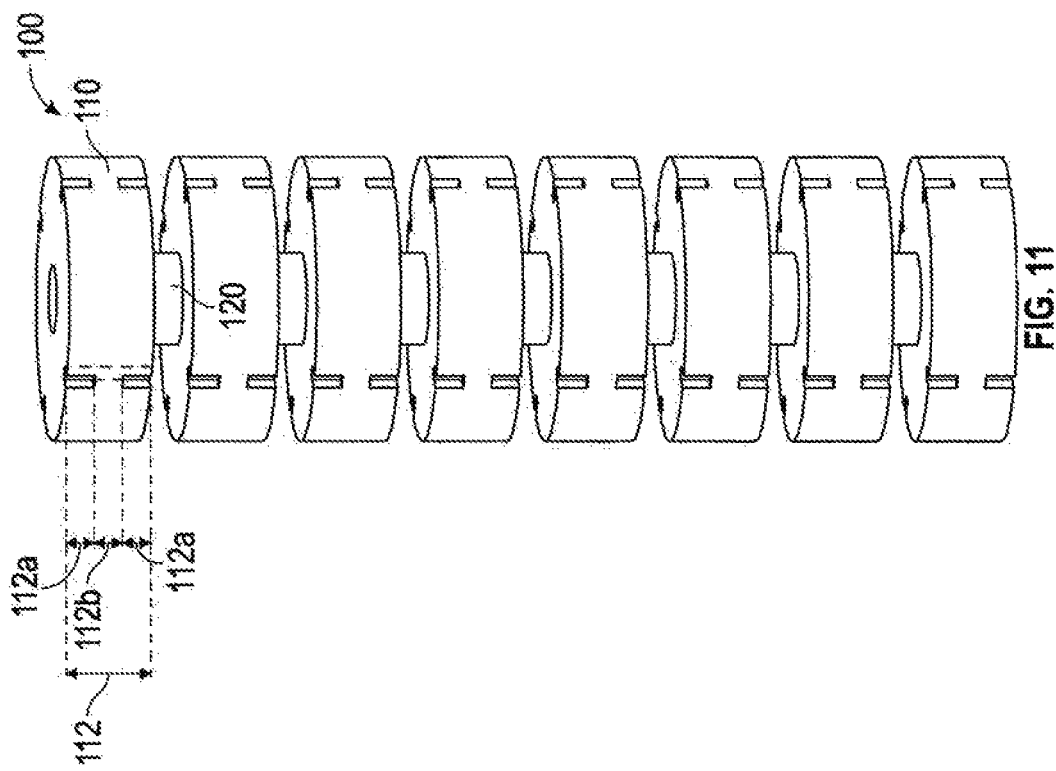
FIGS. 10 and 11 are views illustrating a steerable member using a flexible hinge structure and a steerable member using a flexible backbone structure.

FIG. 11 illustrates a steerable member using a flexible central backbone structure. The steerable member 100 of FIG. 11 comprises bending segments 110 each consisting of a disc-like plate and connecting parts 120 using a backbone structure for connecting the centers of the bending segments. The connecting parts 120 may consist of individual members provided between each bending segment, or may consist of a single member that penetrates through a plurality of bending segments. In this case, the connecting parts 120 comprise a flexible material, which bends when the bending actuation wires 400 move.

The steerable member of FIG. 11 also includes four lumens 112, and each lumen is partially open. Specifically, the lumen 112 may include a closed lumen portion 112b formed at the middle part of the length of the lumen and an open lumen portion 112a formed on either side of the closed lumen portion 112b.

In the exemplary embodiments set forth above, bending segments capable of minimizing slack are used to prevent backlash caused by bending. The steerable member may be configured in other various ways in order to prevent backlash.

FIGS. 12 to 14 are views illustrating a steerable member with a lateral supporting member 130. The lateral supporting member 130 comprises an elastic material or super-elastic material, which exerts a restoration force to return the steerable member 100 to its original shape after its shape has been deviated from the original shape, for example, a generally straight line shape. This steerable member 100 includes at least one lateral supporting member 130 within it, which is configured with sufficient elastic strength and energy storage capacity to restore the lateral supporting member 130 to the initial orientation after it has been bent, and the force causing it to bend has been removed.

Figure 12A:
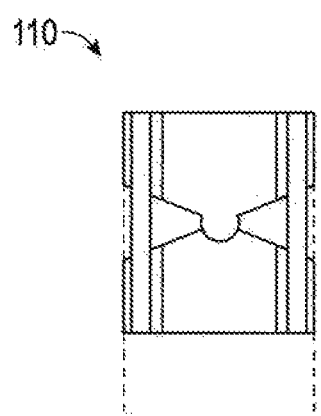
FIGS. 12A-12C, 13A-13E and 14A-14C are views illustrating a steerable member with a lateral supporting member.
Figure 12B:
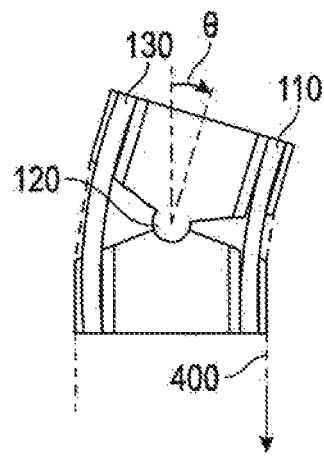
Figure 12C:
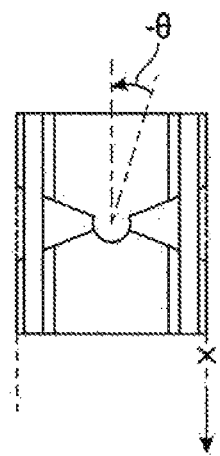

FIGS. 12A to C illustrate the bending properties provided by the lateral supporting member. As illustrated in FIG. 12, if at least one bending actuation wire 400 is pulled in the direction of the arrow in FIG. 12B by the driving part 40, the steerable member 100 bends. In this case, the steerable member 100 comprises at least one lateral supporting member 130, and the bending actuation wire 400 is manipulated to cause bending by overcoming the stiffness of the lateral supporting member 130 (FIG. 12 B). Afterwards, when the corresponding bending actuation wire 400 is released, i.e., is no longer being pulled in the direction of the driving part 40 (FIG. 12C), the steerable member 100 returns to its original orientation as a result of the lateral supporting member 130 regaining its original orientation.

Conventionally, while the bending actuation wire on one side is manipulated to bend the steerable member 100 in one direction, the bending actuation wire on the other side is manipulated to return the steerable member 100 to its original, neutral, orientation. Accordingly, slack occurs in the wire being pulled to return the steerable member 100 to its original, neutral, orientation as the steerable member 100 is restored to its original orientation faster than the wire restoring the orientation can be retracted or pulled, causing backlash. However, with the use of the lateral supporting member 130 as shown in FIG. 12, the backlash caused by the slack in the bending actuation wire may not be a problem during the bending.

Figure 13A:
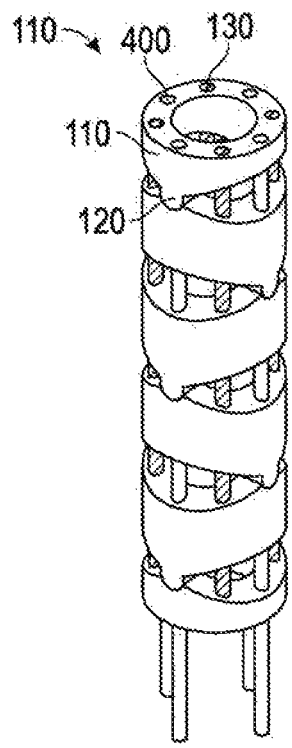
Figure 13B:
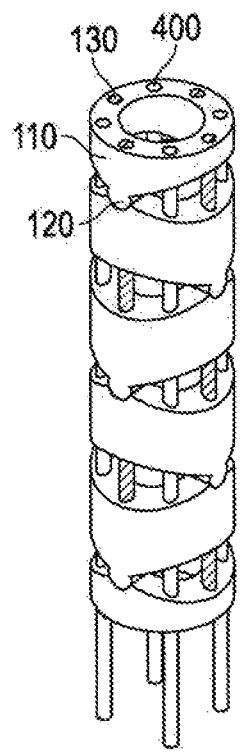
Figure 13C:
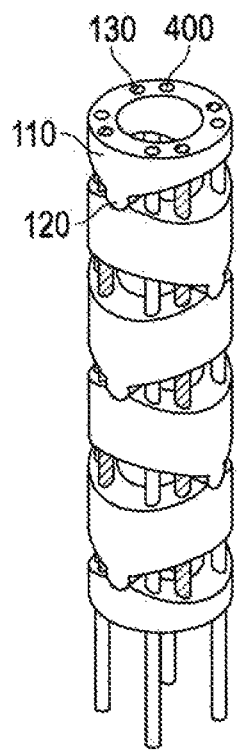

FIGS. 13A to C illustrate various exemplary embodiments of a steerable member using lateral supporting members. As illustrated in FIG. 13, the steerable member 100 may comprise a plurality of bending actuation wires 400 and a plurality of lateral supporting members 130. The lateral supporting members 130 may be configured in various types of structures, such as a wire structure or a hollow tube structure, that function as linear springs. The bending segments 110 of the steerable member 100 are configured to move with respect to each other with 2 degrees of freedom, and may include a plurality of lumens 112 through which the bending actuation wires 400 and the lateral supporting members 130 pass.

In FIGS. 13A to C, a plurality of bending actuation wires 400 and a plurality of lateral supporting members 130 are arranged with a space therebetween. In FIGS. 13A and B, four bending actuation wires 400 are arranged at 90-degree intervals around the body of the bending segments 110, and four lateral supporting members 130 are arranged at 45-degree intervals between each bending actuation wire 400. In this case, as shown in FIG. 13A, the four bending actuation wires 400 are arranged to pass through the connecting parts 120 of the bending segments 110, and as shown in FIG. 13B, the four lateral supporting members 130 are alternatively arranged to pass through the connecting parts 120 of the bending segments 110. Alternatively, as shown in FIG. 13C, pairs of a bending actuation wire 400 and a lateral supporting member 130 are arranged as pairs between each connecting part location along the circumference, and thus do not pass through the connecting parts 120 of the bending segments 110.

Figure 13D:
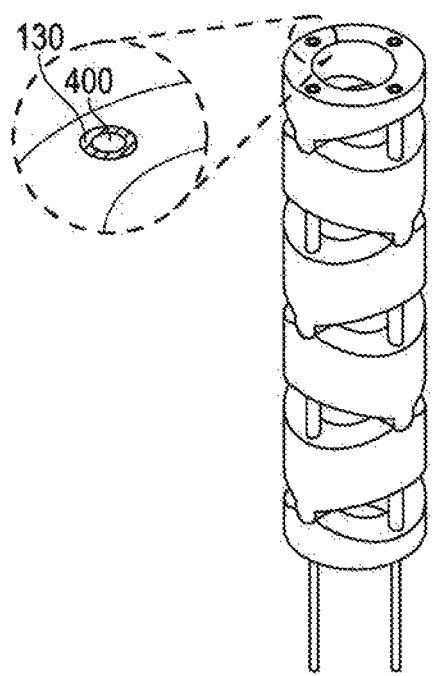
Figure 13E:
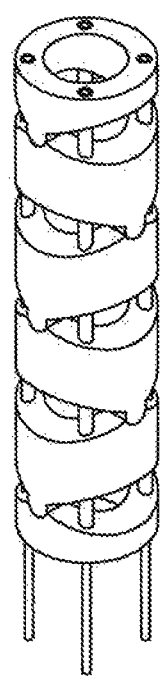

In FIGS. 13D and E, the lateral supporting members 130 have a hollow tube structure, and the bending actuation wires 400 are located inside respective ones of the lateral supporting members. The lateral supporting members 130 and the bending actuation wires 400 are arranged at 90-degree intervals around the body of the bending segments 110. In FIG. 13D, the lateral supporting members 130 and the bending actuation wires 400 are arranged to pass through the connecting parts of the bending segments. In FIG. 13E, the lateral supporting members 130 and the bending actuation wires 400 are located between each connecting part location so as not to pass through the connecting parts.

FIG. 14 illustrates properties provided by a pre-shaped lateral supporting member. The lateral supporting members of FIGS. 12 and 13 have a shape corresponding to the neutral position of the steerable member where a wire is not pulling thereon. Accordingly, the steerable member is configured to be bent with the bending actuation wires and to return to neutral by the lateral supporting members. In contrast, the lateral supporting member 130 of FIG. 14 is configured to have a bent shape in one direction so that the elasticity of the lateral supporting member 130 contributes to bending of the steerable member to one side.

Figures 14A, 14B, 14C:
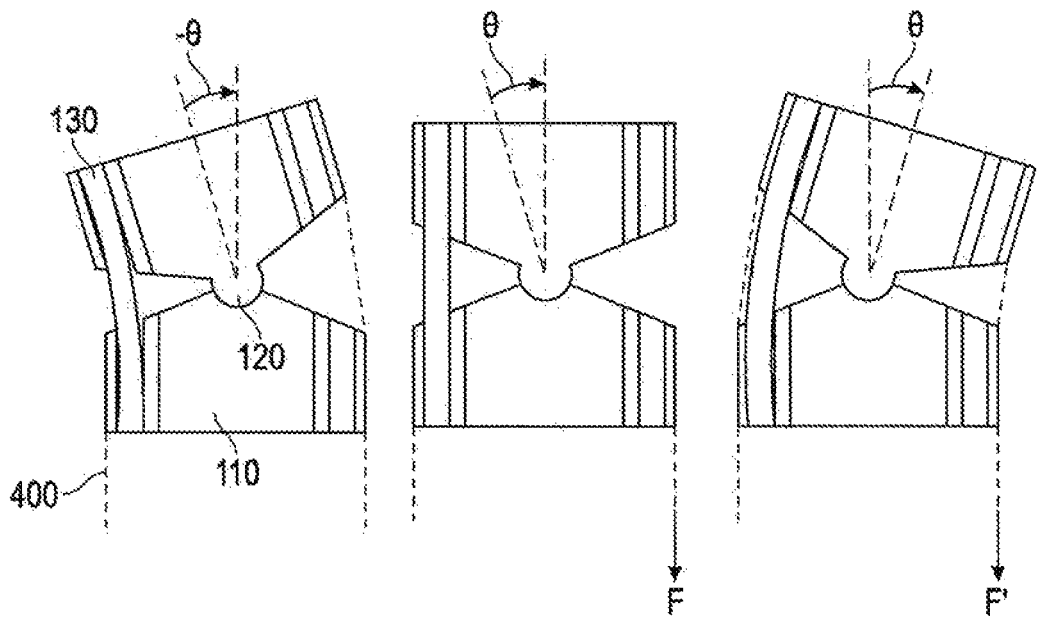

In an example, the lateral supporting member 130 of FIG. 14 is pre-shaped to bend the steerable member 100 to the left. The steerable member with the lateral supporting member 130 in it remains bent to the left without any manipulation of the actuation wire (FIG. 14A). Where the bending actuation wire 400 on the opposite side of the bending segments 110 is pulled downwardly with a first tensile force F, the steerable member 100 can be placed reorientation into a straight line orientation (FIG. 14B). Here, first tensile force F is sufficient to be in equilibrium with a moment created by the stiffness of the lateral supporting member 130. If the bending actuation wire 400 is pulled with a greater, second tensile force F', the steerable member is bent to the right (FIG. 14C). In this case, if the tensile force exerted on the bending actuation wire 400 is reduced to the first tensile force F, the steerable member 100 moves to the position thereof in FIG. 14B, and if the tensile force exerted on the bending actuation wires 400 is completely released, the steerable member 100 bends to the left (FIG. 14A).

In this instance, the steerable member moves to the straight line position or the initial bent position as a result of the stiffness of the lateral supporting member 130, thereby enabling bending control of the steerable member 100 without wire backlash. Although FIG. 14 depicts a bending mechanism that has 1 degree of freedom using a pre-shaped lateral supporting member and bending actuation wires, a variety of bending mechanisms using pre-shaped lateral supporting members may be employed.

Figures 15A, 15B:
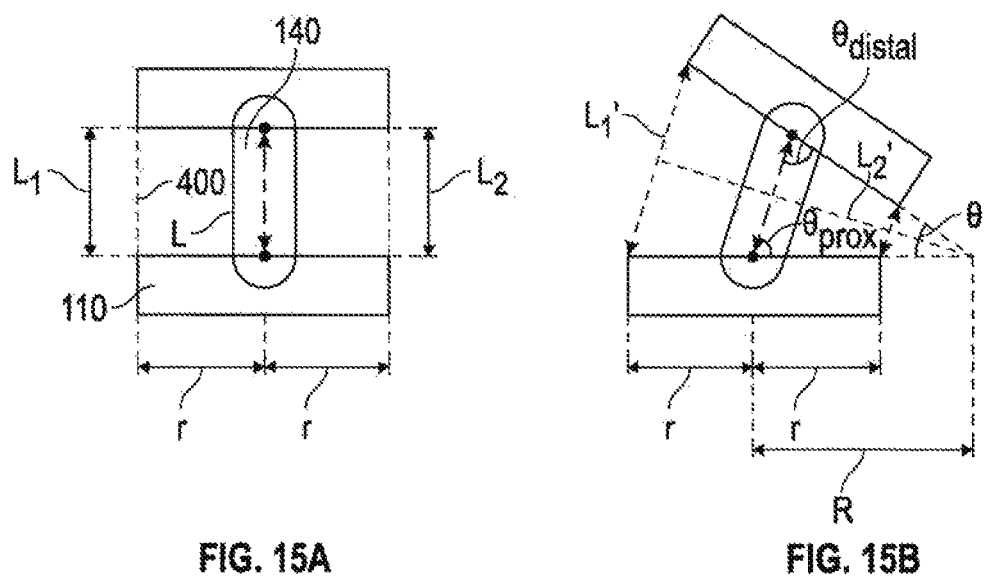
FIGS. 15A, 15B, 16A, 16B 17A and 17B are views illustrating a steerable member having connecting segments using a double hinge structure.
Figure 16A:
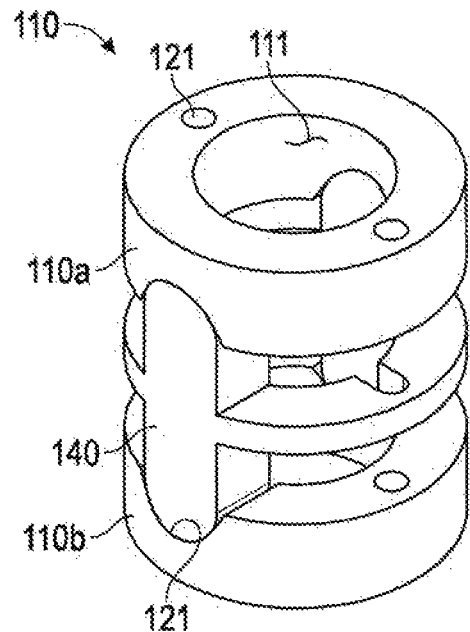
Figure 16B:
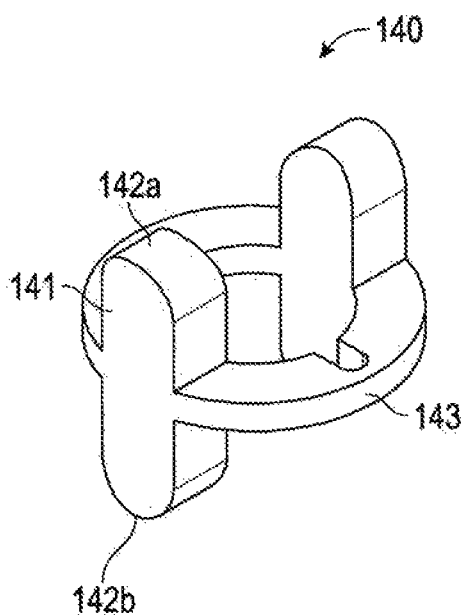
Figure 17A:
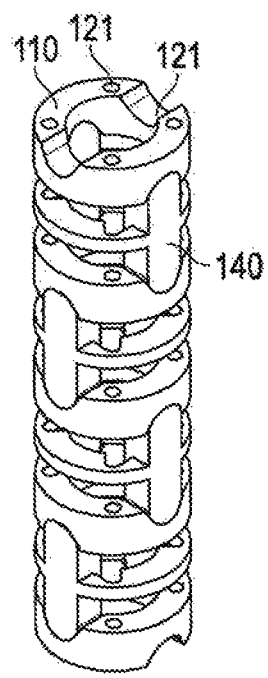
Figure 17B:
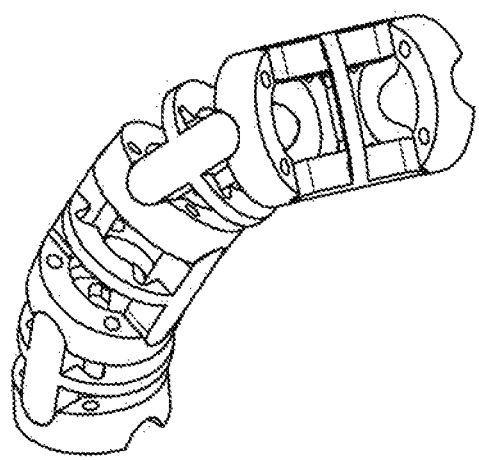

In addition, a bending mechanism using connecting segments that causes no backlash, as well as the above-mentioned method using a lateral supporting member, may be used, as shown in FIGS. 15 to 17.

FIG. 15 illustrates the wire path difference caused by bending of bending segments 110 connected by connecting segments. In the foregoing exemplary embodiment (e.g., in FIGS. 3 to 9), each bending segment 110 is coupled directly to adjacent bending segments through the connecting parts 120 provided in the body, and they move relative to one another along a hinge axis shared between each pair of adjacent bending segments 110. In contrast, as shown in FIG. 15, a connecting segment 140 is provided between each pair of adjacent bending segments 110, and two adjacent bending segments are connected to two ends of the connecting segment 140, respectively. The connecting segment 140 has a double hinge joint structure that enables two points on the connecting segment 140 to form a hinged relationship to two different members. Accordingly, a pair of adjacent bending segments 110 is coupled to two ends of the connecting segments 140, respectively, so as to rotate relative to different hinge shafts, without sharing a hinge shaft.

Let the distance between the wires on either side of a bending segment 110 be 2r and let the distance between two hinges shafts of the connecting segment be L. The bending segment 110 may be hinged to the connecting segment 140, at a point midway between a pair of wires (i.e., at a distance of r from each wire).

FIG. 15A illustrates the adjacent bending segment before bending, and FIG. 15B illustrates the adjacent bending segment when moved to form a bend of a radius of curvature R. In FIG. 15B, the bend angle between two adjacent bending segments 110 is denoted by θ. Also, it can be assumed that the angles θprox and θdistal of bend between the bending segments and the connecting segment created by bending are equal. In this case, the following equation is used to compare the sum of the lengths of two wire portions between the two bending segments before bending and the sum of the lengths of the two wire portions after bending. The lengths of the two wire portions before bending are denoted by $L_1$ and $L_2$, respectively, and the lengths of the two wire portions after bending are denoted by $L_1'$ and $L_2'$, respectively.

$$L_1 = L_2 = L$$

$$L_1' = 2(R+r)\sin\left(\frac{\theta}{2}\right)$$

$$L = 2R\sin\left(\frac{\theta}{2}\right)$$

$$L_2' = 2(R-r)\sin\left(\frac{\theta}{2}\right)$$

$$L_1 + L_2 = 2L = 4R\sin\left(\frac{\theta}{2}\right)$$

$$L_1' + L_2' = 2(R+r)\sin\left(\frac{\theta}{2}\right) + 2(R-r)\sin\left(\frac{\theta}{2}\right) = 4R\sin\left(\frac{\theta}{2}\right)$$

$$L_1 + L_2 = L_1' + L_2'$$

That is, if the steerable member 100 connected by the connecting segment 140 is bent, the sum ($L_1+L_2$) of the lengths of the two wire portions before bending and the sum ($L_1'+L_2'$) of the lengths of the two wire portions after bending are substantially equal. Accordingly, slack in the wires caused by the bending can be prevented.

In FIG. 15 it is assumed that the angles of bend θprox and θdistal between the bending segments 140 and the connecting segment 110 are equal because bending is imposed at each bending segment by to the same wire. However, when actual bending occurs, the angles of bend between the connecting segment 140 and the bending segments 110 are within a substantially similar range although they are slightly different. Thus, the length of slack can be minimized as compared to the structure in which two bending segments are coupled together on a single hinge shaft.

FIG. 16 is a perspective view illustrating a connecting segment and bending segments connected by the connecting segment. FIG. 17 is a perspective view illustrating a steerable member comprising connecting segments.

As illustrated in FIG. 16, a connecting segment 140 is hinged to a first bending segment 110a and a second bending segment 110b at different points. The connecting segment 140 comprises two bodies 141 spaced apart across a central opening. Each body 141 includes a first hinge part 142a on one end of its length and a second hinge part 142b on the other end. The first and second bending segments 110a and 110b are coupled to the first and second hinge parts 142a and 142b, respectively, so that they move with respect to the connecting segment about different hinge axes.

In FIG. 16, the first hinge part 142a and the second hinge part 142b each consist of a protrusion with a round surface, which are accommodated in recesses 121b formed extending inwardly of the bending segments 110, wherein the protrusion surfaces slide along the surface of the recesses to allow the hinged movement between the bending segments 110a, b and the connecting portion 140. However, this is merely an example, and at least one of the first and second hinge parts may be a recess for accommodating a protrusion or may be connected by other hinge structures.

The connecting segment 140 further comprises a guide member 143 with a hollow space inside it that joins together the two bodies 141 facing each other. The hollow space of the guide member 143 allows various kinds of wire members such as the bending actuation wires or the end effector actuation wire to pass through, and prevents internal components from moving outwardly thereof during bending of the resulting steerable member 100. A cross-section of the guide member 143 may be similar to a cross-section of the bending segments. In this case, portions through which the bending actuation wires pass may be open so as not to restrict the movement of the bending actuation wires.

The steerable member of FIG. 17 comprises a plurality of connecting segments 140, and adjacent connecting segments 140 are configured to have hinge axes orthogonal to each other. Each bending segment 110 has four lumens 112 so that a bending actuation wire 400 is located in each of them. Therefore, the steerable member 100 can bend with 2 degrees of freedom. In this case, the bending actuation wires 400 may be located between each hinge shaft location around the body of the bending segments 110 so as not to pass through the hinge shafts of the connecting segments 140.

Figure 18B:
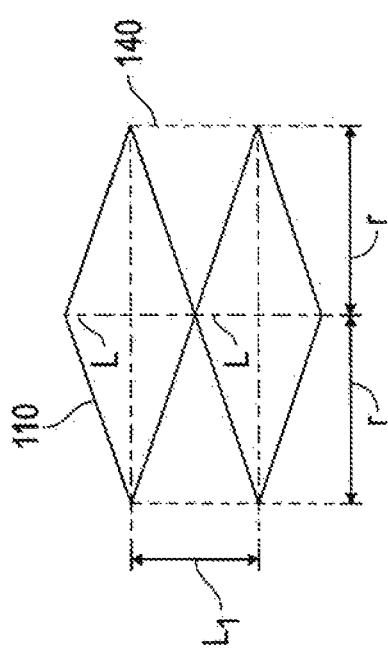
FIGS. 18A, 18B, 19A and 19B are views illustrating a steerable member using a path adjusting member.
Figure 18A:
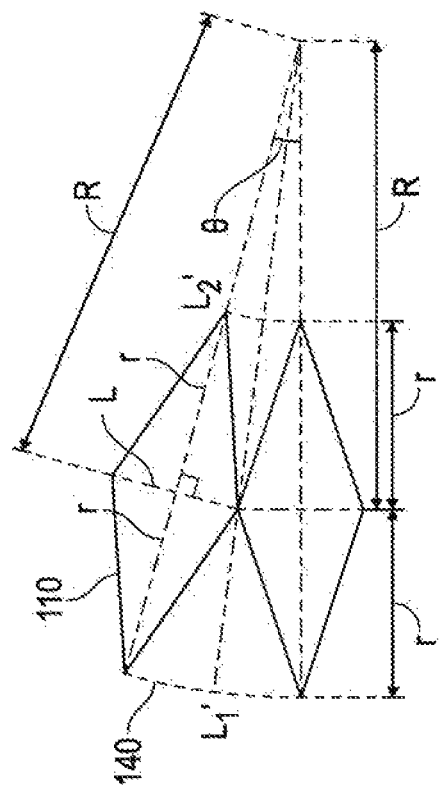

In another exemplary embodiment, FIGS. 18A and B schematically illustrate slack in a wire that forms a curved path due to bending of the steerable member 100. While FIG. 3 depicts a wire that follows a bent straight-line path when bending occurs, FIG. 18 depicts a wire that follows a curved path when bending occurs. If the lengths of two wire portions before bending are denoted by $L_1$ and $L_2$, respectively, and the lengths of the two wire portions after bending are denoted by $L_1'$ and $L_2'$, respectively, the relationship between the lengths of the two wire portions is as follows:

$$L_1 + L_2 = 4R\tan\left(\frac{\theta}{2}\right)$$

$$L_1' + L_2' = (R+r)\theta + (R-r)\theta = 2R\theta$$

$$\Delta L_{slack} = (L_1 + L_2) - (L_1' + L_2') = 4R\left(\tan\left(\frac{\theta}{2}\right) - \frac{\theta}{2}\right) > 0$$

$$[\Delta L_{slack} < \Delta L_{Fig3} = 4R(\tan(\theta/2) - \sin(\theta/2))]$$

As compared with the wire of FIG. 3 that forms a bent straight-line path when bending occurs, the wire of FIG. 18 that forms a curved path can have an approximately 30% reduction in the length of the slack. Using this principle, the bending actuation wires are configured to form a curved path when bending occurs by including a path adjusting member, thereby minimizing the slack.

Figure 19A:
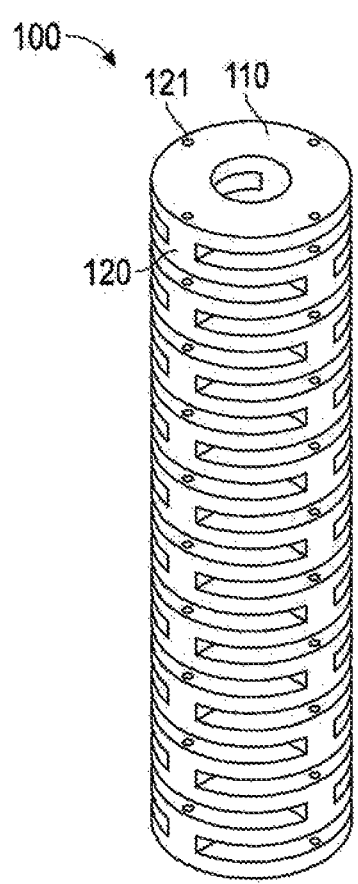

FIG. 19 is a view illustrating a steerable member using a path adjusting member. As illustrated in FIG. 19, the steerable member 100 comprises plate-like bending segments 110 and wall-like connecting parts 120 located between the bending segments. Also, four lumens 112 are formed to penetrate the outer edges of the bending segments 100 and connecting parts 120 (refer to the description of FIG. 10).

Figure 19B:
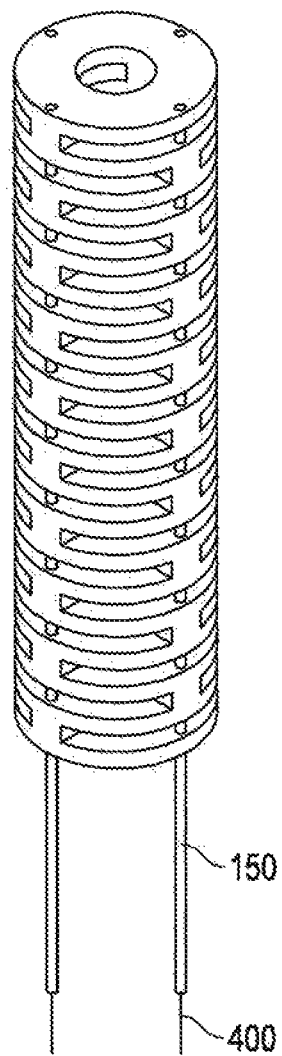

As illustrated in FIG. 19B, bending actuation wires 400 are located inside the path adjusting member 150 in each lumen, rather than being located directly in each lumen. The path adjusting member 150 comprises an elastic material such as metal, and bends when the steerable member 100 is bent, thereby forming a curved wire path (in this case, the stiffness of the path adjusting member does not need to be high enough to produce a restoration force as shown in FIGS. 13 D and E, and an elastic force sufficient to form a curved path will do). Accordingly, the bending actuation wires 400 according to this exemplary embodiment bend not along a bent straight-line path but along a curved path, thereby minimizing the length of wire slack.

While this exemplary embodiment has been described with respect to an example in which the path adjusting member is used for the steerable member using a flexible hinge structure, modifications may be made, like placing wires in the steerable member shown in FIGS. 11 to 17 with the use of the path adjusting member.

FIGS. 20A and B illustrate bending of the steerable member. As illustrated in FIG. 20B, at the initial stage of the bending, the bending is not uniform across the entire steerable member 100, but it is concentrated at the distal end of the steerable member where the bending actuation wire 300 is attached. Thus, a force is transmitted directly to the distal end of the steerable member when the end of the wire is moved in the direction inwardly of the steerable member 100, resulting in less bending of the steerable member at the proximal end thereof.

FIGS. 21A to C are side views of a steerable member 100 according to one exemplary embodiment of the present invention. FIGS. 21A, B, and C depict an embodiment to reduce the concentration of bending at the distal end of the steerable member, by forming a geometrically enhanced structure in which the steerable member bends more easily at the proximal end than at the distal end.

Specifically, as shown in FIG. 21A, the bending segments 110 have lumens formed at a distance from the center of a cross-section of the steerable member, and the closer to the proximal end of the steerable member, the more distant the lumens in the bending segments get from the center of the cross-section of the steerable member. In this case, the moment applied to the steerable member 100 is smaller at the distal end and increases towards the proximal end. Thus, the steerable member 100 bends more easily toward the proximal end thereof.

In FIG. 21B, the connecting parts 120 are configured to gradually change in shape along the length of the steerable member 100 such that the steerable member bends more easily at the proximal end than at the distal end. In an example, as illustrated in FIG. 21B, the bending properties along the length can be adjusted by configuring the connecting parts to have a larger sectional width at the distal end than at the proximal end. Alternatively, apart from adjusting the width of the connecting parts, the connecting parts may be configured in other various ways of shape variation, including adjusting the range of movement of connecting parts having a joint structure.

Also, as shown in FIG. 21C, the distance between the bending segments 110 may change along the length. Specifically, the connecting parts 120 may be positioned such that the distance between the bending segments gets shorter toward the distal end and longer toward the proximal end. In this case, the longer the distance between the bending segments, the easier the bending of the steerable member. This results in restriction of the bending near the distal end and improvement in the bending properties near the proximal end.

The steerable member of this configuration has a plurality of bending actuation wires located along the lumens, and the distal end of each bending actuation wire is fixed by a wire termination member 410 provided at the distal end of the steerable member.

Figure 22A:
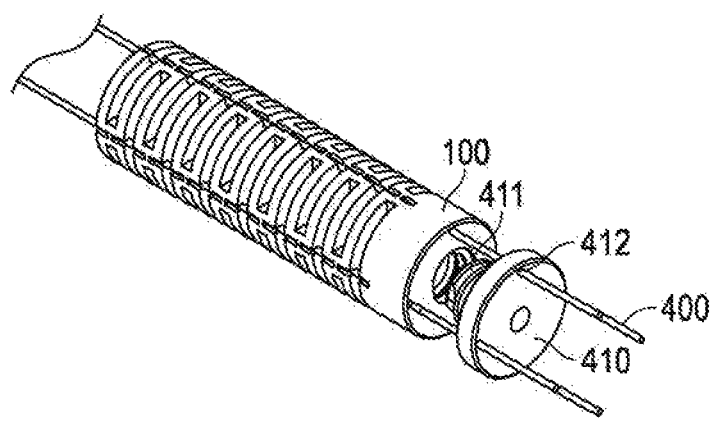
FIG. 22A-22C are views illustrating a method of fixing bending actuation wires by a wire termination member.
Figure 22B:
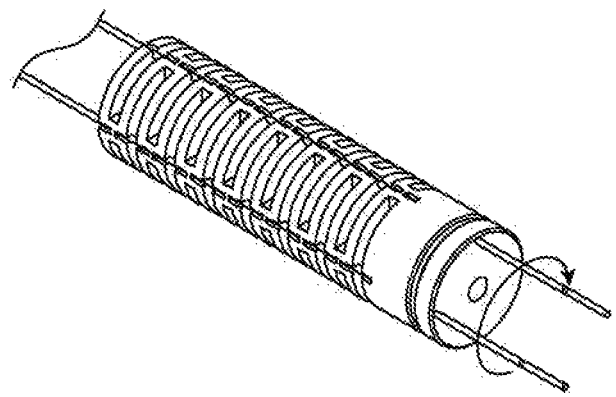
Figure 22C:
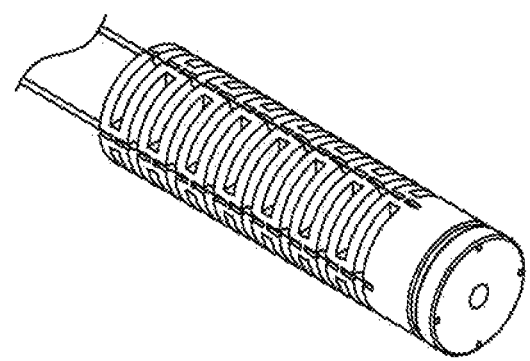

FIGS. 22A to C illustrate a method of fixing the bending actuation wires to the steerable member 100 using a wire termination member. As the steerable member 100 and the bending actuation wires 400 are very small in size, fixing individual bending actuation wires to the distal end of the steerable member is highly difficult. Accordingly, this exemplary embodiment uses a wire termination member capable of easily fixing a plurality of bending actuation wires.

As illustrated in FIG. 22A, the wire termination member 410 has a thread 411 on one side, and is screwed to the distal end of the steerable member 100. Also, the wire termination member includes a plurality of holes 412 through which a plurality of bending actuation wires pass, and the holes 412 are formed at locations corresponding to the lumens in the steerable member. Accordingly, as shown in FIG. 22B, the wire termination member 410 can be screwed to the distal end of the steerable member 100 while the bending actuation wires 400 are inserted in the holes of the wire termination member (FIG. 22A), thereby making it easy to fix the bending actuation wires (B and C of FIG. 22) to the steerable member 100.

Figure 23:
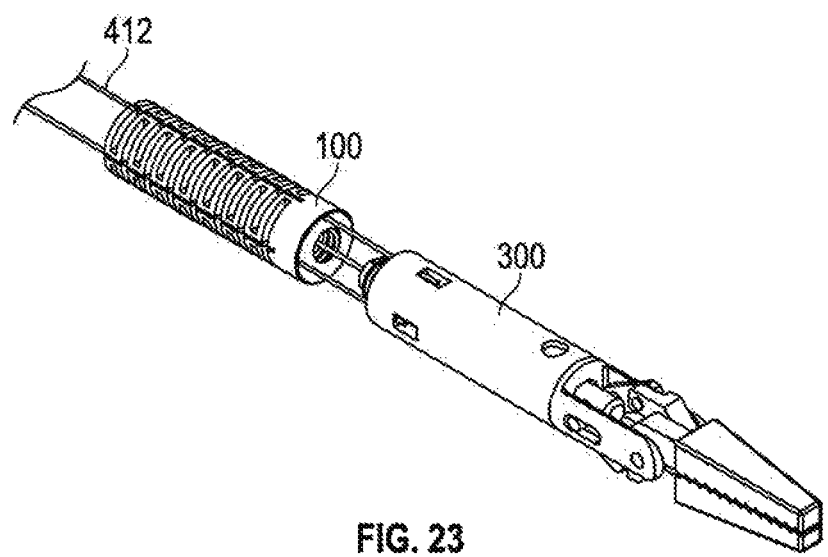
FIG. 23 is a view illustrating an example of configuring an end effector as a wire termination member.

The wire termination member 410 may be a component that is provided between the steerable member 100 and the end effector 300. In this case, the wire termination member 410 may be screwed to the distal end of the steerable member 100, and the end effector 300 may be connected to the wire termination member 410. Alternatively, as illustrated in FIG. 23, the end effector 300 may be used as the wire termination member by fixing the bending actuation wires 400 to the inside of the end effector 300 and screwing the end effector 300 directly to the distal end of the steerable member 100.

Although FIG. 22 has been described with respect to a steerable member having the structure shown in FIG. 10, it is needless to say that the bending actuation wires can be likewise fixed even if the steerable member has other structures.

In the above discussion, various exemplary embodiments of the steerable member have been described with reference to FIGS. 5 to 22. The steerable member 100 is described as a component of the surgical apparatus that has an end effector, but the present invention is not limited thereto. For example, the present invention is applicable to bendable steerable members for various kinds of surgical instruments, such as an imaging unit or a lumen unit with a working channel.

Referring back to FIG. 2, the end effector 300 is provided at the distal end of the steerable member. As described above, the end effector 300 may be coupled directly to the distal end of the steerable member 100 or coupled to it through a component such as the wire termination member. The end effector 300 comprises various types of surgical elements for use in surgery. FIG. 2 illustrates an end effector comprising forceps 31 by way of example.

The proximal end of the end effector 300 is connected to the effector actuation wire 500. The effector actuation wire 500 is located in the channels 111 of the steerable member 100, and mechanically connected to the manipulating part 10 through the steerable member 100 and the tubular flexible member 200. Accordingly, the effector actuation wire 500 actuates the end effector 300 as it moves lengthwise by the manipulating part 10.

Figure 24:
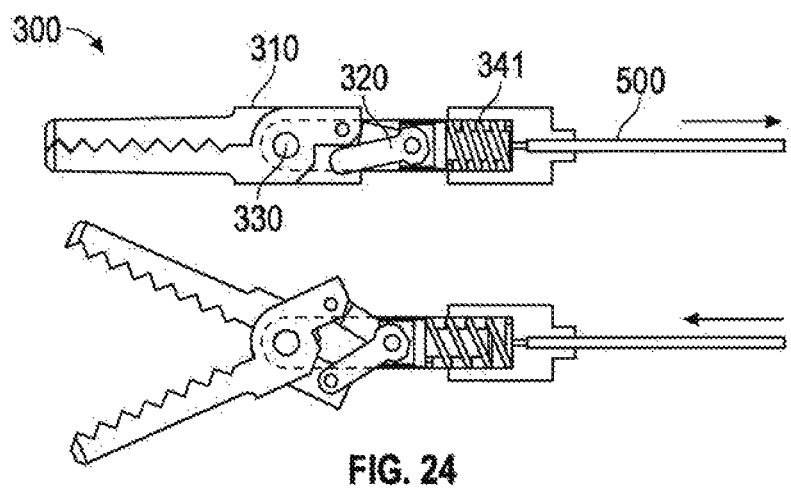
FIGS. 24 and 25 are views illustrating a structure of the end effector.

FIG. 24 is a cross-sectional view schematically illustrating the operating principle of the end effector. The end effector 300 operates in a first mode when the effector actuation wire 500 is pulled in the direction of the manipulating part 10 (FIG. 24A), and operates in a second mode when the effector actuation wire 500 is pulled in the direction of the end effector 300 (B of FIG. 24). In the first mode, when the actuation wire 500 is pulled in the direction away from the end effector, the forceps of the end effector, close and when the pulling force on the actuation wire 500 is released, an internal spring mechanism in the forceps causes the jaws thereof to open. The action of pulling the effector actuation wire 500 in the direction of the manipulating part may be done easily by the driving part 40 of the manipulating part, thereby transmitting the force to the end effector. On the other hand, the action of bringing the effector actuation wire 500 back in the direction of the end effector 300 may not be done properly by the driving part 400 because the effector actuation wire has a wire structure. Accordingly, in this exemplary embodiment, the end effector 400 include an elastic body 341 to perform the second mode operation by pulling the end of the end effector actuation wire 500 in the direction of the end effector using the elasticity of the elastic body 341.

Specifically, as illustrated in FIG. 24, an effector module of the end effector comprises an instrument portion 310 for performing a surgical operation and an actuation portion 320 for actuating the instrument portion 310. The instrument portion 310 is linked to the actuation portion 320, and configured such that the surgical elements, e.g. forceps 31 in FIGS. 1 and 2 are opened or closed on both sides by the movement of the actuation portion 320 while a joint 330 of the instrument portion 310 is fixed. The elastic body 341 may be located at the proximal end of the actuation portion. When the effector actuation wire 500 is pulled by the manipulating part 10, the actuation portion 320 moves backward while pushing the elastic body 341 and the surgical elements are therefore closed (FIG. 24A). Also, when the force acting on the effector actuation wire 500 is released by the manipulating part 10, the restoration force of the elastic body 341 causes the actuation portion 320 to move in the direction of the instrument portion 310, thereby opening the surgical elements (see e.g. FIG. FIG. 24). In this way, the operative mechanism of the end effector can be simplified with the use of the elastic body.

Figure 25:
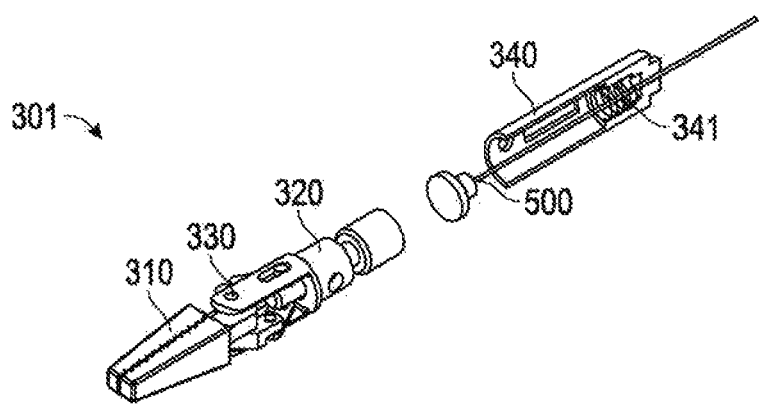

The structure of the end effector using the elastic body may be designed in various ways. FIG. 25 is a view illustrating an example of such an end effector. As illustrated in FIG. 25, the end effector 300 comprises an effector module 301 and a body portion 340 where the effector module 301 is mounted. The instrument portion 310 of the effector module 301 is configured to be exposed to the distal end of the body portion 340, and the actuation portion 320 thereof is accommodated inside the body portion 340. A joint 330 connecting the instrument portion 310 and the actuation portion 320 may be fixed at the body portion 340, and the actuation portion 320 may reciprocate inside the body portion 340. The elastic body 341 provided inside the body portion 340 is located behind the actuation portion 320, and the proximal end of the actuation portion 320 is connected to the effector actuation wire 500. Accordingly, the instrument portion 310 is manipulated by moving the actuation portion 320 with the effector actuation wire 500 and the elastic body 341.

Also, all or part of the end effector 300 may be detachably connected to the distal end of the steerable member 100. Accordingly, a variety of instruments needed for surgery may be selectively fastened and used. In an example, the end effector 300 of FIG. 25 is configured such that the effector module 301 is attachable to or detachable from the distal end of the effector actuation wire 500. The effector module 301 and the distal end of the effector actuation wire 500 may be detachably fastened in various ways; for example, they may be magnetically fastened together according to the exemplary embodiment illustrated in FIG. 25. Accordingly, at least either the proximal end of the actuation portion 320 or the distal end of the effector actuation wire 500 consists of a magnetic body, which enables the fastening.

As described above, a surgical instrument according to this exemplary embodiment comprises a bendable steerable member 100 and an operable end effector 300. Also, the steerable member 100 and the end effector 300 are moved by a plurality of wire members such as the bending actuation wires 400 and the effector actuation wire 500. These wire members are arranged to pass through the steerable member 100 and the tubular flexible member 200. Accordingly, if the wire members are linearly arranged so that each of them has the shortest path, the movement of the wires may be restricted or affected by the bending of the steerable member or flexing of the flexible member. Therefore, in this exemplary embodiment, at least one sleeve forming a path of travel of a wire member may be provided inside the steerable member or the flexible member. This sleeve is longer than the maximum length of the portion where the sleeve is provided (for example, the length of that portion when bent or flexed), so the wire members have a long enough path even when the steerable member is bent or the flexible member is flexed.

Figure 26:
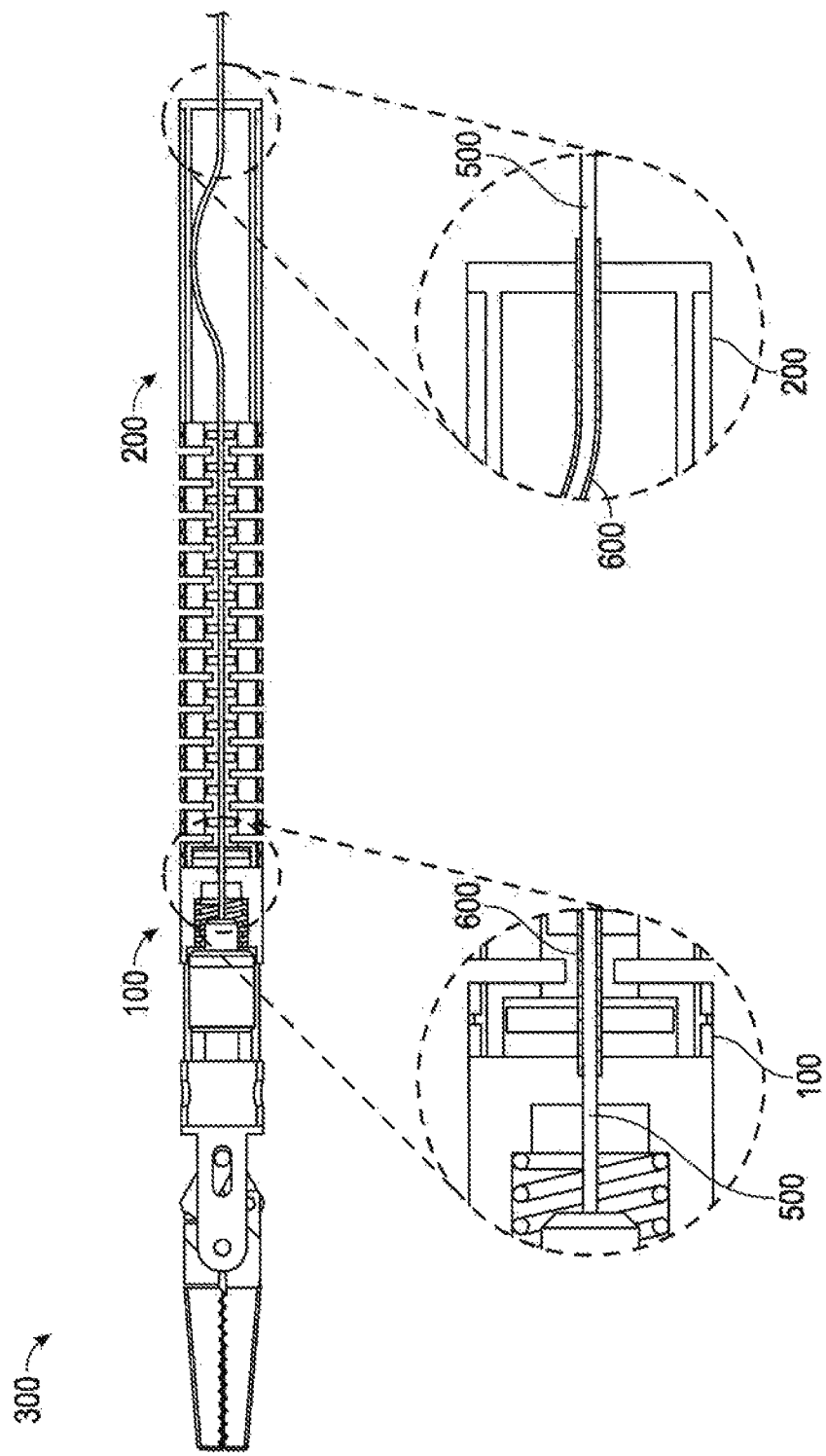
FIGS. 26 to 29 are views illustrating various examples of a surgical apparatus with a sleeve in it.

FIG. 26 is a cross-sectional view illustrating a path of travel of the effector actuation wire. As illustrated in FIG. 26, one end of the effector actuation wire 500 is mounted at the proximal end of the end effector 300, and the other end is mechanically connected to the manipulating part 10 (FIG. 1). One end of a sleeve 600 forming a path of the effector actuation wire 500 is fixed in place at the distal end of the steerable member 100 or the proximal end of the end effector 300. Also, the other end is fixed in place at the proximal end of the tubular flexible member 200. In this instance, the sleeve 600 is longer than the length of the portion where two ends of the sleeve are fixed (the sum of the length of the steerable member and the length of the flexible member). This extra length added to the sleeve (FIG. 26A) gives more room for the path of the effector actuation wire 500 even when the steerable member 100 is bent (FIG. 26B). Accordingly, the movement of the end effector 300 may be decoupled from the bending movement of the steerable member 100 to prevent its movement from being affected by the bending movement of the steerable member 100.

Figure 27:
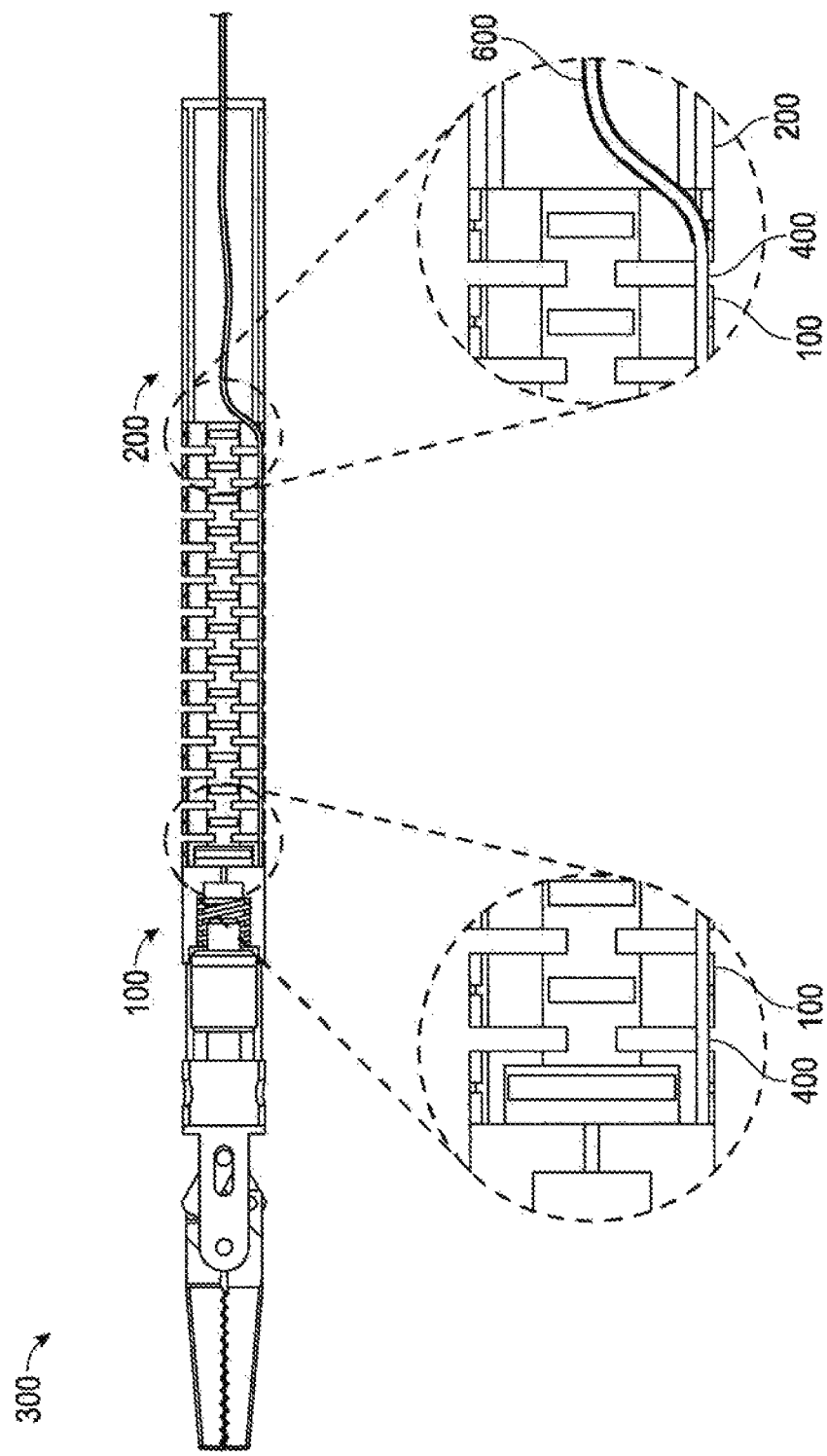

FIG. 27 is a view illustrating a path of travel of the bending actuation wire. As illustrated in FIG. 27, a sleeve 600 for securing the path of the bending actuation wire 400 may be provided. In this case, one end of the sleeve 600 is fixed at the proximal end of the steerable member 100 or the distal end of the flexible member 200, and the other end is fixed at the proximal end of the flexible member 200. The sleeve 600 is configured to have an extra length added to the linear length of the portion where the sleeve is placed. Accordingly, the bending of the steerable member 100 will not be affected by the flexing of the tubular flexible member 200.

Figure 28:
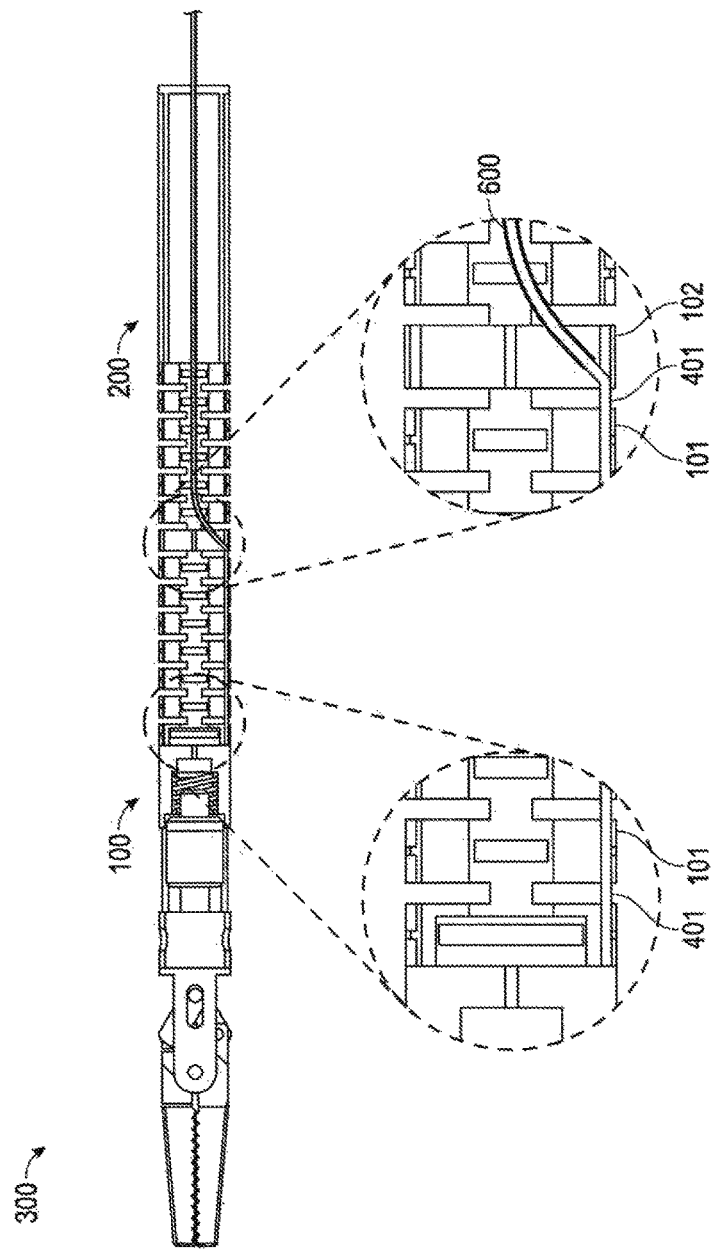
Figure 29:
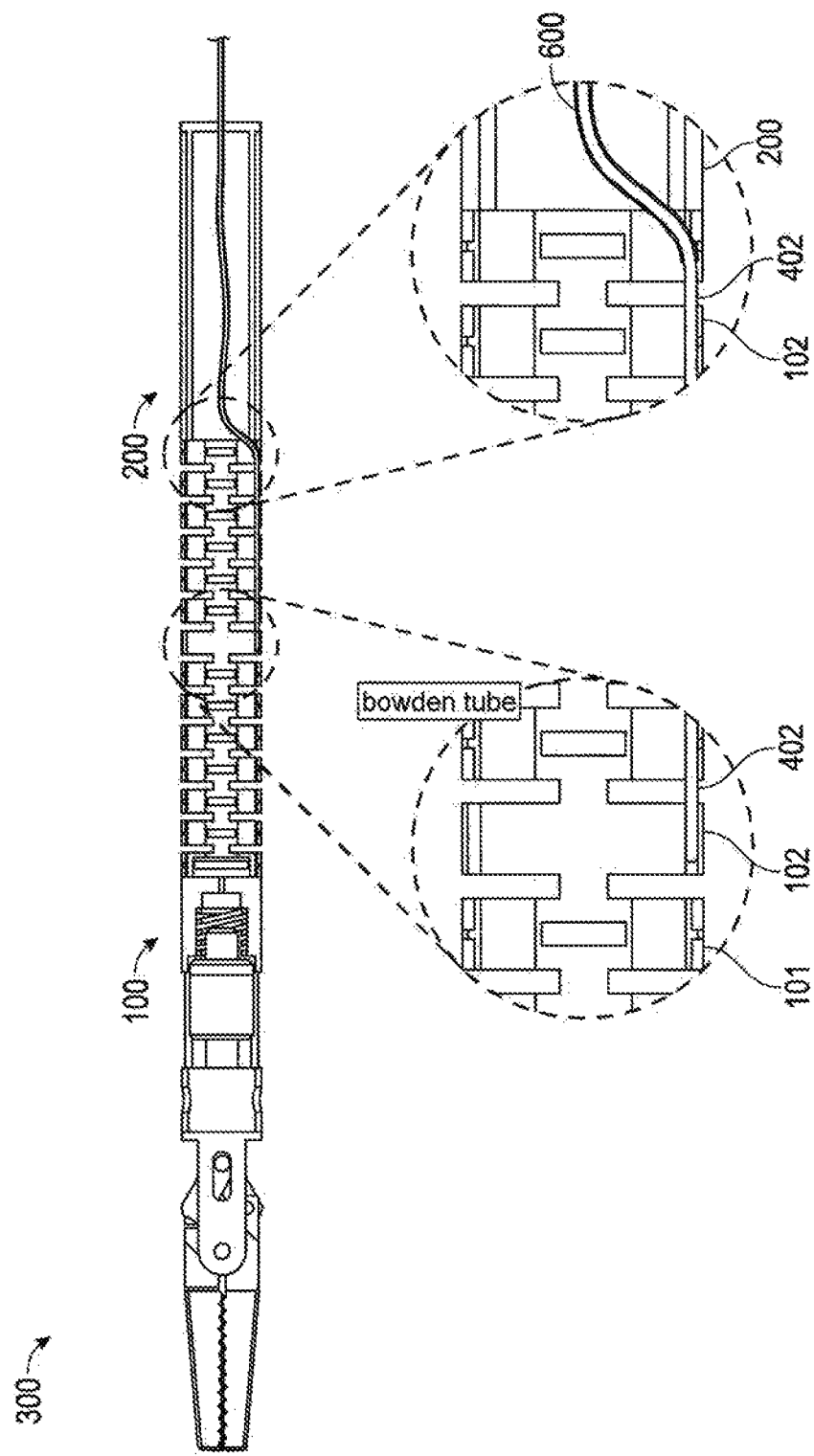

FIGS. 28 and 29 are views illustrating a path of travel of a bending actuation wire 400 with two bendable portions. While the previous drawings illustrate a structure in which the steerable member 100 has one bending portion, the steerable member 100 may be divided into a distal end steerable portion 101 and a proximal end of steerable portion 102, which can bend separately. In this case, the distal end steerable portion 101 is bent with a distal end bending actuation wire 401, and the proximal end steerable portion 102 is bent with a proximal end bending actuation wire 402. One end of the distal end bending actuation wire 401 is fixed at the distal end of the distal end steerable portion 101, passes through the lumens in the distal end steerable portion 101, and then extends to the manipulating part 10 through hollow channels of the steerable member 100 and flexible member 200. Also, one end of the proximal end bending actuation wire 402 is fixed at the distal end of the proximal end steerable portion 102, passes through the lumens in the proximal end steerable portion 102, and then extends to the manipulating part 10 through hollow channels of the tubular flexible member 200. In this instance, two distal end bending actuation wires 401 and two proximal end bending actuation wires 402 may be provided and have 1 degree of freedom in each bending portion, or four distal end bending actuation wires 401 and four proximal end bending actuation wires 402 may be provided and have 2 degrees of freedom in each bending portion.

As illustrated in FIG. 28, a sleeve 600 for securing a path of the distal end bending actuation wire 401 may be provided. One end of this sleeve 600 may be fixed at the proximal end of the distal end steerable portion 101, and the other end may be fixed at the proximal end of the tubular flexible member 200. Also, as illustrated in FIG. 29, a sleeve 600 for securing a path of the proximal end bending actuation wire 402 may be provided. One end of this sleeve 600 may be fixed at the proximal end of the proximal end steerable portion 102, and the other end may be fixed at the proximal end of the tubular flexible member 200. As is the case with the above-mentioned sleeves, each sleeve 600 has an extra length, so the bending movement of each bending portion can be decoupled.

As described above, the sleeves 600 explained with reference to FIGS. 26 to 28 have an extra length added to the length of the portion where they are placed, and they may comprise an elastic material, allowing their shape to change along with the movement of the components. Such a sleeve structure allows decoupling of the movement of each component from the movement of the others, and prevents wire members in narrow channels from being twisted or damaged by friction.

Figure 30:
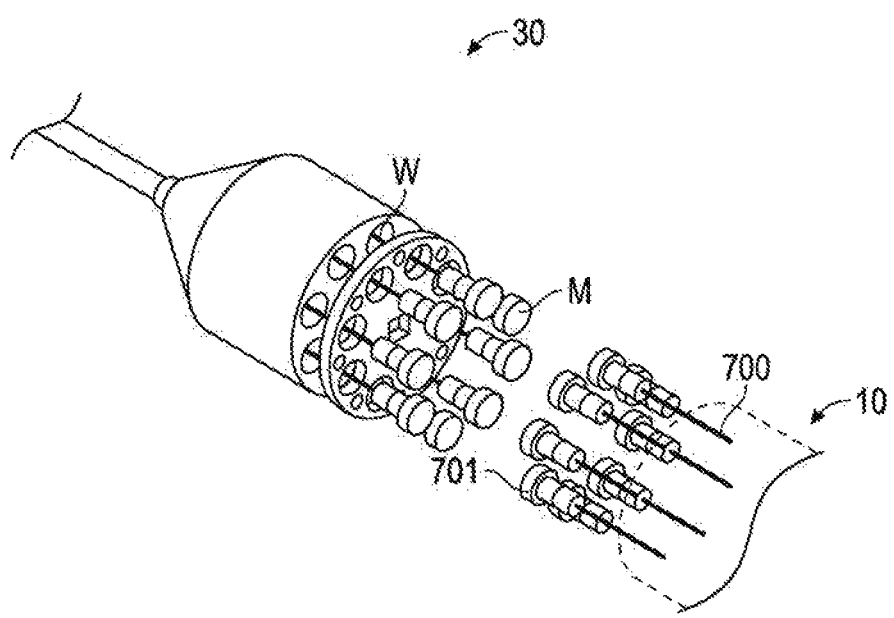
FIG. 30 is a view illustrating a connecting structure of the end of a surgical instrument and a manipulating part.

FIG. 30 is a view illustrating a connecting structure of the end of a surgical instrument and the manipulating part. As explained above, the surgical instruments 30 are respectively located in passages in the insertion part 20, and the end of a surgical instrument is mechanically connected to the manipulating part 10. The manipulating part 10 comprises transmission members 700 corresponding to a plurality of wire members W of the surgical instrument and couplers 701 to be fastened to wires. The wire members W of the surgical instrument each include a proximal end module M at the proximal end, and each proximal end module M is fastened to the corresponding coupler 701. Thus, each wire member can be moved by each driving part in the manipulating part.

In this case, the insertion part 20 and the manipulating part 10 are attachable to or detachable from each other, and the surgical instrument 30 provided in the insertion part 20, too, is attachable to or detachable from the manipulating part 20. This means that the insertion part or the surgical instrument can be cleaned or replaced with new ones. The surgical instrument 30 and the manipulating part 10 may be detachably fastened in various ways; for example, they may be magnetically fastened together, as shown in FIG. 30. Accordingly, the proximal end of the surgical instrument (specifically, the proximal end modules of the bending actuation wires and effector actuation wire) or the distal end of the manipulating part (specifically, the couplers of the transmission members) may be consist of a magnetic body and be attached to or detached from each other by magnetic force.

Figure 31A:
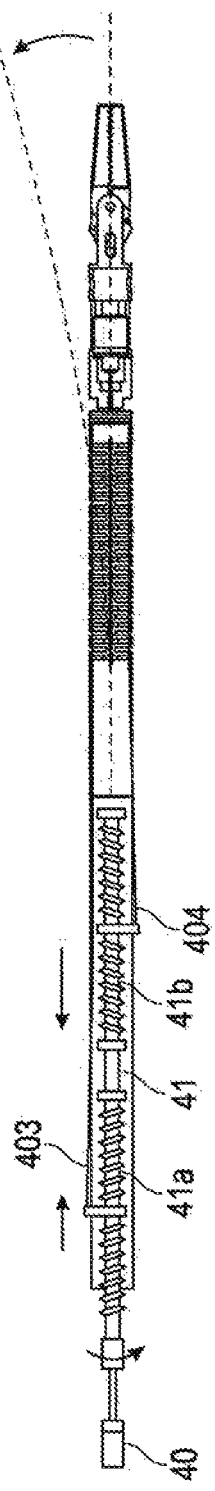
FIGS. 31A, 31B and 32 schematically illustrate the configuration of the manipulating part for moving bending actuation wires.
Figure 31B:
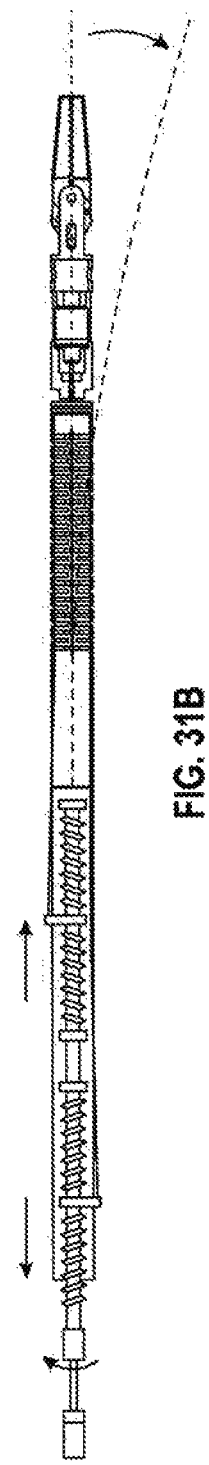
Figure 32:
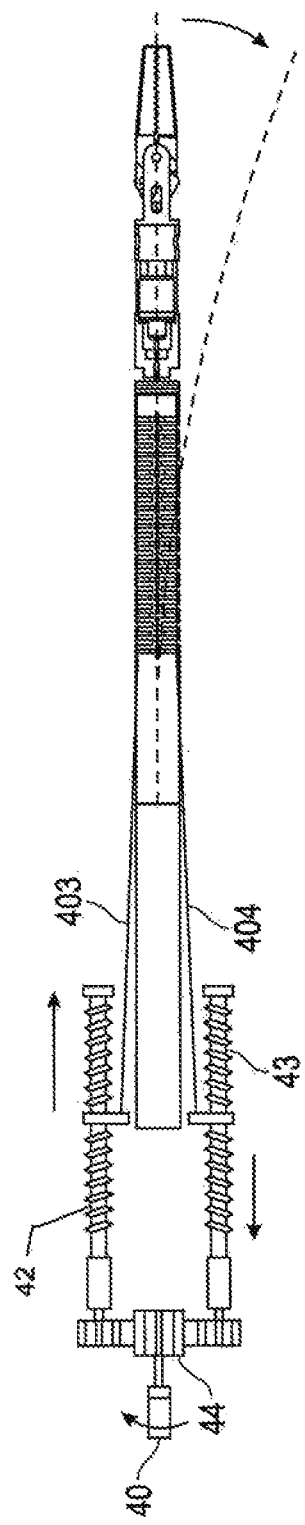

FIGS. 31 and 32 schematically illustrate the configuration of the manipulating part 10 for moving the bending actuation wires 400. The wire members W of the above-described surgical instrument are mechanically connected to the driving part 40 of the manipulating part 10 and move linearly along with the movement of the driving part 40. The driving part may be constructed using various devices such as an actuator, a linear motor, a motor, etc. Also, each wire member may be connected to different driving parts so that they can move separately.

In this instance, a pair of bending actuation wires 400 located facing each other within the steerable member 100 move in opposite directions when bending occurs. Specifically, when bending occurs, the bending actuation wire near the center of curvature has a shorter path and the bending actuation wire on the other side of the center of curvature has a longer path. Accordingly, the pair of wires facing each other may move simultaneously in opposite directions with the use of a single driving part 40. In this case, the manipulating part can be designed to be compact by reducing the number of driving parts.

In FIG. 31, the manipulating part comprises a screw member 41 and a driving part 40 for rotating the screw member 41. The screw member 41 may be a bi-directional lead screw, which means that two thread portions having different orientations are formed on a single screw member. Accordingly, the coupler of a transmission member to be connected to a first bending actuation wire 403 is coupled to a first thread 41a, and the coupler of a transmission member to be connected to a second bending actuation wire 404 is coupled to a second thread 41*b*. Accordingly, as the driving part rotates, the first bending actuation wire 403 and the second bending actuation wire 404 move respectively a corresponding distance, in opposite directions on a straight line, thereby causing the steerable member to bend. Also, the directions of movement of the first bending actuation wire 403 and the second bending actuation wire 404 may be reversed by changing the direction of rotation of the driving part, thus enabling them to bend in the reverse direction.

In FIG. 32, the manipulating part comprises a pair of screw members and a driving part 40 for rotating the screw members. The pair of screw members consists of a first lead screw 42 with a first thread 41*a* and a second lead screw 43 with a second thread 41*b* oriented in the opposite direction to the first thread. The first lead screw 42 and the second lead screw 43 are connected to the driving part 40 by a gear 44 and rotate in the same direction along with the rotation of the driving part. The first bending actuation wire 403 is mechanically connected to the first lead screw 42, and the second bending actuation wire 404 is mechanically connected to the second lead screw 43. Accordingly, as is the case in FIG. 31, when the motor (not shown in this figure) rotates, the first and second bending actuation wires 403, 404 may move in opposite directions, causing the steerable member to bend.

Although FIGS. 31 and 32 depict the use of a screw member as an example to drive the bending actuation wires in a pair, it is needless to say that modifications can be made using various link structures.

FIG. 33 is a view schematically illustrating the length of a bending actuation wire before and after bending in an ideal continuous flexible arm. FIG. 33 A shows the length of the bending actuation wire before bending in an ideal continuous flexible arm, while FIG. 33 B shows the length of the bending actuation wire after bending in an ideal continuous flexible arm being pulled with a wire-driven mechanism A (e.g. a pulley).

In an ideal continuous flexible arm, let a bending actuation wire be located on two opposite sides of the wire-driven mechanism A having a width of 2r, wherein "r" indicates a radius of the wire-driven mechanism A; "$L_1$" and "$L_2$" respectively indicate the length of the bending actuation wire from both opposite sides of the wire-driven mechanism A to the bending segment (not shown) before bending; "$L_1'$" and "$L_2'$" respectively indicate the length of the bending actuation wire from both opposite sides of the wire-driven mechanism A to the bending segment (not shown) after bending; "L" indicates the length from the center of the wire-driven mechanism A to the bending segment; "R" indicates a radius of curvature when the wire-driven mechanism A is pulled as an arrow pointed to, and the angle of bend by the wire-driven mechanism A is denoted by "θ".

In the ideal continuous flexible arm shown in FIG. 33, the total length of the bending actuation wire before and after bending can be represented as the following equation:

before bending: $L_1+L_2=2R\theta$;

after bending: $L_1'+L_2'=(R+r)\theta+(R-r)\theta=2R\theta$; $L_1+L_2=L_1'+L_2'$.

However, as shown in FIG. 34 which is a view schematically illustrating the length of a bending actuation wire before (shown in FIG. 34 A) and after bending (shown in FIG. 34 B) in the actual condition. As FIG. 34 B illustrated, the bending actuation wire is elongated by being pulled (indicated as ΔL elongation), resulting in slack B on the released wire, which causes backlash. In this condition, the total length of the length of the bending actuation wires before and after bending can be represented as the following equation:

before bending: $L_1+L_2=2R\theta$;

after bending: $L_1'+L_2'+\Delta L$ elongation$=(R+r)\theta+(R-r)\theta+\Delta L$ elongation$=2R\theta+\Delta L$ elongation;

$L_1+L_2 \neq L_1'+L_2'+\Delta L$ elongation.

Figure 35:
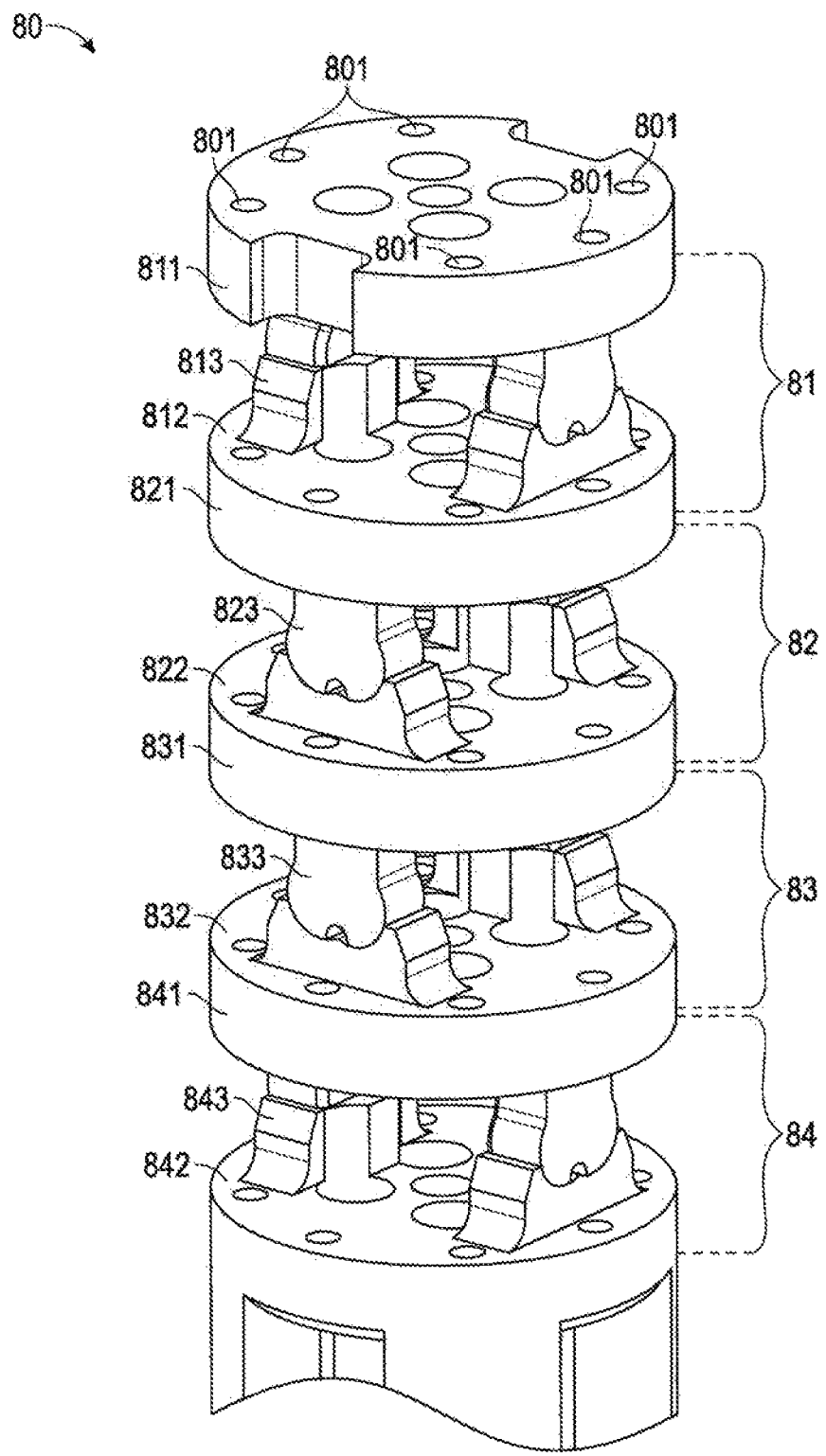
FIG. 35 is a view illustrating an exemplary bending segment according to an exemplary embodiment of the present invention.

In contrast, in this exemplary embodiment, the bending segment may be configured to comprise a series of intermediate joints having tension-regulating members to minimize the slack caused by elongation. FIG. 35 is a view illustrating an exemplary bending segment according to an exemplary embodiment of the present invention. In FIG. 35, the bending segment 80 is illustrated to include four intermediate joints 81, 82, 83, 84 arranged along a longitudinal axis direction of the bending segment. Each intermediate joint 81, 82, 83, 84 has a first link portion 811, 821, 831 and 841 and a second link portion 812, 822, 832 and 842, respectively. Each intermediate joint 81, 82, 83, 84 may be interstacked orthogonally, in parallel or in any angle with the adjacent intermediate joint.

The bending segment 80 further comprises a plurality of lumens 801 passing through each intermediate joint 81, 82, 83, 84. The same number of bending actuation wires (being omitted for clarity) may be thus correspondingly provided to be arranged to pass through each lumen 801 respectively and cause the bending segment 80 to bend.

Each intermediate joint 81, 82, 83, 84 further comprises two tension-regulating member 813, 823, 833 and 843 coupled to the first link portion 811, 821, 831 and 841 and the second link portion 812, 822, 832 and 842. Each tension-regulating member 813, 823, 833 and 843 is configured to compensate for the elongation of the bending actuation wires when bending segments bend, whereby the length of bending actuation wires is altered and kept in a predetermined length.

Figure 36:
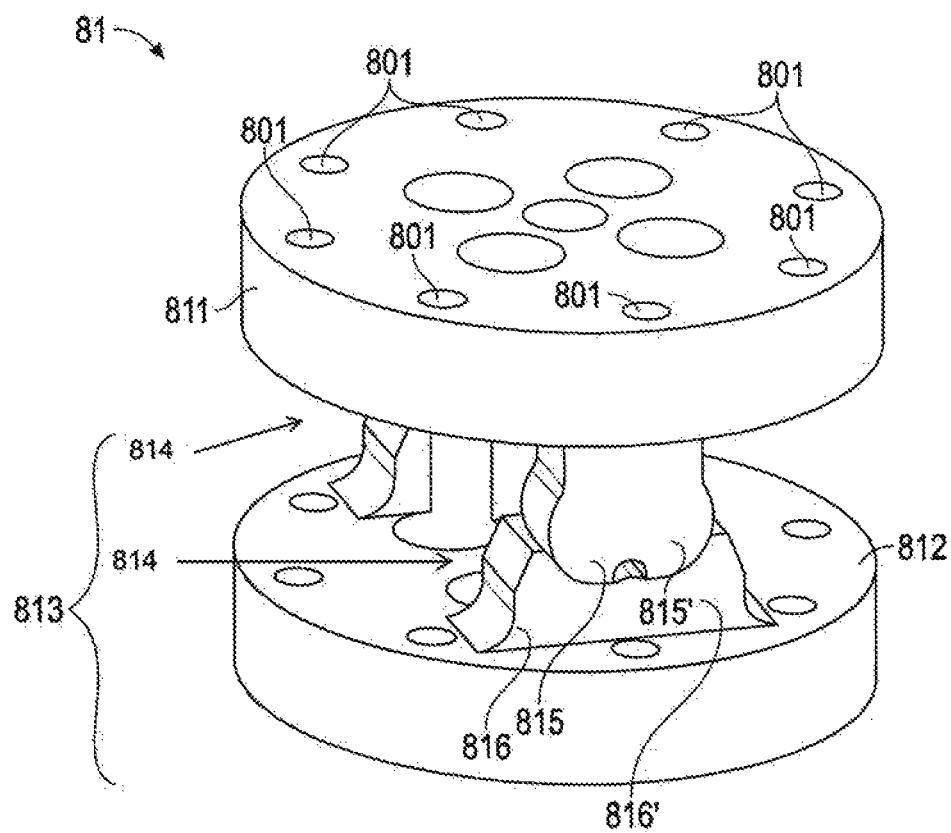
FIG. 36 is a view illustrating an exemplary tension-regulating member in FIG. 35 according to an exemplary embodiment of the present invention.

In FIG. 36, the tension-regulating member 813 is a double-hinged joint comprising two off-axis hinge joints 814. Each off-axis hinge joint 814 comprises a first interfacing half 815, 815' coupled to the first link portion 811 and a second interfacing half 816, 816' coupled to the second link portion 812 and correspondingly pivoted to the first interfacing half 815, 815'. In this exemplary embodiment, each first interfacing half 815, 815' may have a protrusion end, respectively, while the second interfacing half 816, 816' correspondingly may have a recess end. In another exemplary embodiment, each first interfacing half may respectively have a recess end instead, while the second interfacing half correspondingly has a protrusion end.

Figure 37A:
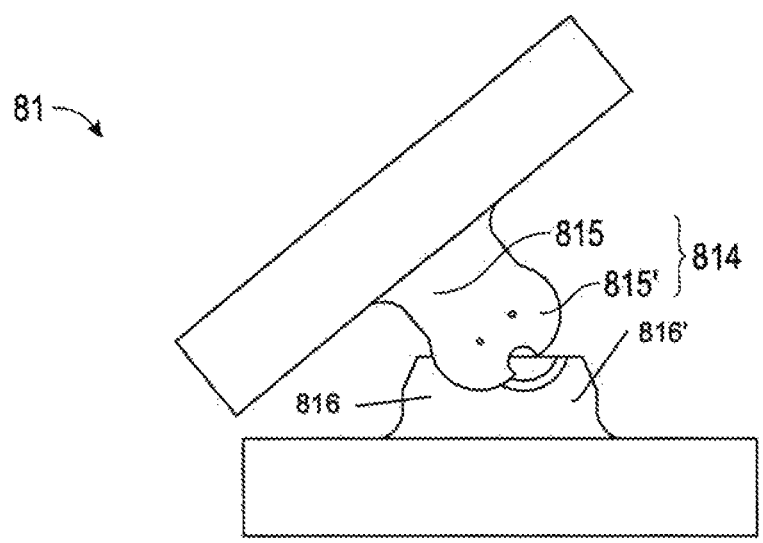
FIG. 37A is a front view of the tension-regulating member bending to the left side.
Figure 37B:
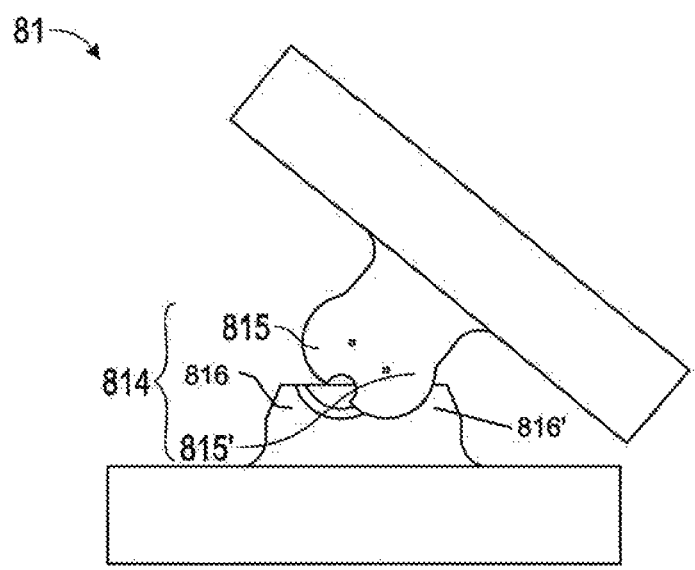
FIG. 37B is a front view of the tension-regulating member bending to the right side.

Pivotal motion will occur on one of the two off-axis hinges 814 depending on bending orientation. FIG. 37 illustrates pivotal motion of one of the tension-regulating member of FIG. 36, wherein FIG. 37A is a front view of the tension-regulating member bending on the left side, and FIG. 37B is a front view of the tension-regulating member bending on the right side. As shown in FIG. 37A, the intermediate joint bends in a bending orientation on the left side on the left hinge 814 which is offset from the longitudinal axis direction, whereby only first interfacing half 815 pivotally moves on the left side. Similarly, only first interfacing half 815' pivotally moves on the right side when intermediate joint 81 bends on the right side as shown in the FIG. 37B.

Figure 38A:
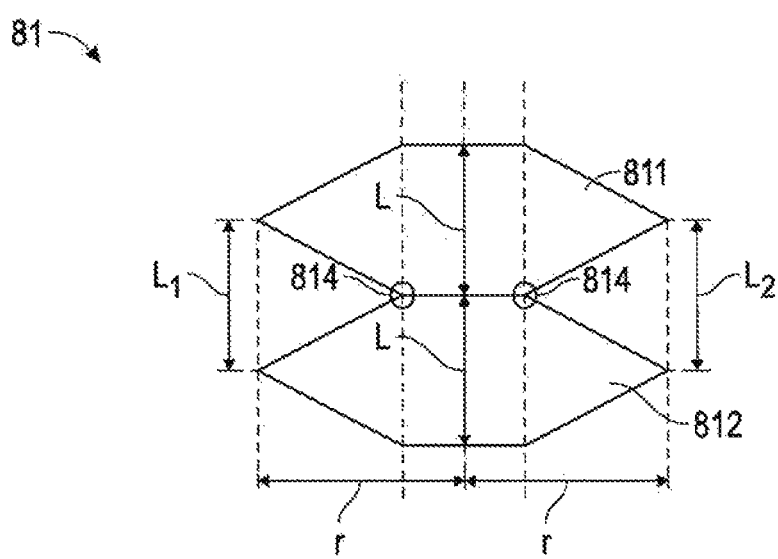
FIG. 38A shows the length of the bending actuation wire before bending.
Figure 38B:
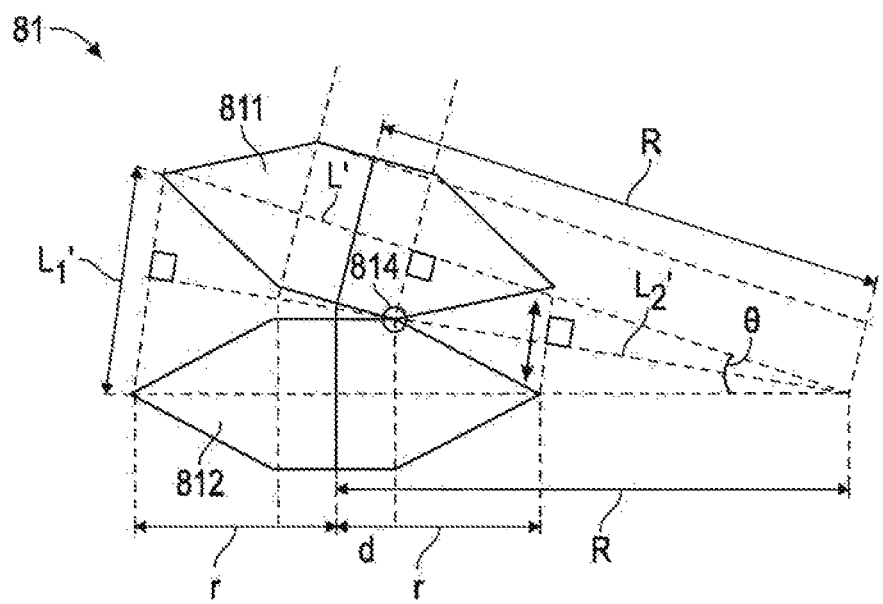
FIG. 38B shows the length of the bending actuation wire after bending.

FIG. 38 is a view schematically illustrating a slack in a wire caused by wire elongation being minimized using the tension-regulating member structure in FIG. 36. FIG. 38 A shows the length of the bending actuation wire before the tension-regulating member structure bends, while FIG. 38 B shows the length of the bending actuation wire after the tension-regulating member structure bends.

In FIGS. 38 A and B, "L" indicates respectively the height of the first link portion 811 or the second link portion 812 along a direction of the central axis of the intermediate joint 81. "$L_1$" indicates the length of a bending actuation wire which passes through the lumen between the left side of the first link portion 811 and the second link portion 812 before bending, while "L1'" indicates the length of the bending actuation wire in the left side after bending. "$L_2$" indicates the length of a bending actuation wire which passes through the lumen between the right side of the first link portion 811 and the second link portion 812 before bending, while "$L_2$'" indicates the length of the bending actuation wire in the right side after bending. "r" indicates a radius from the central axis of each link portion to the lumen that the bending actuation wire passes through. "R" indicates a radius of curvature when the intermediate joint 81 bends and the angle of bend is denoted by "θ". "d" herein indicates a distance from the central axis of each link portion to each off-axis hinge joints 814.

As shown in FIGS. 38 A and B, if wire elongation is ignored in this exemplary embodiment, the total length of the length of the bending actuation wire before and after bending can be represented as the following equation:

$$L_1 = L_2 = L;$$

$$L_1' = 2(R+r)\sin(\theta/2); \quad L_2' = 2(R-r)\sin(\theta/2);$$
$$L_1 = L_2 = L = L' = 2(R-d)\tan(\theta/2);$$

$$L_1 + L_2 = 4(R-d)\tan(\theta/2);$$

$$L_1' + L_2' = 2(R+r)\sin(\theta/2) + 2(R-r)\sin(\theta/2) = 4R\sin(\theta/2);$$

Herein, $R = L/(2\tan(\theta/2)) + d;$ $$\Delta L = (L1 + L2) - (L1' + L2')$$
$$= 2L - 4R\sin(\theta/2)$$
$$= 2L - 4(L/(2\tan(\theta/2)) + d)(\sin(\theta/2)).$$

Figure 39:
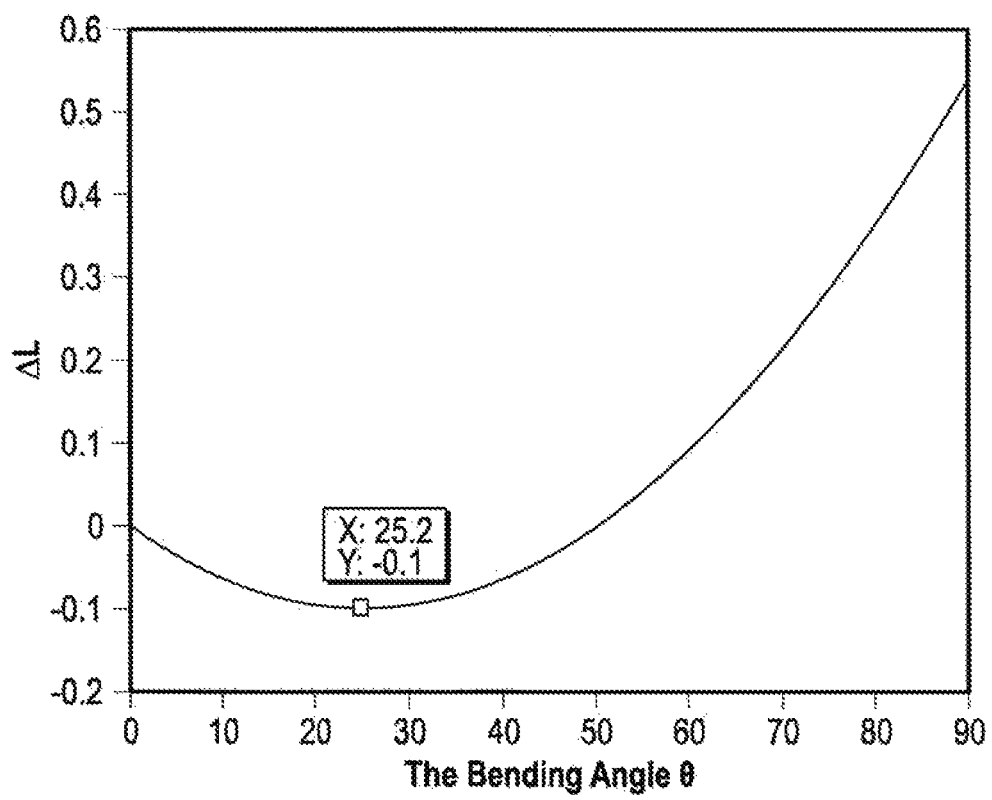
FIG. 39 is a simulation result illustrating that the total length change ($\Delta L$) of the bending actuation wire change as a function of the bending angle $\theta$.

FIG. 39 is a simulation result illustrating the total length change (ΔL) of the bending actuation wires as a function of the bending angle θ calculated using Matlab. For example, when, L=2, d=0.45, ΔL remains <0 when θ is within the range of motion of the designed joint (0 to 45 degrees); so the slack caused by wire elongation can be compensated by ΔL, made possible by off-axis hinge joints.

Thus, pivot motion of the intermediate joint 81 occurs on the hinge 814 located offset from the longitudinal axis direction of the intermediate joint 81. The length of bending actuation wires is altered and kept in a predetermined length in that the elongation of the bending actuation wires is compensated by the off-axis pivot motion.

Figure 40:
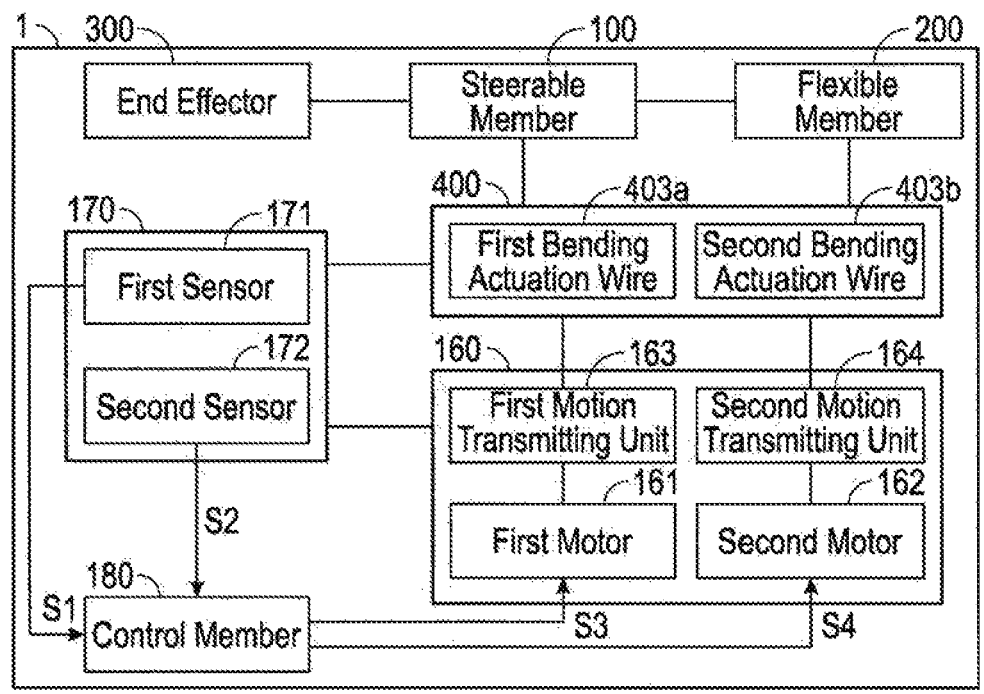
FIG. 40 is a block diagram illustrating a surgical instrument according to an exemplary embodiment of the present invention.
Figure 41:
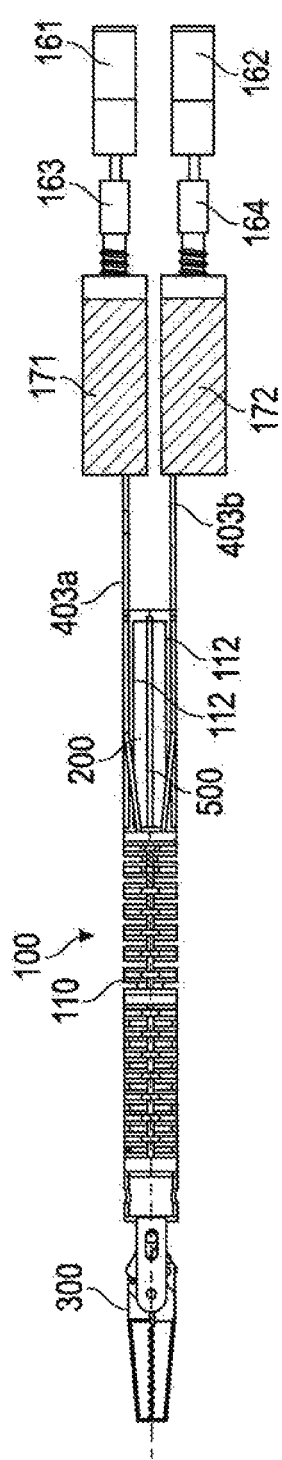
FIG. 41 is a schematic view illustrating a surgical instrument according to an exemplary embodiment of the present invention.

FIG. 40 is a block diagram illustrating a surgical instrument according to an exemplary embodiment of the present invention. FIG. 41 is a schematic view illustrating a surgical instrument according to an exemplary embodiment of the present invention. A steerable member 100 that is bendable is provided at the distal end of the surgical instrument 30.

The steerable member 100 has a plurality of bending segments 110 with hollow channels (not shown in FIGS. 40 and 41) that are connected together. Each bending segment 110 comprises a plurality of lumens 112 that are formed lengthwise. A tubular flexible member 200 comprising a flexible material is provided at the proximal end of the steerable member 100. The tubular flexible member 200 may comprise a hollow tube where various types of wire members connected from the distal end of the surgical apparatus 1 are located. Optionally, an end effector 300 is provided at the distal end of the steerable member 100, and the end effector 300 may be selectively actuated by an effector actuation wire 500 (e.g. see FIGS. 2, 24-26).

Each bending segment 110 of the steerable member 100 is connected to adjacent bending segments in a way that allows hinge movement, and bent by a bending actuation wire 400 (see, e.g. FIG. 2). In this exemplary embodiment, a first bending actuation wire 403a and a second bending actuation wire 403b that are located in separate lumens 112 to pass through the steerable member 100 and the tubular flexible member 200, and the distal ends of the first bending actuation wire 403a and second bending actuation wire 403b are connected to the steerable member 100 and their proximal ends are mechanically connected to a drive member 160. Accordingly, when the first bending actuation wire 403a and second bending actuation wire 403b are moved by the drive member 160, the plurality of bending segments 110 move hingedly, thus causing 1-DOF bending motion of the steerable member 100.

The drive member 160 comprises a first motor 161, a second motor 162, a first motion transmitting unit 163 and a second motion transmitting unit 164. The first motor 161 is coupled to the first bending actuation wire 403a via a first motion transmitting unit 163, so that the power from the first motor 161 may be transmitted to the first bending actuation wire 403a to make it actuate. Similarly, the second motor 162 is coupled to the second bending actuation wire 403b via a second motion transmitting unit 164, transmitting the power from the second motor 162 to actuate the second bending actuation wire 403b. In this exemplary embodiment, the first motion transmitting unit 163 and the second motion transmitting unit 164 may be a lead screw or ball screw, but are not limited to this configuration.

A tension monitoring member 170 is further provided, comprising: a first sensor 171 and a second sensor 172. The first sensor 171 is coupled to the first motion transmitting unit 163 and coupled to the first bending actuation wire 403a. The first sensor 171 may provide a first feedback signal S1 responsive to sensing change in tension force of the first bending actuation wire 403a between the pre-bending and the desired bending motion. Similarly, a second sensor 172 is coupled to the second motion transmitting unit 164 and the second bending actuation wire 403b. The second sensor 172 may provide a second feedback signal S2 responsive to sensing change in tension force of the second bending actuation wire 403b between the pre-bending and the desired bending motion. In this embodiment, the first sensor 171 and the second sensor 172 are load cells, but not limited to this. The change in tension force of the first bending actuation wire 403a or the second bending actuation wire 403b provides an electrical value change (e.g. voltage, current or other parameters) that is calibrated to the load placed on the load cell.

The drive member 160 and the tension monitoring member 170 as described above are further electrically connected to a control member 180. The control member 180 may provide a first output signal S3 responsive to the first feedback signal S1 and transmit to the first motor. Upon receiving the first output signal S3, the first motor 161 will be driven to adjust (i.e. pull or release) the first bending actuation wire 403a. Similarly, the control member 180 may provide a second output signal S4 responsive to the second feedback signal S2, and transmit to the second motor 162 to adjust the second bending actuation wire 403b.

Figure 42:
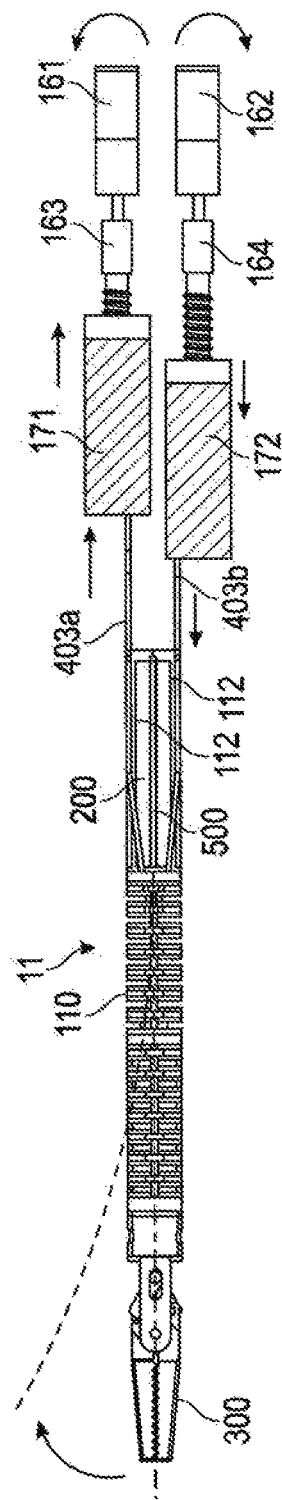
FIG. 42 is a view illustrating a surgical instrument in a bending motion according to an exemplary embodiment of the present invention.

FIG. 42 is a view illustrating a surgical instrument in a bending state according to an exemplary embodiment of the present invention. When the first bending actuation wire 403a is actuated (i.e. pulled toward the direction of the first motor 161 as shown in FIG. 42) in order to bend the steerable member 100, tension of the first bending actuation wire 403a and/or the second bending actuation wire 403b changes because of various reasons. For example, change in the length between before and after bending along the bending direction of the second bending actuation wire 403b is smaller that of the first bending actuation wire 403a. Accordingly, tension of the second bending actuation wire 403b will be changed and backlash will be created due to bending, thus making fine adjustment difficult.

In this exemplary embodiment, the change in tension force caused by the first bending actuation wire 403a can be measured and monitored respectively by the first sensor 171 and the second sensor 172 via the voltage change induced by tension force. Then, the first feedback signal S1 and the second feedback signal S2 are provided to the control member 180 in response to the voltage change. After receiving and processing the first feedback signal S1 and the second feedback signal S2, the control member 180 will provide the first output signal S3 and the second output signal S4 to the first motor 161 and the second motor 162, separately. Then, the first motor 161 will be motionless in response to the first output signal S3, while the second motor 162 will release the second bending actuation wire 403b toward the direction of the steerable member 100 until the predetermined length in response to the second output signal S4, so that the first bending actuation wire 403a and the second bending actuation wire 403b will be maintained under a predetermined tension again.

Figure 43:
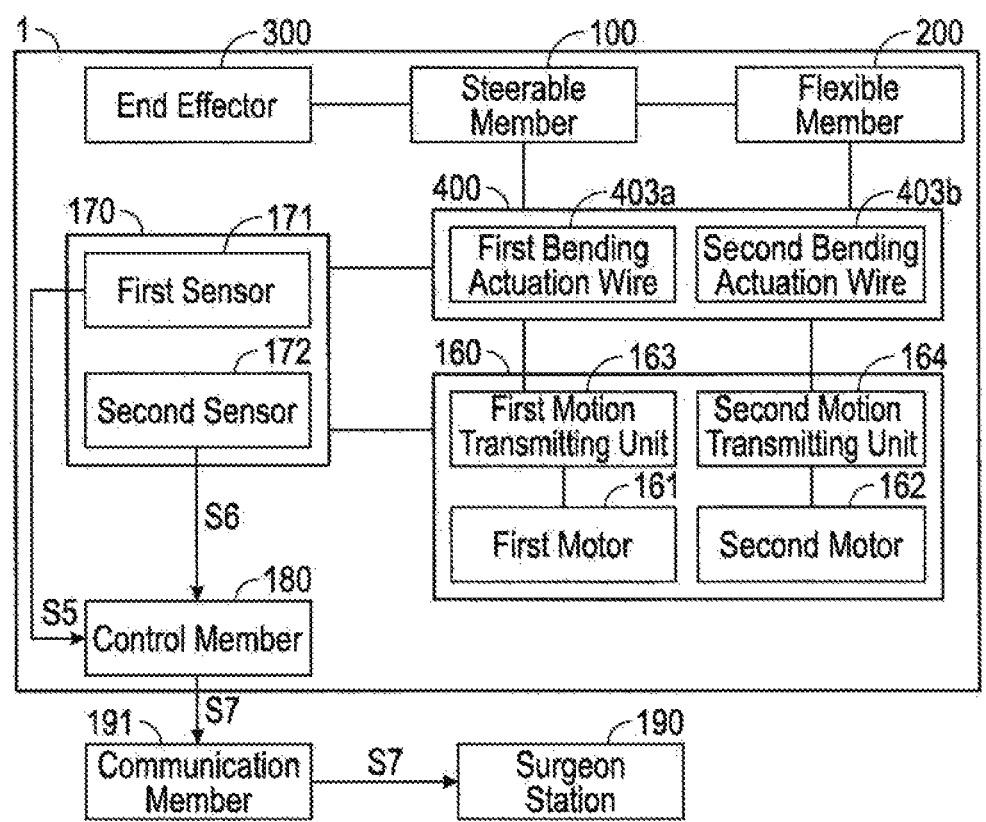
FIG. 43 is a block diagram illustrating a surgical instrument according to another exemplary embodiment of the present invention.
Figure 44:
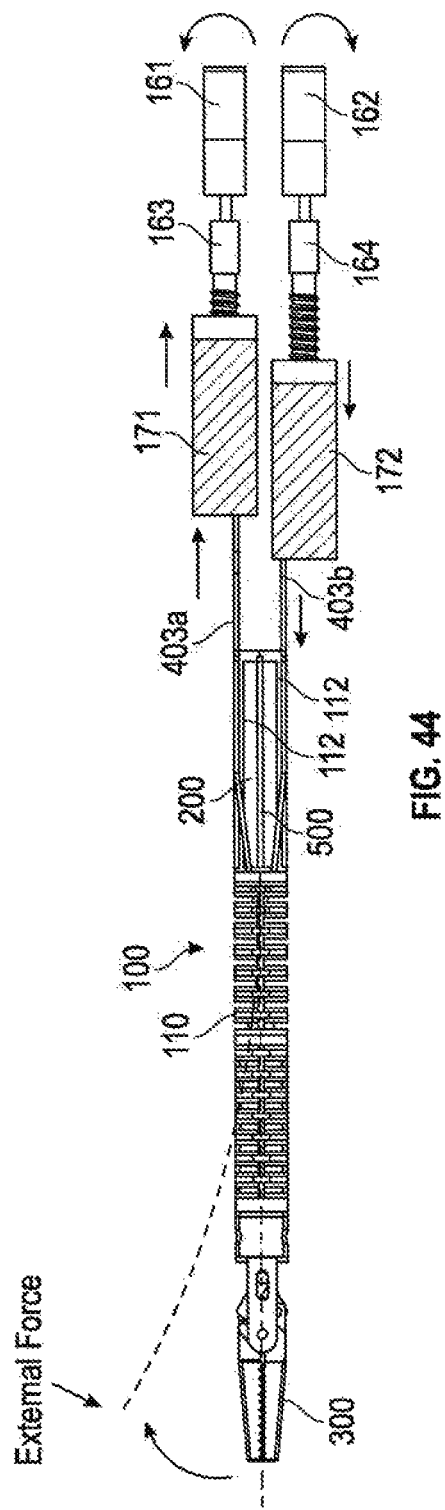
FIG. 44 is a schematic view illustrating a surgical instrument according to another exemplary embodiment of the present invention.

FIG. 43 is a block diagram illustrating a surgical instrument according to another exemplary embodiment of the present invention. FIG. 44 is a schematic view illustrating a surgical instrument according to another exemplary embodiment of the present invention. The end effector 300 may be subjected to various external forces as it is brought into frequent contact with a body wall or creates friction against a body material while being pushed forward along a pathway in the body or creates reaction force when operates the end effector 300. In the traditional surgery, a surgeon feels such external force by their own finger(s). However, in the robotic surgery, surgeons cannot feel the external force directly and all they can do is guess only by their observation or experience.

Thus, in this embodiment, the surgical instrument 30 provided herein may function together with a surgeon station 190 via a communication member 191.

The first sensor 171 and the second sensor 172 as described above may be configured to determine whether an external force is applied or not, depending on whether the potential difference between the sensed value and the value that tension in normal operation applied to the steerable member 100 exceeds a preset threshold value ΔVth. When the external force is determined to be applied, the first sensor 171 and the second sensor 172 will provide a first external-force signal S5 and a second external-force signal S6 respectively to the control member 180. The control member 180 will further provide an instruction signal S7 transmitted via communication member 191 in response to the first external-force signal S5 and the second external-force signal S6.

The communication member 191 may be a build-in one within the control member 180 or an external one. Also, the communication member 191 may use any telecommunication technology in the art. For example, in some embodiments, the communication member 191 may comprise a wireless transmitter and a wireless receiver (not shown in FIGs). In other embodiments, where the signal is digital, or digitized, and modulated by the control member 180, wireless transmitter may be configured according to a standard protocol, e.g., Bluetooth®. Alternatively, any other suitable configuration of hardwired or wireless transmitter, standard or proprietary, may be used. Further, wireless transmitter may include an antenna (not shown) extending therefrom to facilitate transmission of the signal to wireless receiver.

The surgeon station 190 is adapted to be manually manipulated by surgeons to, in turn, control motion of the surgical instrument 30 in response to the surgeons' manipulation. In this embodiment, the surgeon station 190 is configured to display information related to resistance force or vibration in response to the instruction signal S7 to surgeon station 190. In one embodiment, the control member 180 as described above may comprise a haptic feedback controller (not shown in the FIGS) to process and transmit the instruction signal S7 in form of haptic feedback. The haptic feedback may be provided through various forms, for example, mechanosensation, including, but not limited to, vibrosensation (e.g. vibrations), force-sensation (e.g. resistance) and pressure-sensation, thermoperception (heat), and/or cryoperception (cold). The surgeon station 190 may comprise a haptic joystick (not shown in the FIGS) to transfer haptic feedback to the surgeons to inform them of the external force.

In other embodiments, the information related to resistance force or vibration may be shown as graphical information or acoustic information. The surgeon station 190 herein may be various types known in the art that comprises a user's interface to display such graphical information or acoustic information. With the surgical instrument 30 provided herein, the external force may be detected and monitored by the tension monitoring member 170 and be displayed in a visualized form or be sensed by haptic feedback. Thus, surgeons can apply additional force using master device in the surgeon station timely against the external force, even in a tele-operation condition. Also, the accuracy to perform surgeries using the surgical instrument 30 will be increased.

In a further aspect, the present invention further provides a personalized master controller for use with robots and the like, and particularly to robotic surgical devices, systems, and methods. In robotically assisted surgery, the surgeon typically operates a master controller to remotely control the motion of robotic surgical devices at the surgical site. The master controller may be separated from the patient by a significant distance (e.g., across the operating room, in a different room, or in a completely different building than the patient). Alternatively, a master controller may be positioned quite near the patient in the operating room. Regardless, the master controller will typically include one or more manual input handles so as to move a surgical apparatus 1 as shown in FIG. 1 based on the surgeon's manipulation of the manual input handle. Typically, the manual input handle may be designed so as to allow smooth motion in the six degrees of freedom which may correspond to translations in three axes, as well as rotation in three axes.

Further, in order to drive the surgical instrument 30 to perform various surgical operations, the manual input handle itself may provide a degree of freedom for gripping motion. For example, a built-in gripping device may be further provided at the proximal end of the manual input handle, so that the gripping device may be levered to allow an operator to emulate the motion of scissors, forceps, or a hemostat and control actuation of surgical instrument 30, such as, to actuate the end-effector 300 (see FIG. 1) to move tissue and/or other material at the surgical site by gripping the same. However, such a gripping device may not be replaceable, and thus operators have no choice but are forced to use the manual input handle with the gripping device that they may not very familiar with. Precise control using a master controller for surgical operations may thus become more difficult.

Figure 45:
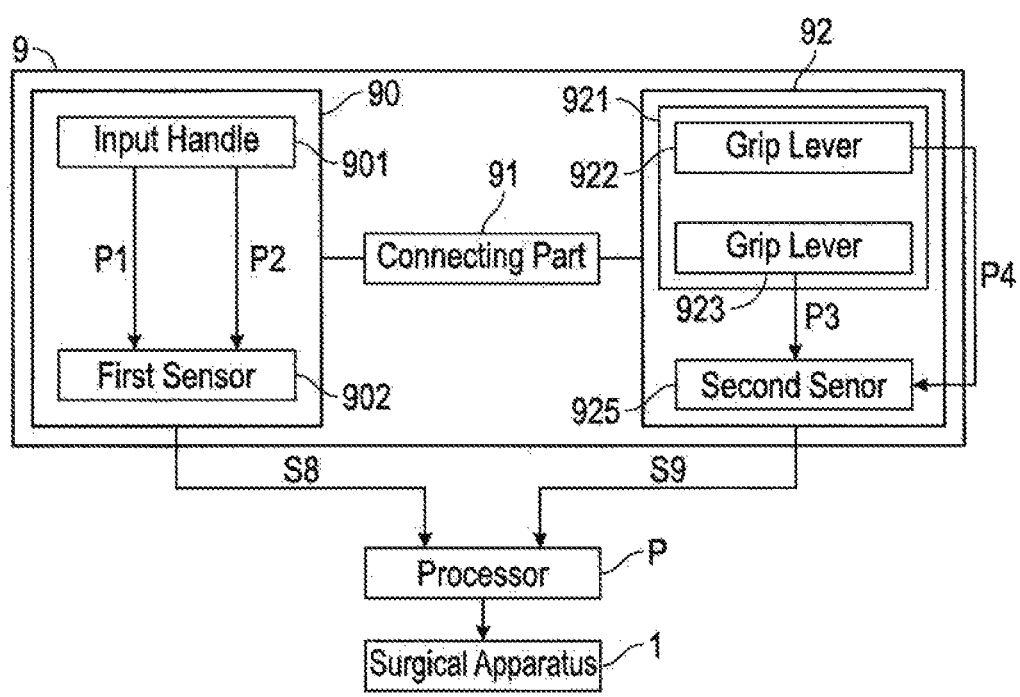
FIG. 45 is a block diagram illustrating a personalized master controller according to an exemplary embodiment of the present invention.

For the reasons outlined above, it would be advantageous to provide improved devices, systems, and methods for robotic surgery, telesurgery, and other telerobotic applications. In an exemplary embodiment, a personalized master controller is provided herein. FIG. 45 is a block diagram illustrating a personalized master controller according to an exemplary embodiment of the present invention. The personalized master controller 9 may be coupled to a processor P (e.g. a computer) that is electrically connected to the surgical apparatus 1. As provided herein, the personalized master controller 9 may comprise a control platform 90, a connecting part 91, and an interchangeable grip 92. As shown in FIG. 45, the control platform 90 may be configured to define and input one or more movement signals to control movement of the surgical apparatus 1 (see, e.g. FIG. 1) via the processor P.

Figure 46:
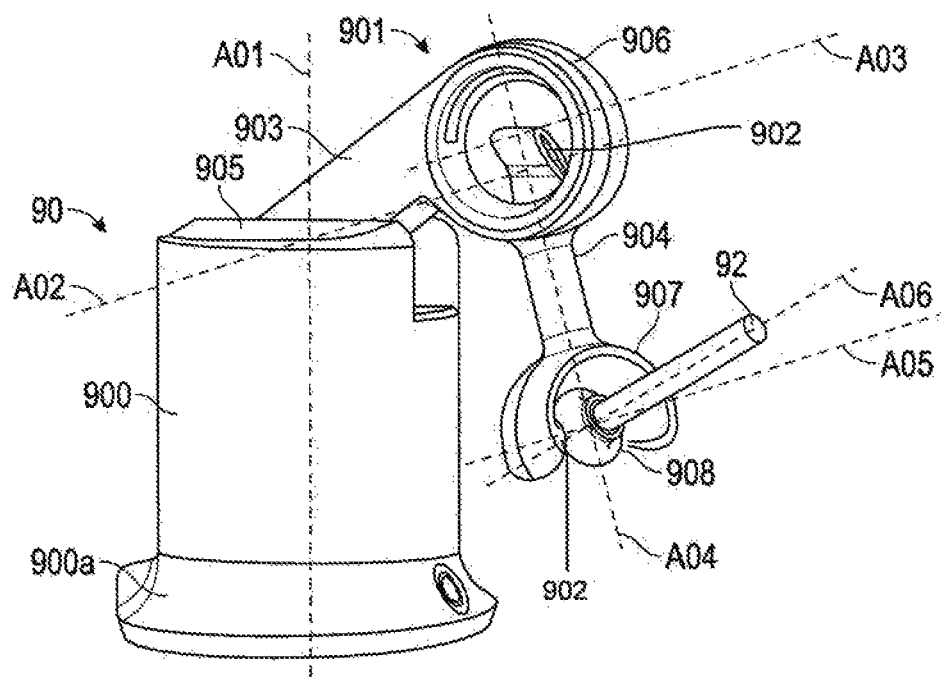
FIG. 46 is view schematically illustrating a personalized master controller according to an exemplary embodiment of the present invention.

In some alternative embodiments, the control platform 90 may be a serial manipulator, comprising: a number of rigid links connected with joints as described in U.S. Pat. Nos. 7,714,836, 7,411,576, and 6,417,638, which are incorporated herein by reference in their entirety. For example, as shown in FIG. 46, this type of the control platform 90 may comprise: a body 900 comprising a base 900a, an input handle 901 and a first plurality of sensors 902. The base 900a may rotate with respect to a first axis A01 having a substantially vertical orientation. The input handle 901 may comprise a first link 903, a second link 904 and a gimbal structure comprising an outer gimbal 907 and an inner gimbal 908. The first link 903 is pivoted to the body 900 via a first joint 905 which allows the first link 903 to move with respect to a second axis A02 having a substantially perpendicular orientation relative to the first axis A01. The second link 904 is pivoted to the first link 903 via a second joint 906 which allows the second link 904 to move with respect to a third axis A03 which is substantially parallel to the second axis A02.

Figure 48A:
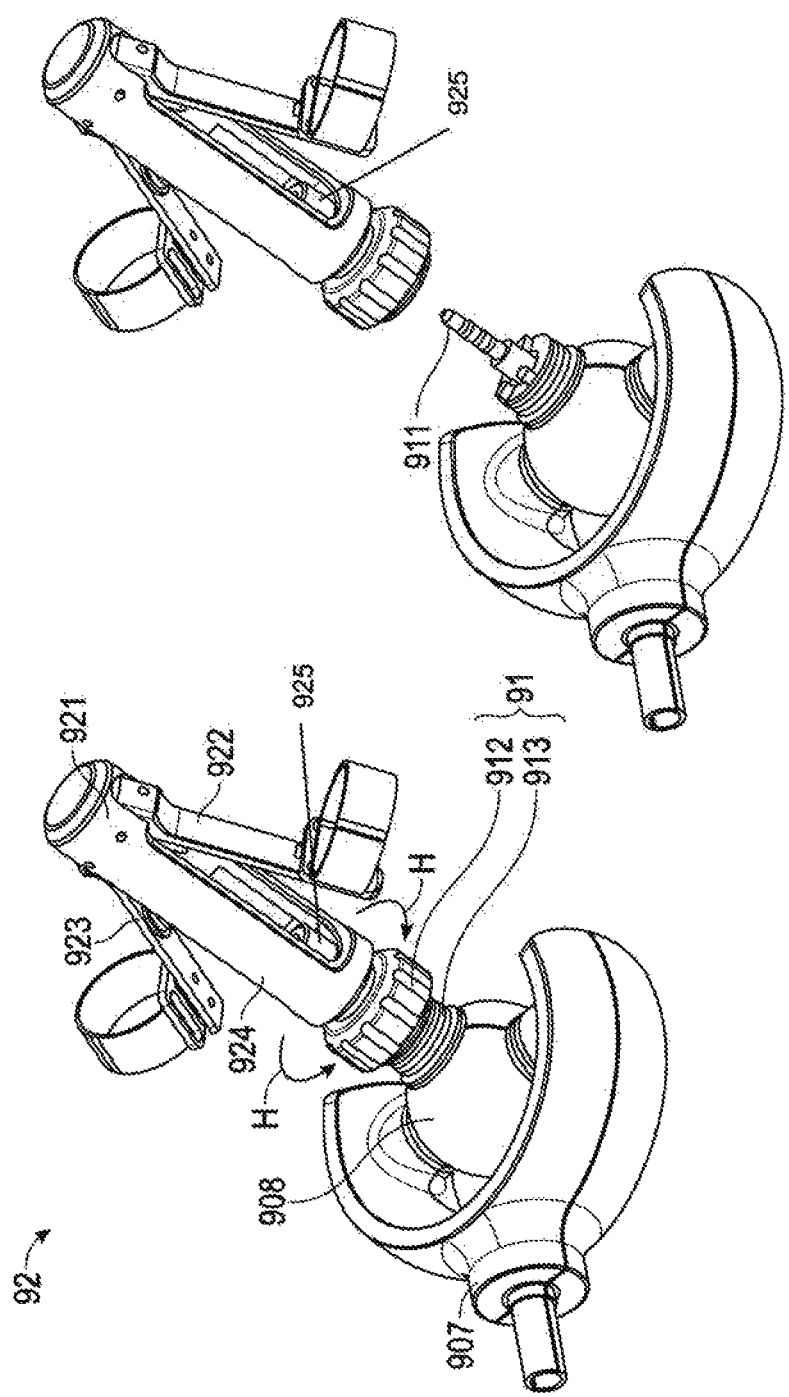
FIG. 48A is a grip-type one.

A gimbal structure is mounted to the free end of the second link 904 comprising an outer gimbal 907 and an inner gimbal 908. The outer gimbal 907 is pivotally supported by the second link 904 and allowed to rotate with respect to a fourth axis A04 which is substantially perpendicular to the third axis A03. The inner gimbal 908 is pivotally supported by the outer gimbal 907 and allowed to rotate with respect to a fifth axis A05 which is substantially perpendicular to the fourth axis A04. A connecting part 91 (FIG. 48A) is mounted on the inner gimbal structure 908 and allows the interchangeable grip 92 that is electrically connected thereto to rotate with respect to a sixth axis A06.

Figure 47:
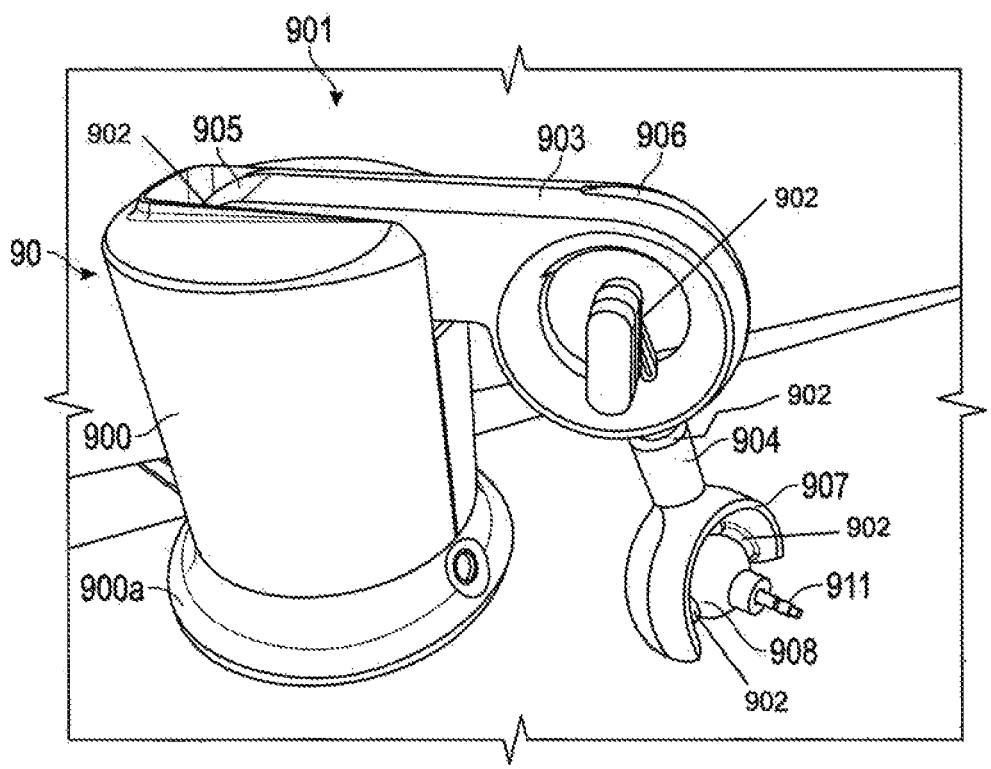
FIG. 47 is view schematically illustrating a control platform and a connecting part according to an exemplary embodiment of the present invention.

The connecting part 91 mounted on the inner gimbal structure 908 electrically connects the input handle 901 and the interchangeable grip 92. FIG. 47 is a perspective view illustrating a connecting part connected to the control platform according to an exemplary embodiment of the present invention. In one embodiment, the connecting part 91 may be a plug-and-socket type connector, but not limited to this. As shown in FIG. 47, in one embodiment, a one-prong plug 911 of the connecting part 91 may be coupled to the inner gimbal 908 while a corresponding socket structure 912 may be mounted at the distal end of the interchangeable grip 92 (see FIG. 48), such that the interchangeable grip 92 can be connected to on the inner gimbal structure 908 and be allowed to rotate with respect a sixth axis A06 which is substantially perpendicular to the fifth axis A05. Alternatively, in some embodiments, the one-prong plug 911 of the connecting part 91 may be coupled to the distal end 924 of the interchangeable grip 92 while the socket structure 912 may be mounted the inner gimbal 908 (see FIG. 48).

Thus, the control platform 90 can provide six degrees of freedom movement including three translational degrees of freedom (in X, Y, and Z directions) and three rotational degrees of freedom (in pitch, yaw, and roll motion). The input handle 901 thereby can provide a plurality of position parameters P1 when it is translatable itself or with the mounted interchangeable grip 92 in X, Y, and Z direction with respect to the control platform 90 and/or provide a plurality of orientation parameters P2 when it is rotatable itself or with the mounted interchangeable grip 92 in pitch, yaw, and roll motion with respect to the control platform 90.

In one embodiment, one or more first sensors 902 may be mounted to the input handle 901 and configured to and generate one or more first movement signals S8 in response to the above-mentioned position parameters P1 and/or the orientation parameters P2. The first sensors 902, may, for example, be mounted to the first joint 905, the second joint 906 and/or the gimbal structure 907. In some embodiments, the first sensors 902 may be any type of sensors capable of measuring the position parameters P1 and/or the orientation parameters P2 based on the status or changes such as position, orientation, force, torque, speed, acceleration, strain, deformation, magnetic field, angle and/or light (but not limited to this) caused by the motion of the input handle 901 and/or mounted interchangeable grip 92. For example, the first sensors 902 may be pressure or force sensor, including but not limited to a piezoelectric sensor, a simple piezoelectric crystal, a Hall-Effect or a resistive strain gauge sensor, etc., all of which can be either stand-alone or integrated with signal-conditioning electronics (Wheatstone bridge, low-noise amplifier, A/D converter, etc.) into a single chip or single package sealed module. In other embodiments, may be an angle sensor, or a rotational sensor, but not limited to this. In a specific embodiment, the first sensor 902 may be a Hall-Effect sensor. As known in the art, the Hall-Effect sensor may be used in the presence of a corresponding magnet element (not shown in the FIGS.) to sense the magnetic field responding to the position parameter P1 and/or the orientation parameter P2. Then, the first sensors 902 may produce a first movement signal S8 to control movement of the surgical apparatus 1 (e.g., roll, translation, or pitch/yaw movement) accordingly.

Figure 48C:
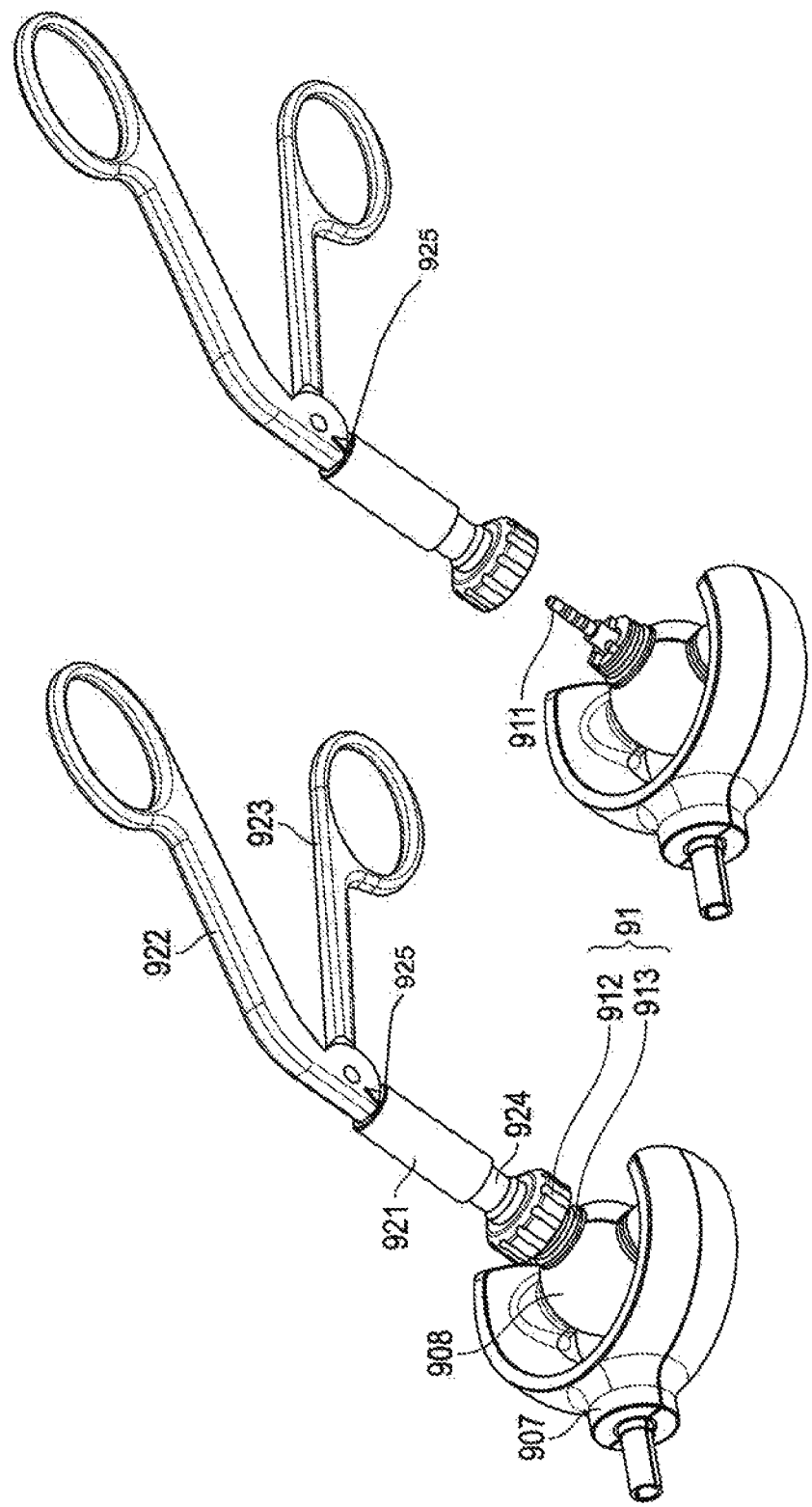
FIG. 48C is a laparoscopic-hand-instrument type one.

FIG. 48 is a perspective view illustrating an interchangeable grip according to an exemplary embodiment of the present invention. In one embodiment, the interchangeable grip 92 provided herein may comprise a detachable handle 921 to mimic actual handles from manual surgical instruments. i.e., it may be the same size and shape, and can be squeezable or fixed, in order to provide realism to the surgeon. For example, two grip levers 922, 923 shown in FIG. 49. A may be pivoted at the proximal end of the detachable handle 921 so as to provide a degree of freedom of pinching or grasping motion. Both grip levers 922, 923 may be allowed to move toward each other relative to the detachable handle as indicated by arrows H to provide a degree of freedom of pinching or grasping motion. To mimic actual standard surgical handles depending on a field, surgeon, or operation, the detachable handle 921 and grip levers 922, 923 may be designed to be interchangeable as various types of surgical tools such as tweezers or laparoscopic hand Instruments as shown FIG. 48B and FIG. 48C, respectively.

Also, in some embodiments, the detachable handle 921 may be mounted to or detach from the socket structure 912 at its distal end 924. The socket structure 912 provided herein may be capable of electrically connecting to or disconnecting from the one-prong plug 911 of the connecting part 91, so that the detachable handle 921 may be instrumented accordingly to receive relevant gripping motion input from the surgeon and the corresponding control signals are subsequently produced and transmitted to the surgical apparatus 1 via the control platform 90.

To sense gripping motion of the interchangeable grip 92, in one embodiment, the detachable handle 921 may define an inner hollow tubular space where a second sensor 925 may be housed to sense at least one parameter P3 based on the status or changes such as position, orientation, force, torque, speed, acceleration, strain, deformation, magnetic field, angle and/or light (but not limited to this) caused by the motion of the grip levers 922, 923.

In some embodiments, the second sensor 925 may be any type of sensors known in the art. For example, the second sensors 905 may be pressure or force sensor, including but not limited to a piezoelectric sensor, a simple piezoelectric crystal, a Hall-Effect or a resistive strain gauge sensor, etc., all of which can be either stand-alone or integrated with signal-conditioning electronics (Wheatstone bridge, low-noise amplifier, A/D converter, etc.) into a single chip or single package sealed module. In other embodiments, the second sensors 925 may be an angle sensor, or a rotational sensor, but not limited to this. In a specific embodiment, the second sensor 902 may be a Hall-Effect sensor. The Hall-Effect sensor may be used in the presence of a corresponding magnet element (not shown in the FIGS.) to sense the magnetic field as known in the art, such that the Hall-Effect sensor may measure the gripping parameters P3 and/or P4 based on the status or changes of the magnetic field caused by the motion of the grip levers 922, 923. Then, the Hall-Effect sensor may produce a second movement signal S9 that can control the movement of the end-effector 300 shown in FIG. 1 accordingly. (e.g. opening and closing (gripping) movement of the end-effector 300 that may be a gripping device (e.g., jaws or blades).)

Figure 49:
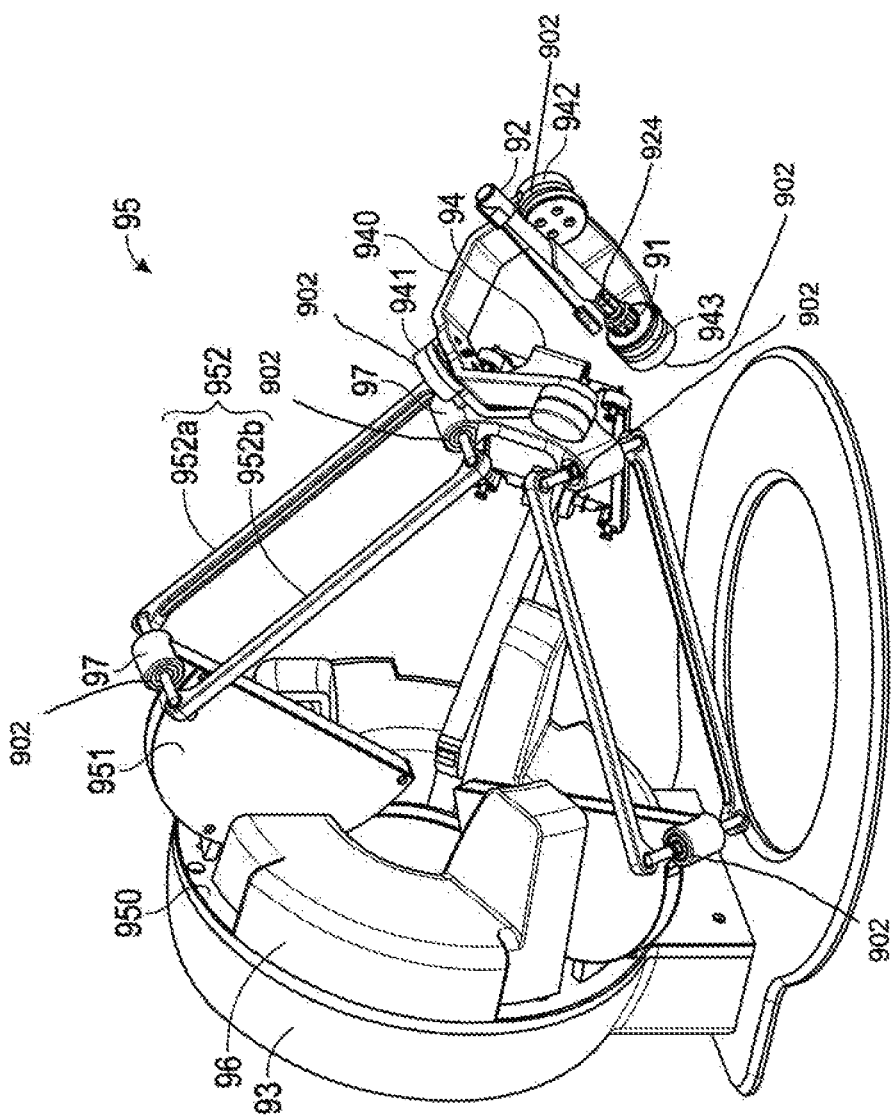
FIG. 49 is view schematically illustrating a personalized master controller according to another embodiment of the present invention.
Figure 50:
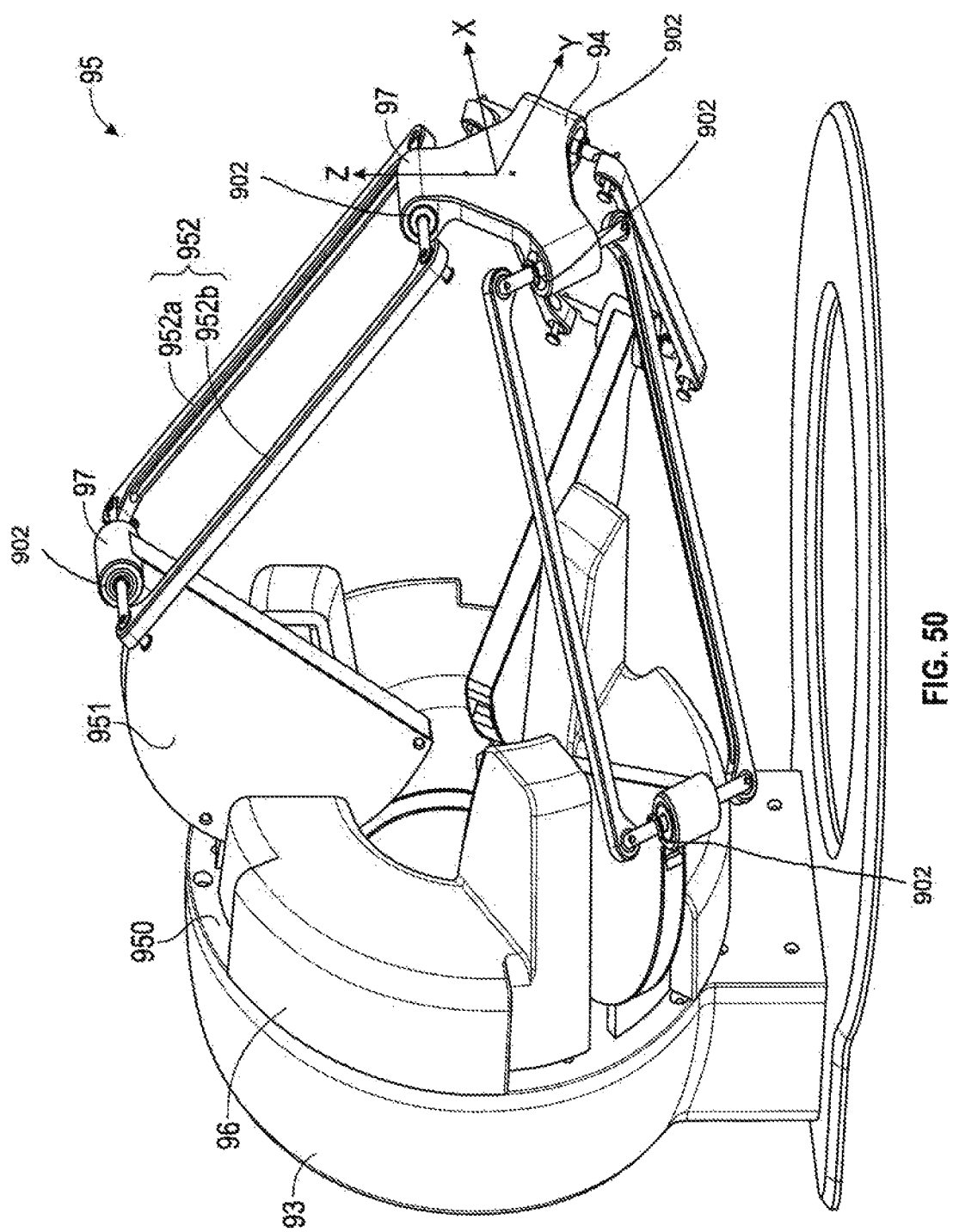
FIG. 50 is view schematically illustrating parts (i.e. the base member, the moveable member, and three parallel kinematics chain) of the control platform of the personalized master controller in FIG. 49.

FIG. 49 is a view schematically illustrating a personalized master controller according to another exemplary embodiment of the present invention. FIG. 50 is view schematically illustrating parts of the control platform of the personalized master controller in FIG. 49. In this embodiment, the control platform 90 may be a device comprising parallel kinematics structures, in particular, a Delta parallel kinematics structure device (for example, as described in US 2008/0223165 A1 which is incorporated herein by reference in its entirety.). As shown in FIG. 49, the control platform 90 is adapted to provide up to six degrees of freedom (i.e. up to three translational degrees of freedom in X, Y, and Z directions and up to three rotational degrees of freedom in pitch, yaw, and roll orientations to provide a position parameter and an orientation parameter, respectively.

In this embodiment, the control platform 90 may comprise: a base member 93, a moveable member 94, and three parallel kinematics chains 95 coupling the base member 93 and the moveable member 94, respectively. Each parallel kinematics chain 95 having a first arm 951 moveable in a respective movement plane 950 which is at a distance to a symmetry axis (i.e. the central line perpendicular to the base member 93). Each first arm 951 is coupled with its associated mounting member 96 such that each first arm 951 may be rotated or pivoted with respect to the associated mounting member 96 and, thus, with respect to the base member 93.

The parallel kinematics chains 95 comprising a second arm 952 may be coupled to the moveable member 94. Each second arm 952 may be considered as parallelogram including two linking bars 952a, 952b. At proximal end of the second arm 952, each linking bar 952a and 952b may be coupled with the moveable member 94 by a joint or hinge 97. At the distal end of the second arm 952, each linking bar 952a, 952b are coupled with an end of its associated first arm 951 by a joint or hinge 97. Each second arm 952, particularly each linking bar 952a, 952b, may have two rotational degrees of freedom at both ends.

Thus, each kinematics chain 95 connected between the base member 93 and the moveable member 94 may be moved in a movement space defined by the base member 93, the moveable member 94, and three parallel kinematics chains 95 to provide up to three translational degrees of freedom (along the X, Y, and Z directions, respectively as shown in FIG. 50), generating one or more position parameters P1. More details for the Delta parallel kinematics structure device may be referred to, for example, US 2008/0223165 A1 which has been incorporated herein by reference in its entirety.

In addition, up to three rotational degrees of freedom may be provided by a wrist structure 940 coupled to the moveable member 94, comprising a three pivotable connections 941, 942 and 943, for example in form of pivot joints. Each of the pivotable connections 941, 942 and 943 provides a rotational degree of freedom with respect to the moveable member 94 (in yaw, pitch, and roll orientations respectively in FIG. 51), and generates one or more orientation parameters P2 thereby.

There are a plurality of first sensors 902 provided to detect one or more position parameters P1 and/or the orientation parameters P2 caused by the movement of three parallel kinematics chains 95 and the moveable member 94, followed by generating first movement signals S8 in response to the parameter(s) P1 and or P2. For example, some first sensors 902 may be installed to each mounting member 96 respectively to detect at least one parameter caused by the motion of the associated first arm 951. Other first sensors 902 may be installed to all or parts of joint or hinge 97 respectively to detect at least one parameter caused by the motion of the associated second arm 952. Alternatively, three first sensors 902 may be provided at three pivotable connections 941, 942 and 943 respectively.

Figure 51:
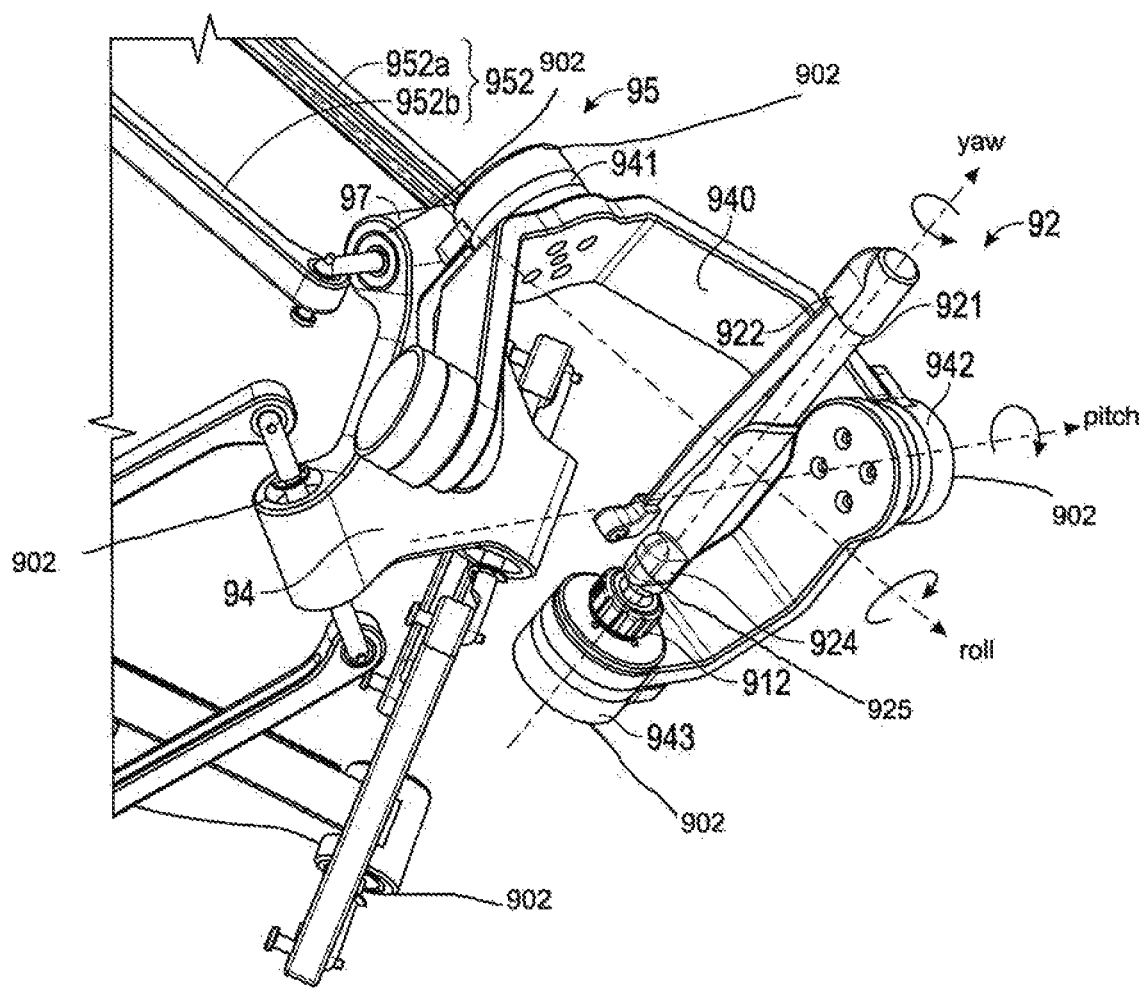
FIG. 51 is an enlarged view of a portion of FIG. 49 showing the interchangeable grip being attached to the moveable member of the control platform according to an exemplary embodiment of the present invention.
Figure 52:
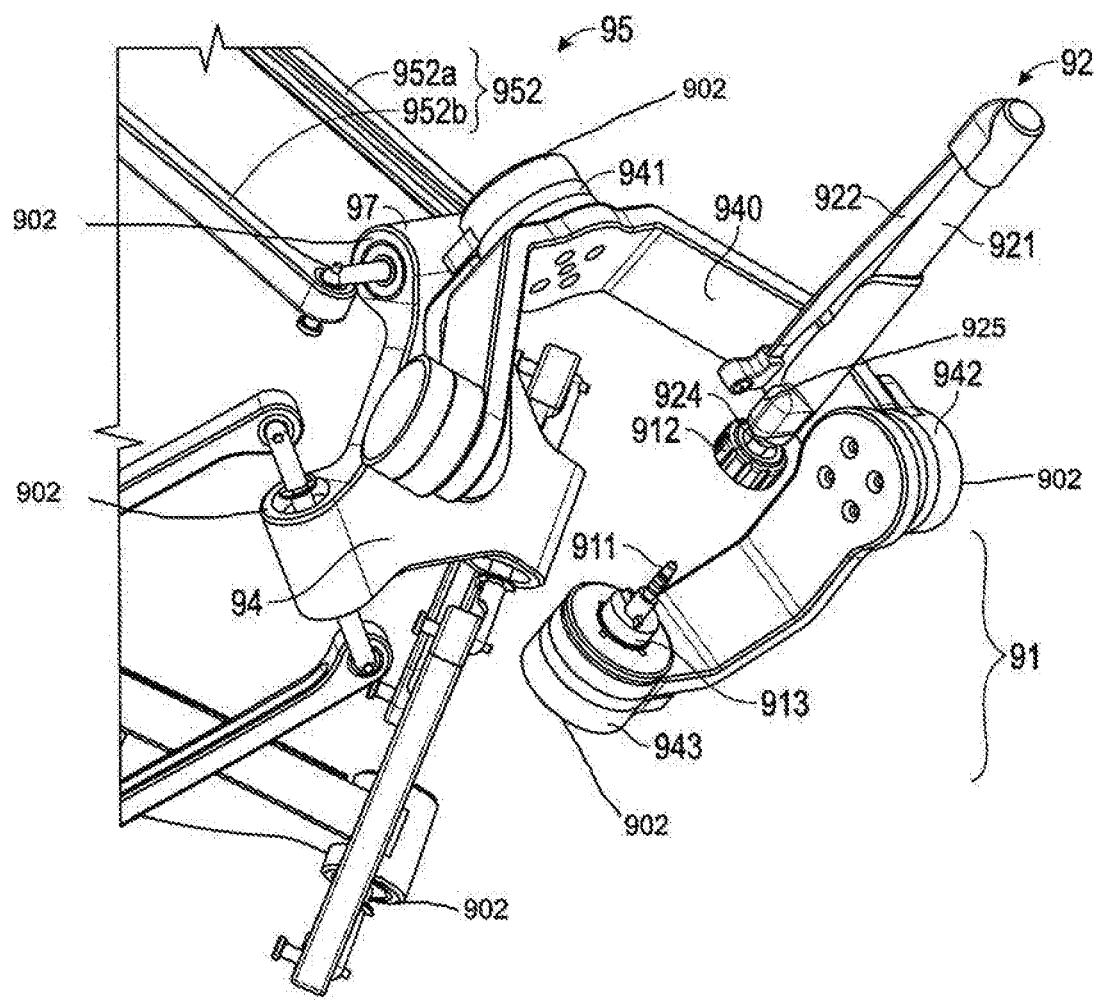
FIG. 52 is an enlarged view of a portion of FIG. 49 showing the interchangeable grip being detached from the moveable member of the control platform according to an exemplary embodiment of the present invention.

FIG. 51 is an enlarged view of a portion of FIG. 49 showing the interchangeable grip being attached to the moveable member of the control platform according to an exemplary embodiment. FIG. 52 is also an enlarged view of a portion of FIG. 49 showing the interchangeable grip being detached from the moveable member of the control platform according to an exemplary embodiment. As shown in FIG. 52, a connecting part 91 is further mounted on the pivotable connection 943, such that it can electrically connect the input handle 901 and the interchangeable grip 92. As shown in FIG. 52, in one embodiment, the connecting part 91 may comprise be a plug-and-socket type connector, but not limited to this. For example, a one-prong plug 911 of the connecting part 91 may be coupled to the detachable handle 921 of the interchangeable grip 92 via a thread 913, while a corresponding socket structure 912 may be mounted at the pivotable connection 943, so that that the interchangeable grip may be attached to (see FIG. 51) or detached from (see FIG. 52) the pivotable connection 943 and allowed to rotate with respect to the rotational axis A10 of the pivotable connection 943.

FIGS. 53 to 66 schematically illustrate the surgical tool hereof, configured for use in an esophageal endoscopic procedure, for example the removal of a lesion on the wall of the esophagus, followed by suturing the site closed using the end effector(s) of the surgical tool in situ. Herein, the surgical tool comprises a plurality of tubular flexible members 200, each extendable in a surrounding sheath 202 dedicated thereto (FIG. 55), each surrounding sheath 202 and tubular flexible member 200 extending within an outer sheath 1162, the flexible tubing terminating in a steerable member 100 (FIG. 56) and an end effector at the distal end thereof, and each tubular flexible member 200 is connected at the proximal end thereof to a driving part 40 dedicated thereto. Additionally, the insertion tube 1002 of a traditional endoscope 1000, as shown schematically in FIG. 54, likewise extends through the outer sheath 1162. Each of the surrounding sheaths 202 and the insertion tube 1002 of the endoscope 1000 terminate within, and are supported at their distal end, in a distal coupler 1140. The outer sheath 1162 extends over and tightly fits on the first end of the distal coupler 1140, the surrounding sheaths 202 terminate within the distal coupler 1140, and the outer sheath 1162 and distal coupler 1140 together comprise the outer surfaces of the introduction portion 1004 of the surgical tool. The distal coupler 1140 is manufactured of stainless steel or another biocompatible material, and it serves to relatively position the ends of the tubular flexible members 200, surrounding sheaths 202 and insertion tube 1002 relative to each other. The outer sheath 1162, surrounding sheaths 202 and flexible tubular flexible members 200 are manufactured from a bio-compatible polymer which is bendable for relatively easy insertion thereof into the body lumen of a patient. In some embodiments, a third flexible sheath (not shown in the drawing) may be further provided, having a proximal end and a distal end, the third flexible sheath surrounding a portion of, the at least one bendable endoscope 1000 e.g. the insertion tube 1002, the proximal end of the third flexible sheath fixed in position with respect to the mechanical carriage 1100 and the distal end connected to the distal coupler 1140.

Figure 53:
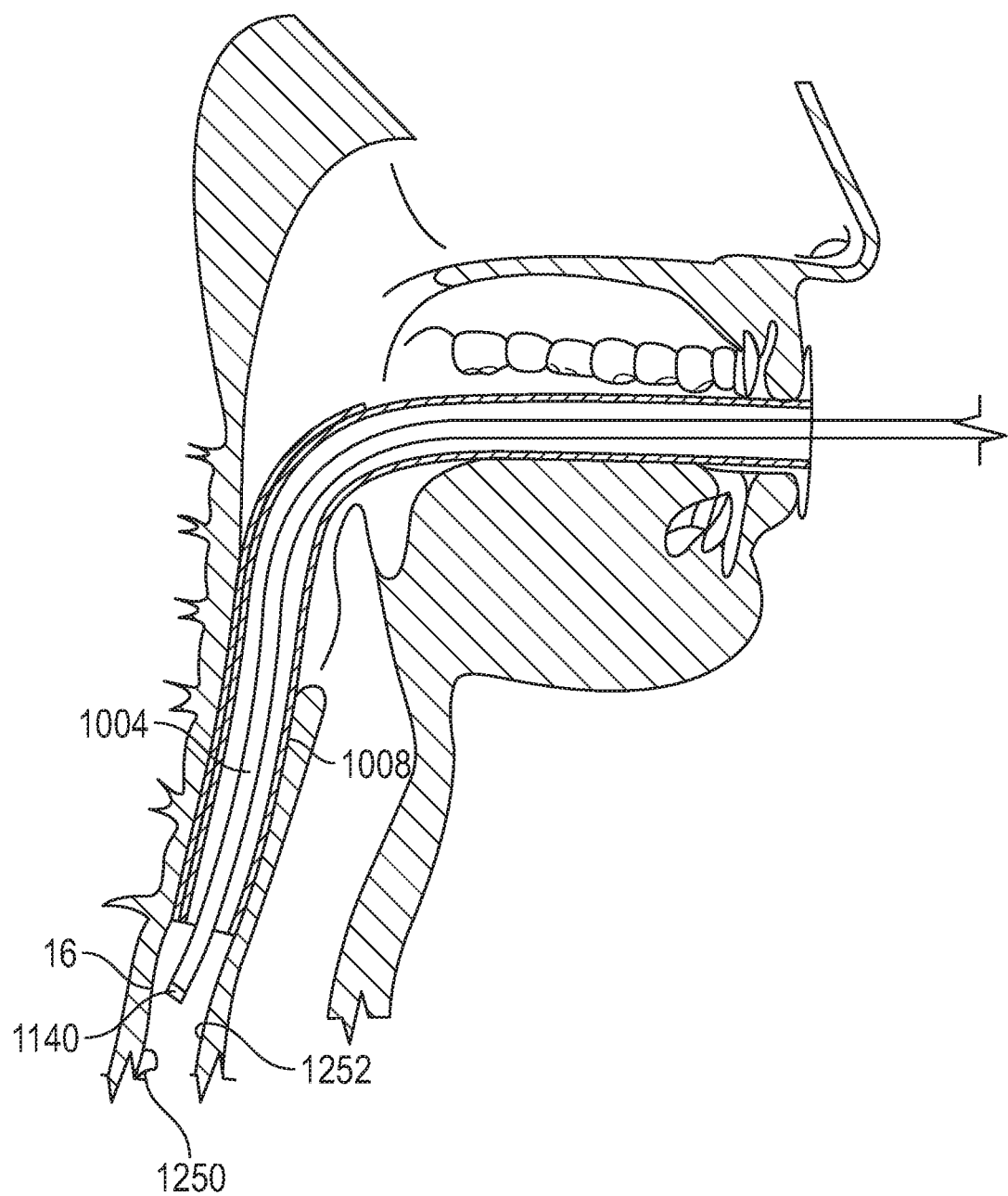
FIG. 53 is a schematic sectional view of a human mouth and esophagus, showing an introduction tube and the surgical device hereon inserted therein.

As shown in FIG. 53, after a patient is intubated and an introduction tube 1008 is introduced into the throat, the introduction portion 1004 is introduced through the introduction tube 1008, such that the distal coupler 1140 is located outwardly of the introduction tube 1008 and within the esophagus of the patient. The surgeon or other operator steers the introduction portion 1004 to this position using the camera 1012 (see FIG. 56) connected to the traditional endoscope to locate a location of interest along the patient's esophagus. Thereafter, the tubular flexible members 200 are extended from the distal coupler 1140 using the driving part 40 (see, e.g. FIG. 54), and the steerable members 100 on their ends are oriented by proper tensioning or pulling of bending actuation wires 400, to perform a surgical procedure at the location of interest.

Figure 54:
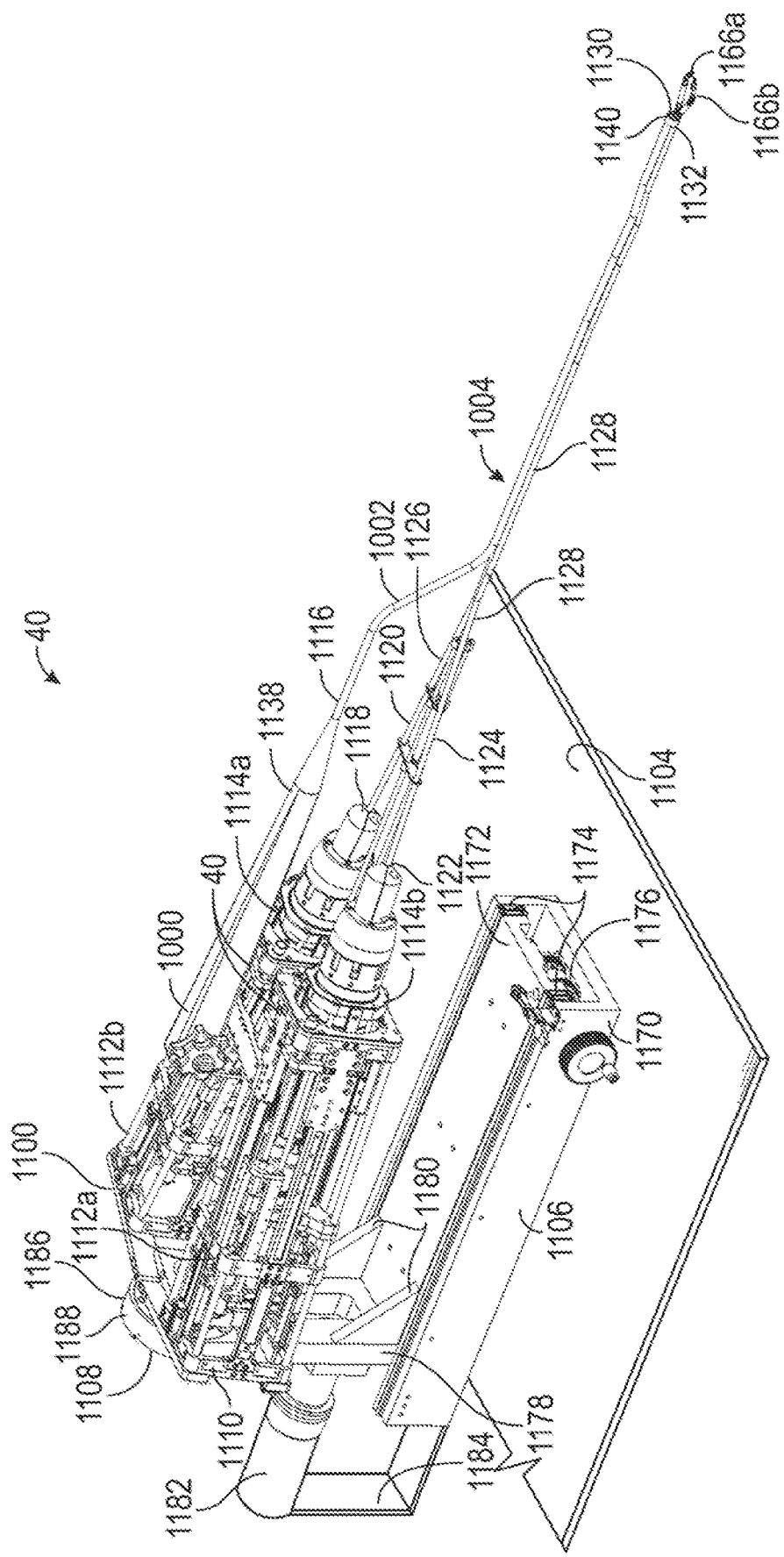
FIG. 54 is an isometric view of a positioning and control device for positioning the surgical device hereof.
Figure 55:
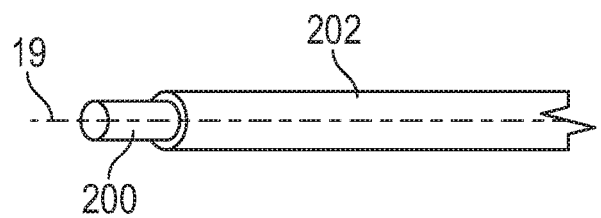
FIG. 55 is a schematic perspective view of a hollow member for a robotic arm of the surgical device hereof and a sheath.
Figure 60:
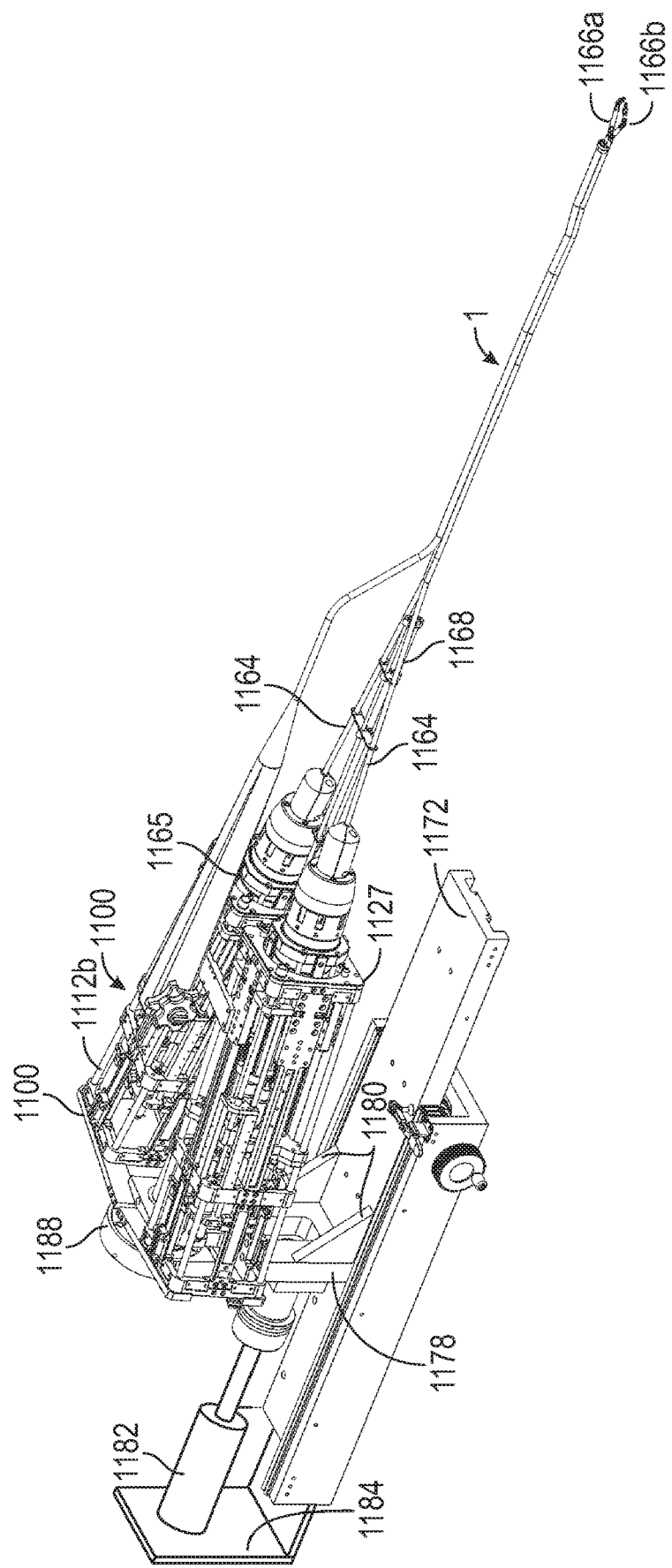
FIG. 60 is an isometric view of the portion of the positioning and control device of FIG. 54, whereby a portion thereof has been moved to a forward position.
Figure 61:
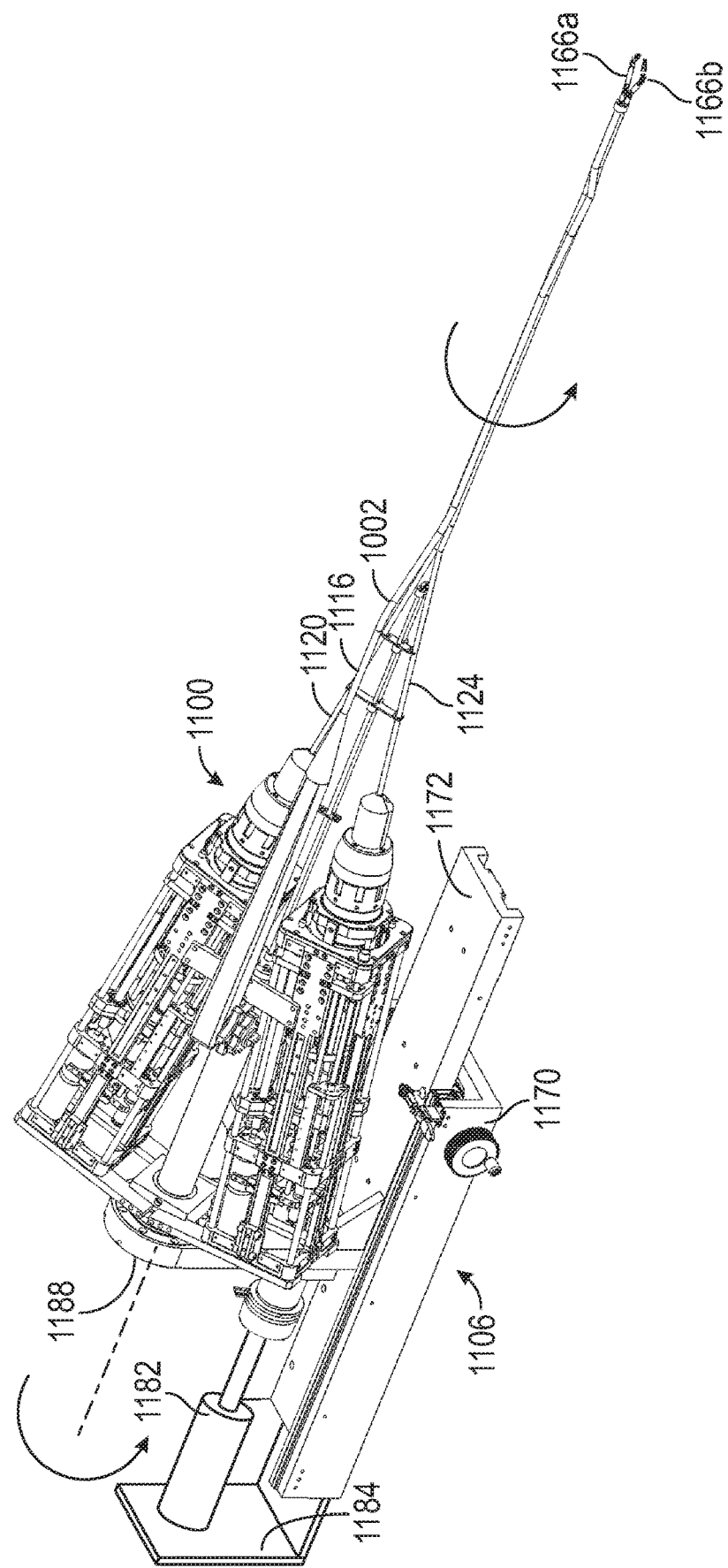
FIG. 61 is an isometric view of the portion of the positioning and control device of FIG. 54, whereby a portion thereof has been moved to a forward position and rotated.

FIGS. 54, 60 and 61 further illustrates the additional alternative construct of the surgical tool used in the procedure of FIG. 53. Herein, the driving part 40 includes a mechanical carriage 1100 which is mounted to a horizontal surface 1104, such as the top of a table or a cart which can be locked in position adjacent to a patient in an operating theater. As shown in FIG. 54, the mechanical carriage 1100 in this configuration includes a lower horizontal movement mechanism 1106, a rotation mechanism 1108 connected thereto, a rotatable housing 1110 connected thereto, and cages, in the embodiment, two cages 1112a, b within each of which are mounted a robotic controller 1114a, 1114b. A first tubular member 1116, herein the insertion tube 1002 of a standard endoscope, is also provided. The proximal end 1118 of a second tubular member 1120 comprising a first tubular flexible member 200 (see FIG. 55) of the prior embodiments hereof is connected to the first robotic controller 1114a, and the proximal end 1122 of a third tubular member 1124 comprising a second tubular flexible member 200 of the prior embodiments hereof is connected to the second robotic controller 1114b. Each of the tubular members 1120, 1124, further include an extending portion 1126, 1128 extending from the driving part 40 and terminating in a distal end 1130, 1132.

Figure 56:
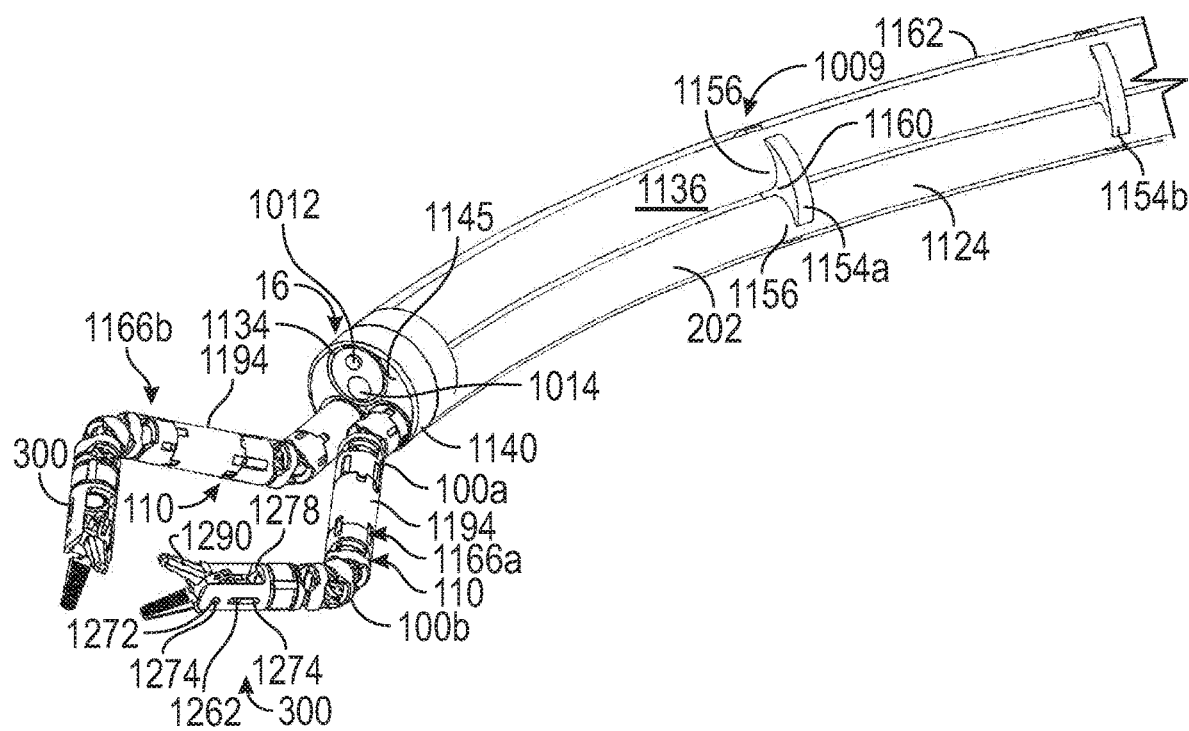
FIG. 56 is an isometric view of a portion of a robotic arm of the surgical device hereof.

As shown in FIGS. 56 to 58, the first tubular member 1116 includes a generally extending portion 1136 also terminating at a distal end 1134, distal to the manipulator housing 1138 thereof (FIG. 54). The distal end of the insertion tube 1002 includes a camera 1012, a working channel 1014 for slidingly providing tool access and control, an illuminating device (not shown) such as an LED or light bundles, as well as irrigation and suction ports (not shown). The distal ends 1130, 1132 and 1134 are secured within the distal coupler 1140. Distal coupler 1140 includes an outer circumferential wall 1142 terminating at one end thereof with a reduced diameter outer wall 1143, and a plurality, in the embodiment described, three openings 1146, 1148 and 1150 extending therethrough (see FIGS. 57 and 58). One end of a surrounding sheath 202 extends inwardly of each of openings 1148, 1150. The first opening 1146 receives the distal end 1134 of the first tubular member so that the camera 1012, working channel 1014, illuminating device and irrigation and suction ports (not shown) thereof are exposed to the exterior of the distal coupler 1140, and each of the second and third openings 1148, 1150 receive the distal ends of the surrounding sheaths 202 and the distal ends 1130, 1132 of the second and third tubular members 1120, 1124 therein, such that the distal ends 1130, 1132 of the second and third tubular members 1120, 1124 can be extended and retracted with respect to the end face 1145 thereof. The end of outer sheath 1162 is extended over the reduced diameter outer wall 1143 of the distal coupler 1140 and thereby secured thereto. As best shown in FIG. 60, the proximal ends 1164 of the surrounding sheaths 202 are held in a bridge structure 1168 which extends generally parallel to the sliding plate 1172 (see FIG. 61) and thereabove, and extends outwardly with respect thereto, and is secured, at a first end 1165 thereof, to a cross piece (not shown) extending between cages 1112a, b. With this construct, the distal ends of the surrounding sheaths 202 located within the distal coupler 1140 maintain a fixed length from the cages 1112a, b.

To prevent binding and undesired bowing of the extending portions 1126, 1128, 1136, one or more coupling members 1154a, b are provided along their length to receive the surrounding portions 202 through which extending portions 1126, 1128, 1136 extend therein. In this embodiment, as shown in FIG. 59, each coupling member 1154a, 1154b is a generally circular plate like member, having a number of openings equal to the number of tubular members, in this embodiment three openings 1156, spaced apart from one another by approximately 120 degrees about the center of the coupling members 1154a, b. Each of the extending portions 1126, 1128, 1136 extend through one of the openings. Extending portion 1136 of first tubular member 1116 extends through the openings 1156a in each coupling member 1154a, 1154b. The outer diameter of the first tubular member 1116 and the inner diameter of the openings 1154a are sized such that the first tubular member 1116 may be pulled or pushed through the openings 1154a, but the first tubular member 1116 will not move with respect to the coupling members 1154a, b unless a high degree of force, greater than that experienced during use of the surgical apparatus 1, is applied therebetween. In contrast, the outer circumference of the surrounding sheaths 202 surrounding the extending portions 1126, 1128 is smaller than the inner circumference of the openings 1156b, c, and thus the surrounding sheaths 202 and the extending portions 1126, 1128 therein are able to move freely forwardly and reversely through the openings 1156b, c. However, each of the surrounding sheaths 202 and extending portions 1126, 1128, 1136 are constrained against significant movement radially inwardly or outwardly from the center 1160 of the coupling members 1156a, b. The outer sheath 1162, along with the extending portions 1126, 1128, 1136, form the introduction portion 1004 of the device.

A robotic surgical arm 1166 is provided at each of the distal ends 1130, 1132 of the extending portions 1126, 1128 of the tubular members 1120, 1124. As will be described further herein, the robotic surgical arms 1166a, each comprising a first steerable member 100a and a second steerable member 100b, are interconnected by a connector 1144, wherein each steerable member includes include a plurality of bending segments 110 pivotally connected to one another, configured as one or more of the linkages described herein with respect to FIGS. 3 to 29, which are controllably positionable under the control of elements of the mechanical carriage 1100 to be extended and retracted with respect to the distal coupler 1140 such that they may be fully retracted inwardly of the coupling members distal coupler 1140 and the outer sheath 1162, or extended therefrom as shown in FIG. 56.

Referring now to FIGS. 54, 60 and 61 the operation of the mechanical carriage 1100, and the corresponding motions of the tubular members 1116, 1120 and 1124 and the robotic surgical arms 1166a, b are described with respect thereto. Referring initially to FIG. 54, the lower horizontal movement mechanism 1106 of mechanical carriage 1100 includes a base 1170, a sliding plate 1172 moveably secured therein by opposed roller supported sliding guides 1174, and lower rolling supports 1176. At one end of the sliding plate 1172 distal from the location of the second and third tubular members 1120, 1124 extends an upright 1178 supported at the opposite sides thereof by gussets 1180. The lower end of upright 1178 is secured to the sliding plate 1172 by fasteners or by being welded thereto, and the gussets 1180 are likewise welded to the upper surface of the sliding plate 1172 and a side surface of upright 1178.

An actuator 1182, such as a pneumatic linear drive or a lead screw based drive, is secured at one end thereof to the back side of the upright 1178, and an opposite end thereof is mechanically grounded, such as by a connection 1184 to the same surface as the base plate 1170 rests on, or by a rigid connection to the base plate 1170 as shown. Actuation of the linear actuator 1182 causes linear movement of the sliding plate 1172, such as from the position thereof in FIG. 54 to the position thereof in FIG. 60. The linear actuator can be a linear motor, a stepper motor and lead screw mechanism, or other device capable of reliable causing 1 mm or less movement between the sliding plate 1172 and the base plate 1170.

The rotatable housing 1110 is connected, through a shaft (not shown) extending from the rear facing portion thereof, into a bearing 1186 supported in the upright 1178. A rotational actuator 1188, in the embodiment a stepper motor capable of arcuate movement of the rotatable housing about its axis by less than one degree, is connected to the rear side of the upright 1178, and the shaft thereof (not shown) is coupled to the shaft of the rotatable housing. Operation of the rotational actuator causes rotational movement of the of the rotatable housing 1110 about the center line of the shaft thereof, such as from the orientation thereof shown in FIG. 54 to the orientation thereof shown in FIG. 61.

Figure 62:
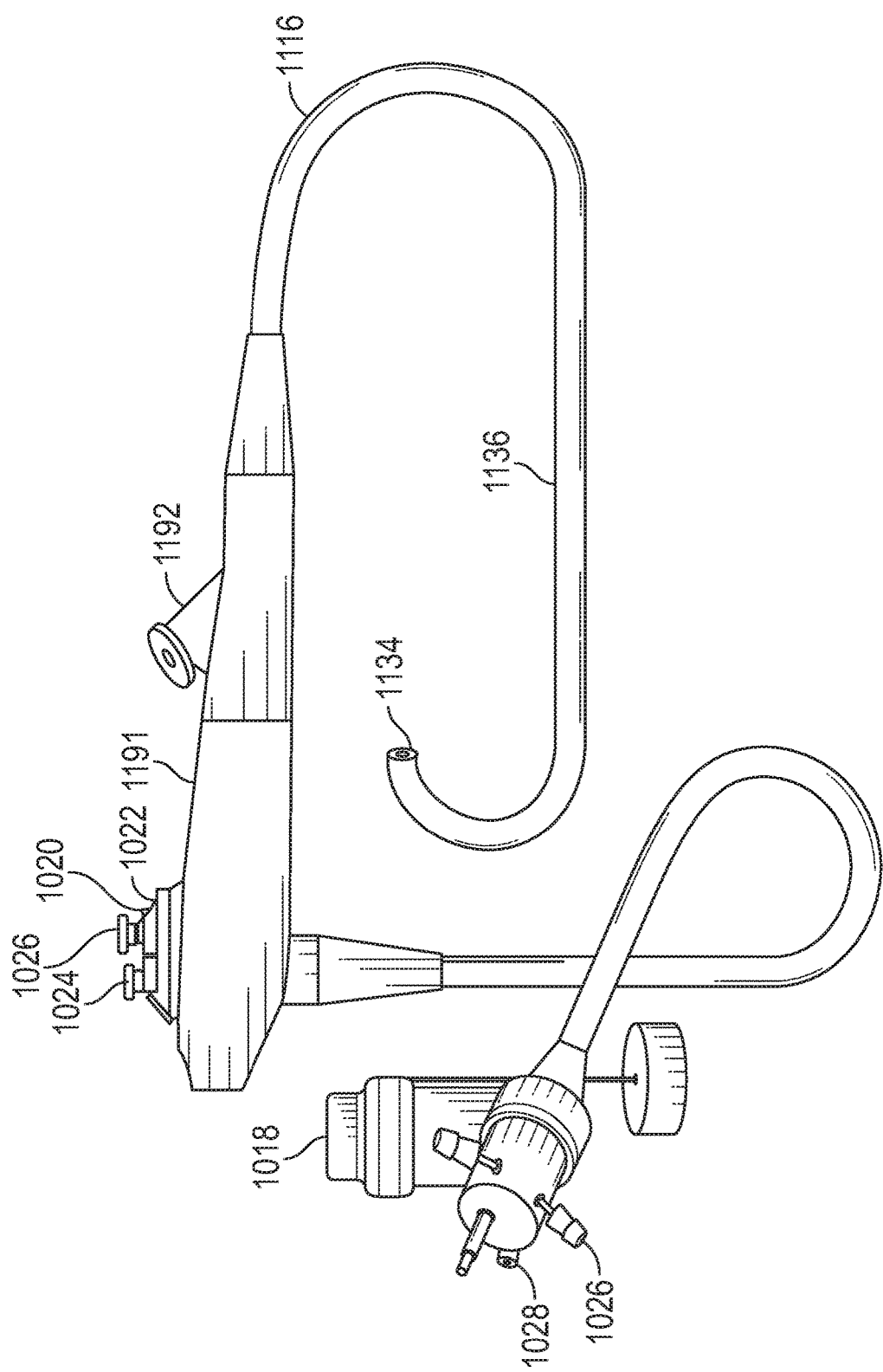
FIG. 62 is a schematic view of an endoscope.

As previously described, the first tubular member 1116 is the insertion tube 1002 of a standard endoscope, which as shown in FIG. 62 includes a handle 1191, and one more introduction ports 1192 in the handle and communicable with a hollow interior portion of the tubular member 1116. As shown in FIG. 56, at the distal end 1134 of the extending portion 1136 of the first tubular member 1116 are provided a camera 1012, such as a pixel array and a working channel 1014. Wires, not shown, extend from the camera 1012 along the tubular member 1116 back to the handle 1191 and thence to a video port 1018, and thence to a display screen. As shown in FIG. 62, the end of the first tubular member 1116 is curved or curled. The standard endoscope is capable of bending under control of an operator such as a doctor or surgeon, wherein the first tubular member 1116 is configurable in a generally straight line or a portion thereof adjacent to the distal end 1134 thereof is bent as shown in FIG. 59. The handle 1191 of the endoscope includes a deflection control knob 1020 which the operator moves to selectively and controllably bend the endoscope at the distal end, and which is selectively lockable by actuation of a deflection lock toggle 1022. Additionally, a suction port 1026 extends from the handle 1191 to the distal end 1134 of the first tubular member 1116 and is connectable to a suction line, and the suction port 1026 is selectively variable between an open and closed position by operation of a suction valve 1024 on the handle 1190. Also, liquids or gasses can be introduced through port 1028 which also extends to the distal end 1134 of the first tubular member 1116. During introduction of the introduction portion 1004 of the device, the surgeon or other operator can use the controllable bending capability of the distal end 1134 of the first tubular member 1116 to orient the distal end of the introduction portion 1004 to also bend to face a location of interest in a body lumen, by moving the distal end 1134 using the deflection control knob 1020 while viewing a video display (not shown) coupled to the camera 1012 of the endoscope on which the image captured by the camera 1012 is displayed.

Once the distal end of the introduction portion 1004 is positioned adjacent a location of interest in the body lumen, in this case a lesion 1250 on the esophageal wall 1252 as shown in FIG. 53, controlled linear movement of the sliding plate 1172, and arcuate motion of the rotatable housing 1110, enable controlled linear and rotational movement of the introduction portion 1004 formed of the outer surrounding sheath 1162, the distal coupling 1040 and the first, second and third tubular members 1116, 1120 and 1124, to allow an operator, such as a surgeon or doctor, to further position the distal ends 1134, 1130 and 1132 of the first, second and third tubular members 1116, 1120, 1124 at a desired location within a body lumen of a patient. As the distal end of the introduction portion 1004 is moving within the body lumen to a desired location therein, or is being retracted from the body lumen, the robotic surgical arms 1166a, 1166b shown in an extended position in FIG. 56 are disposed in a retracted position, wherein they are retracted inwardly of the openings therefor 1148, 1150 in the coupler 1140. Initially, by linear and rotational movement of the carriage 1100, the distal end of the introduction portion 1004 is located adjacent to, and oriented as desired with respect to, the lesion 1250. Once in this location, the introduction portion 1004 is clamped exteriorly of the patient to prevent movement of the distal end 1134 thereof, such as by locking the rotational housing 1110 and sliding plate 1172 against further movement.

To use the surgical device to remove the lesion and suture shut the incision using the robotic surgical arms 1166a, 1166b, each of the robotic controllers 1114a, b in the mechanical carriage 1100 are configured to cause independent rotating and linear movement of the second and third tubular members 1120, 1124 with respect to the mechanical carriage 1100, to thereby enable linear movement of the first and second tubular members 1120, 1124 to extend and retract the robotic surgical arms 1166a, 1166b with respect to the coupler 1140, and to rotate the robotic surgical arms 1166a, 1166b about the axis of the first and second tubular members 1120, 1124. Additionally, to bend the steerable members 100a, 100b at the end of each tubular member 1120, 1124, each of the robotic controllers 1114a, b also includes a plurality, herein ten, fine positioning members 1190. Four of the fine positioning members 1190 are connected to wires 400 connected to the steerable member 100a, four are connected to four individual wires 400 connected to steerable member 100b, and two are connected to a wire passing over a pulley in the end effector 300. All ten extend through the respective second or third tubular member 1120, 1124.

Figure 63:
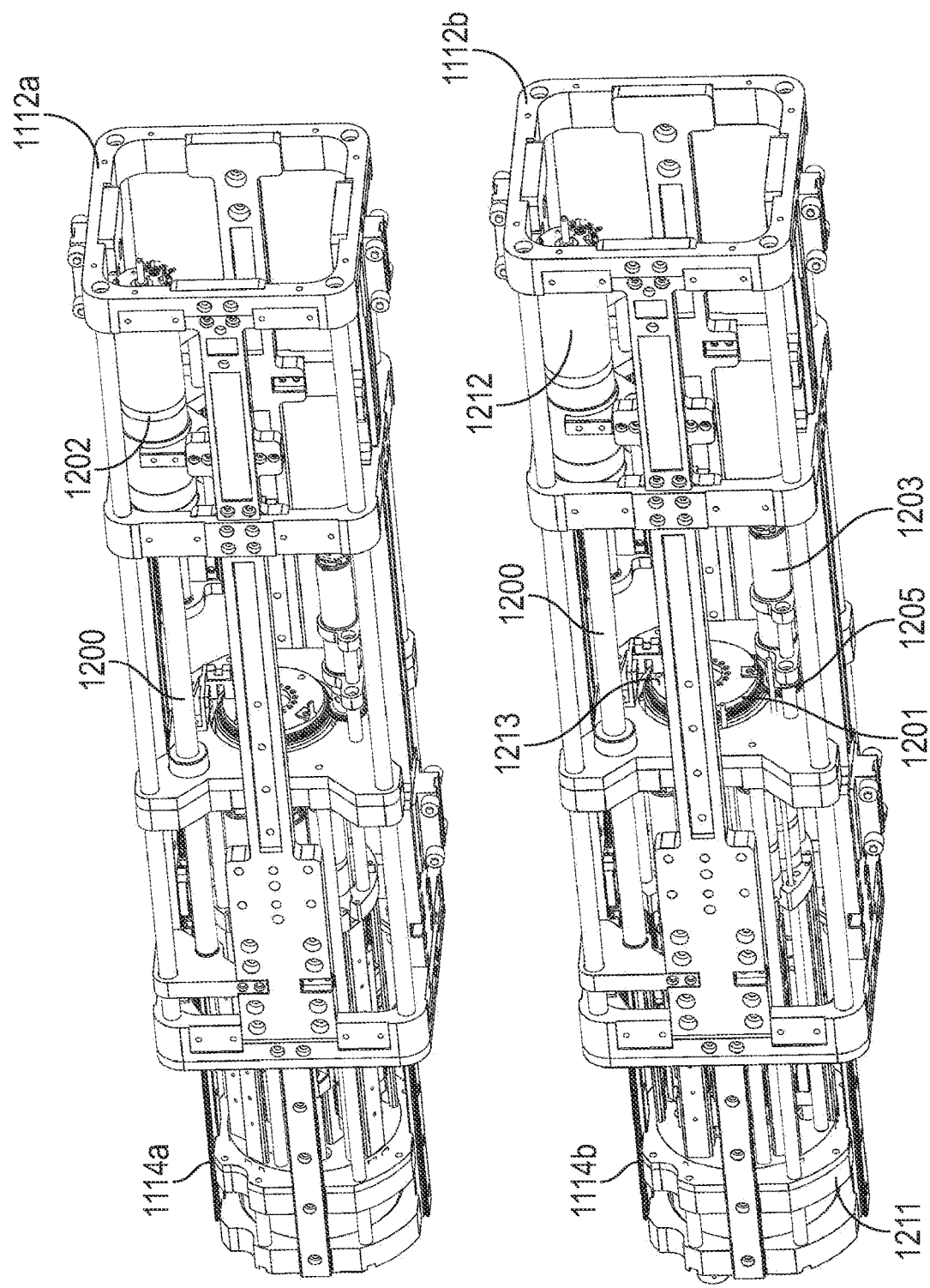
FIG. 63 is an isometric view of the robotic controllers of the surgical device hereof.

Referring to FIG. 63, first robotic controller 1114a is supported within cage 1112a, and second robotic controller 1114b is supported within cage 1112b, and each of the cages is fixedly secured within the carriage 1100. In addition to being movable linearly by the movement of the slide plate 1172 moving the carriage 1100, each robotic controller 1114a, b is also linearly moveable with respect to cage 1112a, b, to thereby allow independent linear displacement of the second and third tubular members 1120, 1124, and thus the distal ends thereof. To provide this functionality, a shaft 1200 extends from a positioning device 1202 coupled to the each of the cages 1112a, b to the respective robotic controller 1114a, b, and the shaft 1120 is extendable and retractable with respect to the positioning device 1202 to extend or retract the robotic controllers 1114a,b inwardly or outwardly of the cages 1112a, b. The positioning device is, for example, a linear motor, a stepper motor coupled to the shaft 1120 through a lead screw, or other linear positioning device capable of linear movement in steps of 1 mm or less. Because the distal ends of the surrounding sheath 202 in the distal coupler 1140 extend a fixed distance from the bridge structure 1168 (see FIG. 60), and the bridge structure 1168 position is fixed with respect to the cages 1112a, b, rotational and linear movements of the robotic controllers 1114a,b with respect to the cages 1112a, b results in rotational and linear movement of the second and third tubular members 1120, 1124 with respect to the cages, and thus with respect to the surrounding sheaths 202. As a result of this construct, the position of the distal coupler 1140 can be held in a substantially fixed location with respect to the base 1170 once the introduction portion 1104 has been introduced so that the distal coupler 1140 is at the desired location in the body lumen by locking the rotation and linear movement of the carriage 1100, and thus when the robotic controllers 1114a, b are moved linearly or rotationally with respect to their respective cages 1112a, b, the second and third tubular members 1120, 1124 affixed to their ends likewise move linearly or rotationally with respect to the cages 1112a, b and thus also linearly and rotationally with respect to the distal coupler 1140 connected to the surrounding sheaths 202, to allow extension, retraction, and rotation of the end effectors operatively connected to the distal ends of the tubular members 1120, 1124 with respect to the distal coupler 1140.

To enable rotational movement of each of the tubular members 1120, 1124 around their longitudinal axis, each robotic controller 1114a, b is configured as an outer housing 1211 and an inner, rotatable member 1213 having at the rear side thereof comprising a driven ring gear 1201 and the front side terminating at the end face 1208 thereof. The outer housing 1211 is linearly moveable within the cage 1112a, b by the positioning device 1202. To cause rotation of the inner rotatable member 1213 with respect to the outer housing 1211, and thereby rotate the tubular members 1120, 1124 connected thereto, a rotary drive comprising a stepper motor 1203 connected to a driven gear 1205 is provided, the stepper motor 1203 is connected to the rear side of the outer housing 1211, and thus, as the outer housing is moved linearly within the cage 1112a, b, the driven gear stays in position relative to the ring gear 1213. The teeth of the driven gear mesh with those of the ring gear 1201, to rotate the inner rotatable member 1213. Thus, rotation, extension, and retraction of the tubular members 1120, 1124 with respect to the introduction portion is provided, to enable the operator of the device to extend, retract, and rotate the steerable members 100 with respect to the distal end of the introduction portion 1004.

Figure 64:
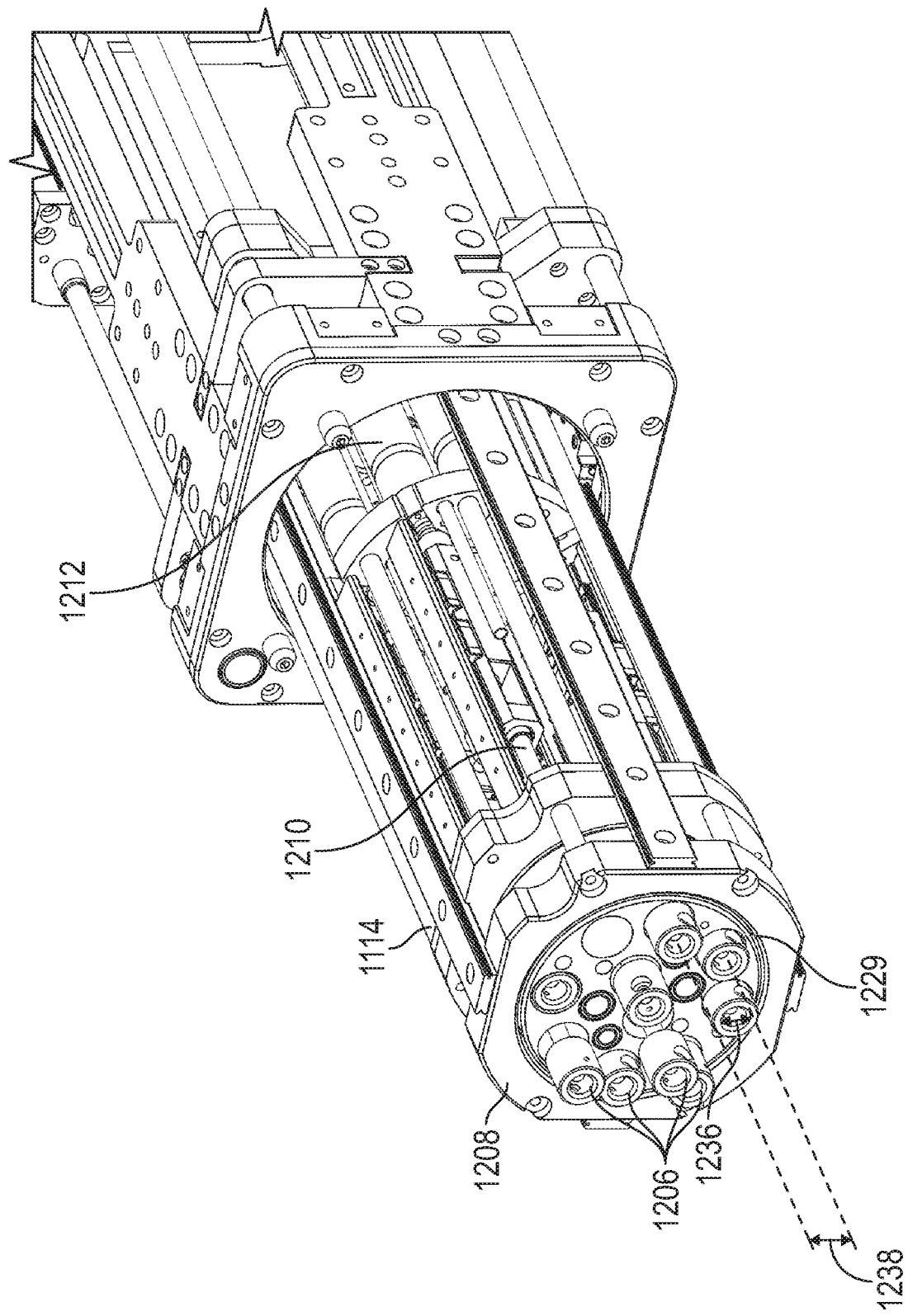
FIG. 64 is an isometric view of one of the robotic controllers of FIG. 63, showing the actuators for wires.
Figure 65:
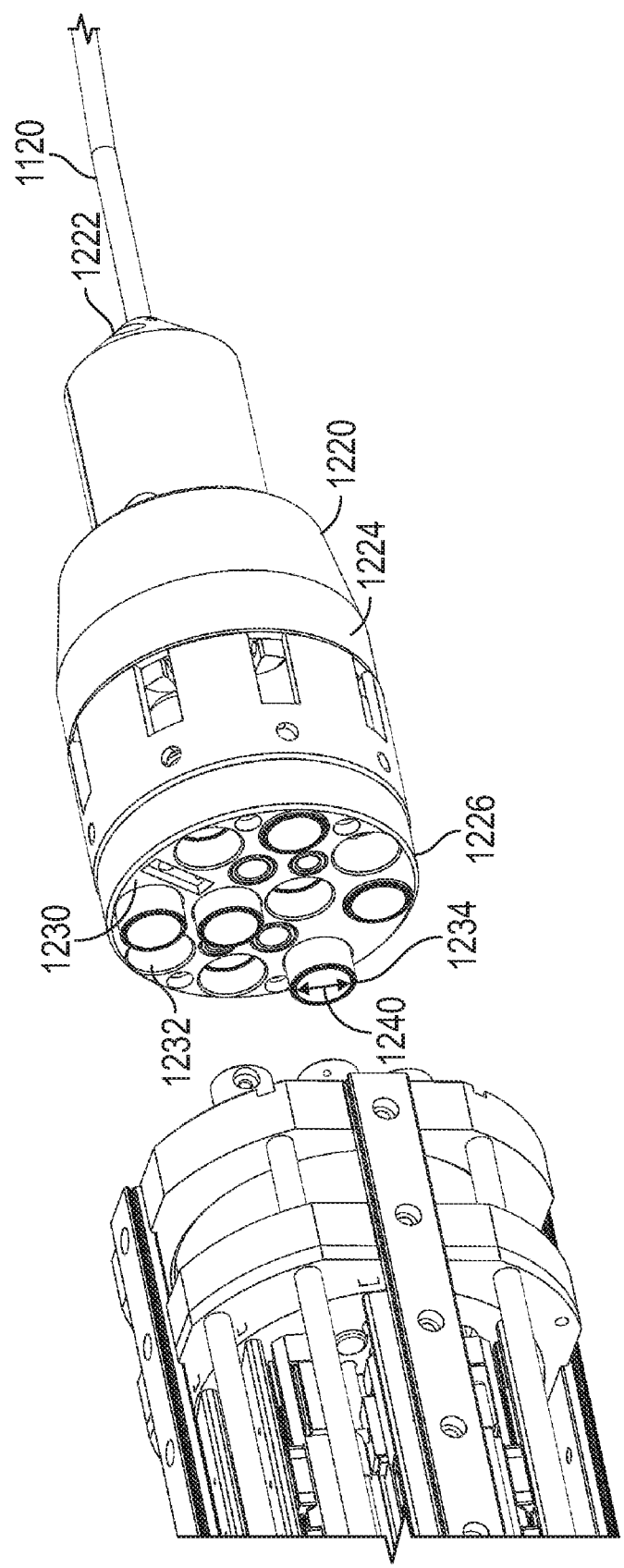
FIG. 65 is an isometric view of the end of a wire coupler of the surgical apparatus hereof.

To enable bending of the steerable members, the positioning of the wires 400 used to control the relative position and orientation of the bending segments must be controlled. Referring now to FIGS. 64 and 65, the mechanism for controllable movement of the wires 400, 500 used to control the movement and orientation of the steerable member 100, and actuation of the end effectors 300, are shown. In the embodiment of the surgical device shown in FIG. 54, each of the sets of bending segments 110 in each steerable member 100a, 100b are configured such as thus shown and described with respect to FIGS. 13a-13c, incorporating the off-axis hinge 814 construct as shown and described with respect to FIGS. 36 and 37. As a result each adjacent link on a plurality of contacting bending segments 110 of each steerable member 100 can swing about an axis perpendicular to the swing axis of an adjacent link. To enable this controllable movement of each of the steerable members, each steerable member 100a, b at the end of a tubular member 1120, 1124 is connected, at the distal most bending segment thereof from the robotic controller 114a, b, to four guide wires 400, the tension, and the relative position of each with respect to the robotic controller 1114, is controlled thereby. For positioning the four wires 400a-d connected to each steerable member 100a, 100b, each robotic controller 1114 includes, in this embodiment, eight drive rods 1206 selectively extendable from the tubular member facing surface 1208 thereof, where each drive rod 1206 is connected to a lead screw mechanism (not shown) within the robotic controller 1114 which in turn is connected to a lead screw 1210 and a stepper motor 1212. A lead screw mechanism, lead screw 1210 and stepper motor 1212 are dedicated to each drive rod 1206. To extend or retract a drive rod 1206, the stepper motor 1212 dedicated thereto is rotated to rotate the lead screw 1210 connected thereto. The threads on the lead screw 1200 extend through a threaded opening in the lead screw mechanism, which is free to move linearly with respect to the longitudinal axis of the lead screw 1210 but is fixed against rotation, and thus rotation of the lead screw 1210 causes linear motion of the lead screw mechanism, and thus of the drive rod 1206 connected thereto. Rotation of the stepper motor 1212 in a first direction causes the drive rod 1206 to extend from the end face 1208 of the robotic controller 1114, and reverse rotation in a second direction causes the drive rods to retract toward the end face 1208 of the robotic controller 1114.

The tubular members 1120, 1124 are detachable from their dedicated robotic controllers 1114, to allow different tubular members 1120, 1124 having different end effectors thereon to be configured into the surgical device. To enable this construct, each tubular member 1120, 1124 terminates at the proximal end thereof in an instrument connector 1220. Instrument connector 1220 includes a housing 1222 into one end of which extends the proximal end of the tubular member 1120, 1124, an outer shell 1224, and an extending circumferential lip 1226. To connect the instrument connector 1220 to the robotic controller 1114, the robotic controller 1114 includes a circular recess 1228 extending inwardly of the face 1208 thereof, into which lip 1226 is inserted. Instrument connector 1220 also includes a connecter face 1230 surrounded by lip 1226, into which extend terminal recesses 1232 into which individual wire terminals 1234 are selectively positionable or extendable. One of each of wires 400, 500 are terminated within one of each of the wire terminals 1234, and thus, movement of the wire terminals inwardly or outwardly, or toward or away from, connector face 1230, results in corresponding tension or slack in a wire 400, 500.

Each drive rod 1206 of the robotic controller 1114 is connected to one of the wire terminals 1234, to move the wire terminal to which it is connected inwardly or outwardly, or toward or away from, the connector face 1230. In the embodiment, each drive rod 1206 terminates outwardly of the robotic controller 1114 in a magnetic hollow cup 1236, the outer diameter 1238 of which is dimensioned to fit within inner diameter 1240 of a corresponding wire terminal 1234 and maintain the connection therebetween magnetically. Alternatively, a spring loaded ball can partially extend from the outer wall of the cups to engage a detent on the inner wall of the wire terminal, or a bayonet connection, or other connection which is sufficiently tight to ensure the connection does not disconnect in use, but allows an instrument connector 1220 to be readily removed and replaced, is provided.

Within each of the tubular members 1220, 1224, the plurality of wires 400, 500 extend through sleeves 600 (see e.g. FIGS. 26 to 29) which guide the movement of the wires and prevent them from bowing or otherwise introducing slack in the wire system.

The use of the surgical tool hereof is described with respect to a use to evaluate a patients' esophagus. Initially, as shown in FIG. 53, a patient is intubated and an introduction tube 1008 is extended into the throat and down the esophagus such that the end thereof extends past the esophageal-tracheal junction. Then the introduction portion 1004 of the surgical device is grasped by the surgeon or other operator, and guided into the patients mouth and through the introduction tube 1008 until the distal end thereof is positioned at a desired location in the patients' esophagus, for example a location of interest previously identified, or identified and biopsied, using a standard endoscope. At this point, the relative position of the sheath to the patient is loosely locked in position. The introduction of the surgical apparatus 1 into the patient is guided by the surgeon or other operator viewing the esophagus through the projected image on the screen captured by the CCD or CMOS camera in the endoscope. During the introduction of the introduction portion 1004, the drive rods 1206 are actuated forward, i.e., they push both ends of the wires 400 and the wires 500 in the direction of the distal end of the introduction portion 1004, to release any tension in the wires 400, 500 and thereby allow the introduction portion 1004 to bend as it is introduced into the patient. Once the desired location and orientation of the distal coupler 1140 is fixed in the patient, the drive rods 1206 are retracted to their initial wire tensioning position wherein the steerable members 100 are positioned within the introduction portion, and the surgeon, using a controller, controls the position of the end effectors 300 on the tubular members 1120, 1124 by causing linear movement of the sliding plate 172 and rotation of the cage 1112a, 1112b to finely position the end effectors in a desired location, and tensioning of the wires to bend the bendable segments 110 by instructions of the controller to the stepper motors 1212 as a result of steering of the end effectors by the surgeon using the personalized master controller as described in FIGS. 45 to 52, haptic joystick or other control device at the surgeon station, such that tension on the wires 400 is either increased or decreased, as appropriate, to bend the steerable member 100 and thereby accurately position the tips or sides of the end effectors. Additionally, rotational motion of a controller associated with one of the steerable members 100 at the surgeon station results in rotation of the tubular member 1120 or 1124 by the robotic controller 1114a or 1114b on which the steerable member 100 associated with the controller is positioned, and thereby position the tip of the end effector anywhere along an hemisphere in front of the steerable member 100 and end effector.

Figure 66:
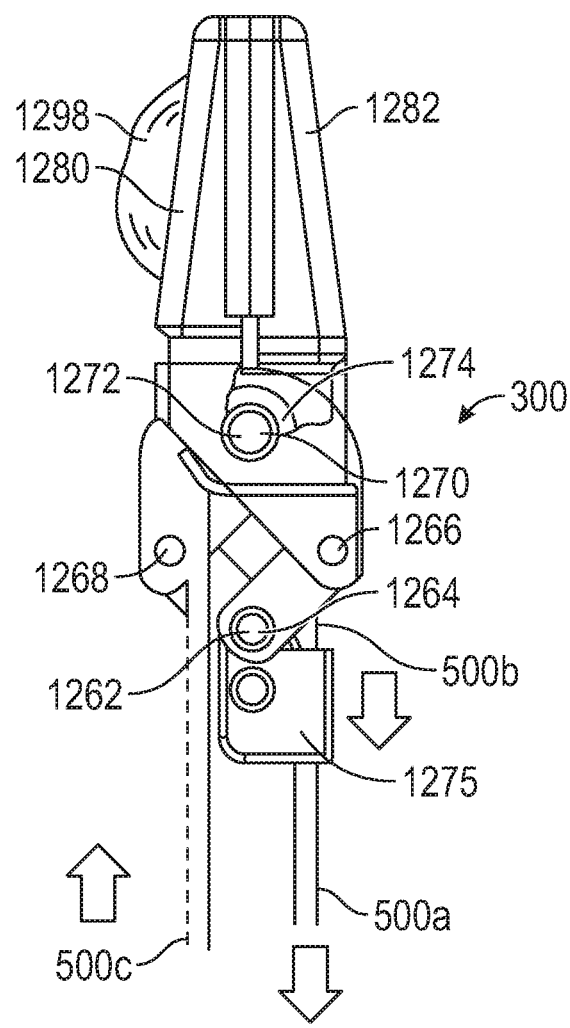
FIG. 66 is a plan view of an end effector of the surgical device hereof.

Referring now to FIG. 66, the connection of the wires 500 to the end effectors is shown.

Referring now to FIG. 66, the connection of the wires 500 to the end effectors is shown. Here, in contrast to the wires 400 used to articulate the steerable members 100, the opening and closing of each end effector 300 is performed by actuation of a single wire forming a first portion 500A and as second portion 500B, which is extended around a pulley 1260. The end effector 300 is a four bar linkage, having a first pivot point 1264, a second pivot point 1266, a third pivot point 1268 and a fourth pivot point 1270. As shown in FIG. 56, the pivot point 1264 includes a sliding pin 1262 extending therefrom into a slot (not shown) in the opposed side walls of the end effector housing, and pivot point 1270 includes a pin 1272 extending therefrom into a mating opening (not shown) in the opposed side walls of the end effector housing 1274. The wire extends from the proximal portion of each tubular member 1116, 1120 as a first portion 500a, loops over pulley 1274 located around pin 1272, and extends therefrom as a second portion 500b back through the tubular portions 1116, 1120 and a clamp 1275 connected to pin 1262 is clamped over the second portion.

To open and close each end effector 300, each robotic controller 1114 includes, in this embodiment, a single wire drive rod coupled to one end of wire 500, and the other end of wire 500 is fixed in position with respect to the robotic end effector. The wire 500 loops over the pulley 1260. Thus, when the moveable end of the wire is retracted toward the robotic controller 1114, the effective length of the two wire segments to either side thereof are shortened by one-half the retraction distance, the biasing member 1276 is compressed, and the jaws move together. When the moveable end of wire 500 is extended from the robotic controller, the reverse occurs, and spring member biases the jaws 1280, 1282 to pivot about the fourth pivot point 1272 in an opening direction. Thus, the operator, such as a surgeon, by use of the controller, can position the end effector such as forceps adjacent to a location of interest, and manipulate the forceps to perform a surgical procedure. Referring to FIG. 56 one of the end effectors includes a cutting blade 1290 extending from a side wall thereof. The cutting blade 1290 may be used to cut away tissue and remove the lesion 1250 of FIG. 53. Then, the surgeon can manipulate suturing needles (not shown) to suture closes the cut.

Because two steerable members 100a, b are located on each tubular member 1120, 1124, and the distal end of each steerable member can be located on an imaginary partially spherical surface defined by the arcuate movement of the bending segments 110, a high degree of operation freedom of motion and freedom of positioning is provided by the surgical device hereof.

The operation of the end effector and steerable arm, as well as the rotational and linear motion of the mechanical carriage 1100 to position the distal end of the introduction portion 1004 of the surgical apparatus 1 adjacent to a location of interest in a body lumen, followed by controlled movement of the end effectors, is controlled by a control system.

As seen above, several exemplary embodiments of a surgical apparatus have been described. However, these exemplary embodiments are for illustrative purposes only. For example, the above-described surgical instruments may be configured as individual surgical apparatuses, or they may be applied to a variety of medical devices, such as a lumen unit or imaging unit with a working channel, as well as to a surgical apparatus with an end effector. Furthermore, various embodiments of a steerable member may be integrated or otherwise adapted for a variety of surgical apparatuses, including, but not limited to, catheters, endoscopes, and surgical robots that are bendable at the distal end thereof.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, product, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, a term preceded by "a" or "an" (and "the" when antecedent basis is "a" or "an") includes both singular and plural of such term, unless clearly indicated otherwise (i.e., that the reference "a" or "an" clearly indicates only the singular or only the plural). Also, as used in the description herein, the meaning of "in" includes "in" and "on" unless the context clearly dictates otherwise.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted. The scope of the disclosure should be determined by the following claims and their legal equivalents.

In some embodiments is a surgical apparatus comprising: a surgical apparatus comprising: a steerable member that is bendable and comprises a plurality of bending segments with channels therein; and a plurality of bending actuation wires that are arranged to pass through the steerable member and cause the steerable member to bend, the steerable member comprising at least one lumen through which the bending actuation wires pass, and the lumen being partially open outward. In some embodiments, the bending segments are hinged to adjacent bending segments. In other embodiments, the connecting parts of each bending segment are pinned to an adjacent bending segment. In other embodiments, the connecting parts of each bending segment are accommodated in recess parts of the adjacent bending segment and hinged thereto. In other embodiments, each connecting part comprises a protrusion with a round surface, and each recess part is shaped to accommodate each connecting part such that each connecting part may rotate. In other embodiments, each connecting part comprises a protrusion with a linear edge, and each recess part is shaped like a v-shaped notch such that each connecting part may rotate while in linear contact with each recess part. In alternative embodiments, a pair of connecting parts are provided facing each other on one side of the length of each bending segment, a pair of recess parts are provided facing each other on the other side of the length of each bending segment, and the pair of connecting parts and the pair of recess parts are arranged in a direction perpendicular to each other so as to permit bending in at 2 degrees of freedom. In other embodiments, four lumens are formed along the length of each bending segment, and each lumen passes through at least a portion of a connecting part or a recess part. In some aspects, each lumen comprises a closed lumen portion and an open lumen portion, and a portion of each lumen passing through the connecting part or the recess part forms a closed lumen portion and the other side of the connecting part or the recess part forms an open lumen portion. In other embodiments, each bending segment has four lumens along the length, and each lumen is located between the locations of the connecting part and recess part along the circumference. In other embodiments, each lumen comprises a closed lumen portion and an open lumen portion, wherein the closed lumen portion is formed at the middle of the lumen length and the open lumen portion is formed on both sides of the closed lumen portion. In some embodiments, the steerable member comprises a plurality of plate-like bending segments and connecting parts of flexible material located between the bending segments. In other embodiments, the connecting parts are formed integrally between the bending segments and extend from two edge of the channels provided at the center of the bending segments to an outward direction, and the connecting parts are formed in a direction perpendicular to adjacent connecting parts. In other embodiments, the bending actuation wires are arranged to pass through the bending segments and the connecting parts, and each lumen with a bending actuation wire provided therein has a structure in which a portion located at a connecting part forms a closed lumen and a portion formed at a bending segment is open outward. In other embodiments, the connecting parts are configured to connect the centers of adjacent bending segments.

In some embodiments of the surgical apparatus further comprises an end effector provided at the distal end of the steerable member. In some embodiments, the end effector is connected to an effector actuation wire located in the channels of the steerable member such that it may be actuated by moving the effector actuation wire, and at least part of the end effector is detachably provided at the distal end of the effector actuation wire. In some embodiments, at least part of the end effector is magnetically connected to the distal end of the effector actuation wire. In other embodiments, the end effector comprises an effector module comprising: an instrument portion for performing a surgical operation; and an actuation portion connected to the effector actuation wire to actuate the instrument portion, wherein at least either the proximal end of the effector module or the distal end of the effector actuation wire comprises a magnetic body. In some embodiments, the surgical apparatus further comprises an effector actuation wire that is located in the channels of the steerable member and connected to the end effector to actuate the end effector, and the end effector further comprises an elastic body that is configured to produce an elastic force in the opposite direction to a force applied by the effector actuation wire. In other embodiments, the effector actuation wire is configured such that the end effector operates in a first mode when pulled by the effector actuation wire and operates in a second mode while not pulled by the effector actuation wire. In other embodiments, a forceps of the end effector is closed in the first mode and open in the second mode. In some embodiments, the end effector comprises: an instrument portion for performing a surgical operation; an actuation portion connected to the effector actuation wire to actuate the instrument portion; and a body portion forming a path along which the actuation portion reciprocates, wherein the elastic body is located at the proximal end of the actuation portion and applies an elastic force in a direction that pushes the actuation portion. In other embodiments, the actuation portion and the distal end of the effector actuation wire are configured to be attachable to or detachable from each other. In other embodiments, at least either the actuation portion or the distal end of the effector actuation wire comprises a magnetic body.

In some embodiments of the surgical apparatus, a wire termination member for fixing the distal ends of the bending actuation wires is provided at the distal end of the steerable member. In some embodiments, the wire termination member has a thread such that the bending actuation wires are fixed by screwing the wire termination member to the distal end of the steerable member. In other embodiments, the bending actuation wires are arranged to be fixed by being pushed while wound between the distal end of the steerable member and the wire termination member. In some embodiments, the wire termination member comprises at least one hole through which the distal ends of the bending actuation wires pass, and the wire termination member is provided at the distal end of the steerable member. In other embodiments, the holes in the wire termination member are formed at locations corresponding to the lumens in the steerable member. In other embodiments, the surgical apparatus further comprises an end effector provided at the distal end of the steerable member, the wire termination member being the end effector.

In some embodiments is a surgical apparatus comprising: a steerable member that is bendable and comprises a plurality of bending segments with channels therein; a plurality of bending actuation wires that are arranged to pass through the steerable member and cause the steerable member to bend, and the steerable member comprising at least one lumen through which the bending actuation wires pass; wherein the surgical apparatus further comprises: a flexible member comprising a flexible material that is provided at the proximal end of the steerable member; and at least one sleeve forming a path of travel of a wire passing through the steerable member or the flexible member, both ends of which are fixed to the inside thereof. In some embodiments, the wire comprises the bending actuation wires. In some embodiments, the body of the sleeve is longer than the longest possible path that is formed between two points at which both opposite ends of the sleeve are fixed when the steerable member or the flexible member is bent, in order to minimize the effect of the bending of the steerable member or flexible member on the movement of the wire in the sleeve. In some embodiments, the steerable member and the flexible member have a hollow space for the sleeve to be placed therein. In some embodiments, a second sleeve out of the at least one sleeve forms a path for the distal end bending actuation wire, one end of the second sleeve being fixed at the proximal end of the distal end steerable portion or the distal end of the proximal end steerable portion and the other end being fixed at the proximal end of the flexible member. In other embodiments, the second sleeve comprises an elastic material so that the distal end bending actuation wire is located along a curved path when the distal end steerable portion is bent. In some embodiments a third sleeve out of the at least one sleeve forms a path along for the proximal end bending actuation wire, one end of the third sleeve being fixed at the proximal end of the proximal end steerable portion or the distal end of the flexible member and the other end being fixed at the proximal end of the flexible member. In other embodiments, the third sleeve comprises an elastic material so that the proximal end bending actuation wire is located along a curved path when the proximal end steerable portion is bent.

In some embodiments is a surgical apparatus comprising: A surgical apparatus comprising: a steerable member that is bendable and comprises a plurality of bending segments with channels therein; a plurality of bending actuation wires that are arranged to pass through the steerable member and cause the steerable member to bend, and the steerable member comprising at least one lumen through which the bending actuation wires pass; a flexible member comprising a flexible material that is provided at the proximal end of the steerable member and forms a path along which the bending actuation wires pass; and a manipulating part that is provided at the proximal end of the flexible member for actuating the bending actuation wires, wherein the proximal ends of the bending actuation wires are attachable to or detachable from the manipulating part. In other embodiments, the proximal ends of the bending actuation wires and effector actuation wire are magnetically and detachably connected to the manipulating part.

In some embodiments is a surgical apparatus, wherein the bending actuation wires comprise a first bending actuation wire, and a second bending actuation wire that causes the steerable member to bend in the opposite direction to the first bending actuation wire, wherein screw members rotating in the same direction are provided at the proximal end of the first bending actuation wire and the proximal end of the second bending actuation wire and are configured to move in synch with each other in opposite directions. In some embodiments, the proximal end of the first bending actuation wire is configured to move along a first thread, and the proximal end of the second bending actuation wire is configured to move along a second thread oriented in the opposite direction to the first thread. In other embodiments, the first tread and the second thread are configured to rotate in the same direction by a single driving part. In other embodiments, the screw members are bi-directional lead screws, each having first and second thread portions formed on a single body. In other embodiments, the screw members comprise: a first lead screw with a first thread; and a second lead screw with a second thread, wherein the first lead screw and the second lead screw are configured to move in sync with each other by a gear and rotate simultaneously by a single driving part.

In some embodiments of the surgical apparatus, the steerable member has a geometric shape configured to bend more easily at the distal end than at the proximal end. In some embodiments, the bending segments have a geometric shape configured such that the steerable member bends more easily closer to its proximal end. In some embodiments, the bending segments have lumens formed at a distance from the center of a cross-section of the steerable member, and the closer to the proximal end of the steerable member, the more distant the lumens in the bending segments get from the center of the cross-section of the steerable member. In some embodiments, the steerable member further comprises a plurality of connecting parts located between the bending segments, wherein the connecting parts have a geometric shape configured such that the steerable member bends more easily closer to its proximal end. In other embodiments, the connecting parts are configured to have a smaller sectional width toward the proximal end of the steerable member so that the corresponding parts of the steerable member bend more easily. In other embodiments, the connecting parts are configured to increase in diameter along the length toward the proximal end of the steerable member so that the corresponding parts of the steerable member bend more easily.

In some embodiments is a surgical apparatus, comprising: a steerable member that is bendable; an end effector provided at the distal end of the steerable member; and an effector actuation wire that is arranged to pass through the steerable member and connect to the end effector to actuate the end effector, the end effector comprising an elastic body that produces an elastic force in the opposite direction to the force applied by the effector actuation wire. In some embodiments, the end effector is configured to operate in a first mode when pulled by the effector actuation wire and is configured to operate in a second mode by the elastic force of the elastic body while not pulled by the effector actuation wire. In other embodiments, the end effector is actuated in such a way that surgical elements at the distal end are closed in the first mode and open in the second mode. In other embodiments, the end effector further comprises an effector module comprising: an instrument portion for performing a surgical operation; an actuation portion connected to the effector actuation wire to actuate the instrument portion; and a body portion forming a path along which the actuation portion reciprocates. In other embodiments, the elastic body is located at the proximal end of the actuation portion for applying an elastic force to push the actuation portion in the direction of the distal end. In some embodiments, the effector module and the distal end of the effector actuation wire are configured to be attachable to or detachable from each other. In other embodiments, the effector module and the effector actuation wire are magnetically connected together.

In some embodiments is a surgical apparatus, comprising: a steerable member that is bendable; a plurality of bending actuation wires that are arranged to pass through the steerable member and cause the steerable member to bend; and a wire termination member provided at the distal end of the steerable member to fix the bending actuation wires, wherein the wire termination member has a thread for engaging with the distal end of the steerable member, such that the bending actuation wires are fixed by screwing the wire termination member and the steerable member together. In some embodiments, the bending actuation wires are configured to be fixed by winding between the distal end of the steerable member and the wire termination member. In other embodiments, the wire termination member comprises at least one hole through which the distal ends of the bending actuation wires pass, and the wire termination member is provided at the distal end of the steerable member. In other embodiments, the holes in the wire termination member are formed at locations corresponding to the lumens in the steerable member. In some embodiments, the end effector is provided on the wire termination member. In some embodiments, the surgical apparatus further comprises an end effector provided at the distal end of the steerable member, the wire termination member being the end effector.

In some embodiments is a surgical apparatus, comprising: a steerable member that is bendable; a first bending actuation wire that is arranged to pass through the steerable member to cause the steerable member to bend in a first direction; a second bending actuation wire that is arranged to pass through the steerable member to cause the steerable member to bend in a second direction which is opposite to the first direction; and at least one screw member to which the proximal end of the first bending actuation wire and the proximal end of the second bending actuation wire are coupled, such that the steerable member bends in the first or second direction by rotating the at least one screw member. In some embodiments, the at least one screw member is arranged to rotate about the longitudinal axes of the first and second bending actuation wires. In some embodiments, the proximal end of the first bending actuation wire and the proximal end of the second bending actuation wire are configured to move in sync with each other in opposite directions by rotation of the at least one screw member. In other embodiments, when the at least one screw member is configured to rotate in a first direction of rotation to move the proximal end of the first bending actuation wire backward and the proximal end of the second bending actuation wire forward, thereby causing the steerable member to bend in the first direction, and a second direction of rotation to move the proximal end of the first bending actuation wire forward and the proximal end of the second bending actuation wire backward, thereby causing the steerable member to bend in the second direction. In some embodiments, the proximal end of the first bending actuation wire is engaged with and moves along a first thread, and the proximal end of the second bending actuation wire is engaged with and moves along a second thread oriented in the opposite direction to the first thread. In other embodiments, the first thread and the second thread are configured to rotate in the same direction, such that the proximal end of the first bending actuation wire and the proximal end of the second bending actuation wire are configured to move in sync with each other in opposite directions. In some embodiments, the at least one screw member is a bi-directional lead screw having first and second thread portions formed on a single body.

In some embodiments is a surgical apparatus, comprising: a steerable member that is bendable; and a plurality of bending actuation wires that are arranged to pass through lumens in the steerable member and cause the steerable member to bend, wherein the steerable member has a geometric shape configured such that the steerable member bends more easily closer to its distal end. In some embodiments, the geometric shape is configured to provide a smaller radius of curvature closer to the proximate end of the steerable member.

In some embodiments is a surgical apparatus, comprising: a steerable member that is bendable and comprises a plurality of bending segments with channels therein; a plurality of bending actuation wires that are arranged to pass through the steerable member and cause the steerable member to bend; and a lateral supporting member that comprises an elastic material and exerts a restoration force for returning the steerable member to the initial position after bending. In some embodiments, the surgical apparatus further includes a plurality of lateral supporting members wherein the number of lateral supporting members is equal to the number of bending actuation wires. In some embodiments, the lateral supporting member is configured to bend in sync with the steerable member by the movement of the bending actuation wires, and the lateral supporting member has an elasticity configured such that it returns to its original shape when the force exerted on the bending actuation wires is released, thus bringing the steerable member back to the initial position. In some embodiments, the shape of the lateral supporting member before bending is linear. In some embodiments, the shape of the lateral supporting member before bending is bent to one side. In other embodiments, the lateral supporting members is configured in a tube shape, and a bending actuation wire is located inside the lateral supporting member.

In some embodiments is a surgical apparatus, comprising: a steerable member that is bendable and comprises a plurality of bending segments with channels therein and a plurality of connecting segments located between the bending segments; and a plurality of bending actuation wires that are arranged to pass through the steerable member and cause the steerable member to bend, wherein two ends of each connecting segment are hinged to different bending segments. In some embodiments, each connecting segment comprises: a pair of bodies that form portions hinged to the bending segment; and a guide member that joins together the pair of bodies and has a hollow space inside it where the bending actuation wires are located. In some embodiments, a bending segment connected to one end of each connecting segment is rotatable about a first hinge shaft, and a bending segment connected to the other end is rotatable about a second hinge shaft, and the first hinge shaft and the second hinge shaft are parallel to each other. In some embodiments, each connecting segment is arranged in a different direction from adjacent connecting segments to cause the connected bending segments to bend about different axes of rotation, in order to enable the steerable member to bend at least 2 degrees of freedom. In some embodiments, each bending segment comprises a plurality of lumens where the bending actuation wires are located, the lumens being arranged to not pass through the portions hinged to the connecting segment. In some embodiments, the bending segments are rotatable connected to the connecting segments, and the hinge shafts about which the bending segments rotate are in the same plane as the ends of the lumens where the bending actuation wires are located.

In some embodiments is a surgical apparatus, comprising: a steerable member that is bendable and comprises a plurality of bending segments, wherein each bending segment includes at least an intermediate joint having a first link portion and a second link portion and wherein the intermediate joint is arranged along a longitudinal axis direction of each bending segment; a plurality of bending actuation wires that are arranged to pass through the steerable member for causing the steerable member to bend; wherein the steerable member further comprises at least one lumen through which the bending actuation wires pass; and the intermediate joint further comprises a tension-regulating member which is coupled to the first link portion and the second link portion and is configured to regulate the tension of bending actuation wires by compensating the elongation of the bending actuation wires when bending segments bend, whereby the length of bending actuation wires is altered and kept in a predetermined tension. In other embodiments, the first interfacing half has a protrusion end, and the second interfacing half correspondingly has a recess end. In other embodiments, the first interfacing half has a recess end, and the second interfacing half correspondingly has a protrusion end. In some embodiments, the elongation of the bending actuation wires is compensated by being offset of two off-axis hinges. In some embodiments, the bending segment includes a series of interstacked intermediate joints.

In some embodiments is a surgical apparatus, comprising: a steerable member that is bendable and comprises a plurality of bending segments and a plurality of lumens; a bending actuation member, comprising a first bending actuation wire and a second bending actuation wire that are arranged to pass through each lumen separately and cause the steerable member to bend; a tension monitoring member, comprising: a first sensor that is coupled to the first bending actuation wire and configured to provide a first feedback signal responsive to sensing change in tension force of the first bending actuation wire between the pre-bending and the desired bending motion of the steerable member; a second sensor that is coupled to the second bending actuation wire and configured to provide a second feedback signal responsive to sensing change in tension force of the second bending actuation wire between the pre-bending and the desired bending motion of the steerable member; a drive member, comprising: a first motor, coupled to the first bending actuation wire and adapted to actuate the first bending actuation wire; a second motor coupled to the second bending actuation wire and adapted to actuate the second bending actuation wire; a control member that is electrically connected to the tension monitoring member and the drive member, wherein the control member is configured to provide: a first output signal responsive to the first feedback signal, so that the first motor is driven to adjust the length of the first bending actuation wire to maintain a predetermined tension; and a second output signal responsive to the second feedback signal, so that the second motor is driven to adjust the length of the second bending actuation wire to maintain a predetermined tension. In some embodiments, the second bending actuation wire is moveable in an opposite direction of the first bending actuation wire. In some embodiments, when the first bending actuation wire is configured to be actuated to bend the steerable member, and the second bending actuation wire is configured to be driven by the second motor, so that the second bending actuation wire is released and maintained under the predetermined tension in response to the second output signal. In some embodiments, the first sensor or the second sensor is load cell. In some embodiments, the first sensor is further configured to provide a first external-force signal responsive to sensing an external force applied to the steerable member. In some embodiments, the second sensor is further configured to provide a second external-force signal responsive to sensing an external force applied to the steerable member. In other embodiments, the control member is further configured to provide an instruction signal in response to the first external-force signal or the second external-force signal. In other embodiments, the control member further comprises a haptic feedback controller that is configured to process and transfer the information in the form of haptic feedback. In other embodiments, the first motion transmitting unit or the second motion transmitting unit is a lead screw or a ball screw.

In some embodiments is a personalized master controller for a surgical apparatus, comprising: a control platform that is configured to define and input one or more movement signals to the surgical robot, wherein the control platform comprises: an input handle that is translatable in a first plurality of degrees of freedom to provide a plurality of position parameters and/or rotatable in a second plurality of degrees of freedom to provide a plurality of orientation parameters; a plurality of first sensors that are coupled to the input handle and configured to generate first movement signals in response to the position parameters and/or the orientation parameters of the input handle; a connecting part mounted to the input handle and electrically connected to the input handle; and an interchangeable grip, comprising: a detachable handle that is electrically connected the connecting part; one or more grip levers pivoted with respect to the detachable handle, wherein each grip lever is moveable in a third degree of freedom relative to the detachable handle so as to provide a gripping motion parameter; and a second sensor that is coupled to the detachable handle and configured to generate a second movement signal to the control platform in response to the gripping motion parameter. In some embodiments, the first plurality of sensors or the second plurality of sensors includes a rotary encoder, a Hall effector sensor, an angle sensor, a rotational sensor or any combination thereof. In some embodiments, the connecting part further comprises a thread that is coupled to the detachable handle and has a first electrical connecting terminal. In other embodiments, the detachable handle further comprises a second electrical connecting terminal that is electrically connected to the first electrical connecting terminal. In some embodiments, the interchangeable grip comprises two grip levers that are correspondingly pivoted to the detachable handle and allow to move toward each other relative to the detachable handle.

What is claimed is:

1. An endoluminal surgical apparatus comprising:
a bendable endoscope having a proximal end and a distal end;
a robotic surgical arm comprising
an end-effector,
at least one steerable segment having a proximal end and a distal end, wherein the end effector position is controlled by the position of the distal end of the at least one steerable segment,
a flexible tubular member having a proximal end and a distal end, the at least one steerable segment operatively connected to the distal end of the flexible tubular member;
an instrument connector operatively connected to the proximal end of the flexible tubular member, and a plurality of wires extending through the instrument connector, and the flexible tubular member and into the at least one steerable segment where at least a first portion thereof are connected to the at least one steerable segment, wherein, within at least the flexible tubular member, each of the wires is enclosed in a sheath; and
a robotic surgical arm positioner comprising:
a base;
a moveable housing moveable with respect to the base, and
a positioning member received in the moveable housing and moveable with respect to the moveable housing and extendable inwardly and outwardly thereof, the proximal end of the flexible tubular member connected to the positioning member through the instrument connector, the moveable housing moveable linearly, along the base, by a first linear actuator and moveable in an arcuate path by a rotational actuator interposed between the first linear actuator and the moveable housing;
a distal coupler, wherein the distal end of the endoscope is extendable from the distal coupler;
a first flexible sheath having a proximal end and a distal end, the first flexible sheath surrounding a portion of the flexible tubular member, the proximal end of the first flexible sheath fixed in position with respect to the positioning member and the distal end of the first flexible sheath connected to the distal coupler.

2. The endoluminal surgical apparatus of claim 1, further comprising an intermediate coupler having at least a first opening and being connected to the endoscope between the proximal and distal ends thereof, wherein the endoscope extends through the first opening in the intermediate coupler.

3. The endoluminal surgical apparatus of claim 2, wherein the flexible tubular member extends through a second opening in the intermediate coupler and is moveable in therein, but restrained from separation therefrom in a radial direction of the second opening.

4. The endoluminal surgical apparatus of claim 3, further comprising a flexible second sheath surrounding the intermediate coupler and at least a portion of the endoscope and the flexible tubular member.

5. The endoluminal surgical apparatus of claim 1, wherein the instrument connector is directly coupled to the positioning member and moveable therewith.

6. The endoluminal surgical apparatus of claim 1, wherein the moveable housing further comprises at least one cage, and the positioning member is reciprocally moveable inwardly and outwardly thereof.

7. The endoluminal surgical apparatus of claim 1, wherein the moveable housing comprises a mechanical carriage having at least a first cage and a bridge member operatively coupled thereto; and, the proximal end of the first flexible sheath is connected to the bridge member.

8. The endoluminal surgical apparatus of claim 1, wherein the at least one steerable segment comprises a plurality of bending segments configured to bend in an arcuate direction.

9. The endoluminal surgical device of claim 8, wherein the bending directions of at least two adjacent bendable segments are offset from parallel to each other.

10. The endoluminal surgical device of claim 8, wherein the at least one steerable segment includes a first plurality of bendable segments and a second plurality of bendable segments, the first and second plurality of bendable segments are connected by a coupler.

11. The endoluminal surgical apparatus of claim 1, further comprising a third flexible sheath having a proximal end and a distal end, the third flexible sheath surrounding a portion of the bendable endoscope, the proximal end of the third flexible sheath fixed in position with respect to the moveable housing and the distal end of the third flexible sheath connected to the distal coupler.

* * * * *